(12) United States Patent
Dietrich et al.

(10) Patent No.: US 11,572,593 B2
(45) Date of Patent: Feb. 7, 2023

(54) AMPLIFICATION-INTEGRATED GENETIC MATERIAL DEPLETION OF NON-TARGET ORGANISMS USING DIFFERENTIALLY ABUNDANT K-MERS

(71) Applicant: Siemens Healthcare GmbH, Erlangen (DE)

(72) Inventors: Carsten Dietrich, Nuremberg (DE); Yiwei Huang, Erlangen (DE); Mark Matzas, Nuremberg (DE); Andreas Emanuel Posch, Vienna (AT)

(73) Assignee: Siemens Aktiengesellschaft, Munich (DE)

( * ) Notice: Subject to any disclaimer, the term of this patent is extended or adjusted under 35 U.S.C. 154(b) by 639 days.

(21) Appl. No.: 16/469,634

(22) PCT Filed: Nov. 28, 2017

(86) PCT No.: PCT/EP2017/080666
§ 371 (c)(1),
(2) Date: Jun. 13, 2019

(87) PCT Pub. No.: WO2018/114243
PCT Pub. Date: Jun. 28, 2018

(65) Prior Publication Data
US 2019/0345569 A1    Nov. 14, 2019

(30) Foreign Application Priority Data
Dec. 21, 2016   (EP) .................................... 16205822

(51) Int. Cl.
| C12Q 1/68 | (2018.01) |
| C12Q 1/70 | (2006.01) |
| C12Q 1/6893 | (2018.01) |
| C12Q 1/689 | (2018.01) |
| C12Q 1/6895 | (2018.01) |

(52) U.S. Cl.
CPC ........... *C12Q 1/6893* (2013.01); *C12Q 1/689* (2013.01); *C12Q 1/6895* (2013.01); *C12Q 1/701* (2013.01)

(58) Field of Classification Search
CPC .................................................... C12Q 1/701
See application file for complete search history.

(56) References Cited

U.S. PATENT DOCUMENTS

| 5,525,471 A | 6/1996 | Zeng |
| 7,893,251 B2 | 2/2011 | Lorenz |
| 2003/0050470 A1* | 3/2003 | An .......................... C07H 21/00 435/6.14 |
| 2004/0126764 A1 | 7/2004 | Lasken et al. |
| 2009/0170717 A1 | 7/2009 | Agan et al. |
| 2012/0028243 A1 | 2/2012 | Peyrefitte et al. |
| 2013/0020998 A1 | 1/2013 | Howard |
| 2013/0149695 A1 | 6/2013 | Lee et al. |
| 2013/0309676 A1* | 11/2013 | Layne ..................... G16B 25/00 435/6.12 |
| 2015/0079635 A1 | 3/2015 | Heller et al. |
| 2016/0304953 A1* | 10/2016 | Chen ..................... C12Q 1/6874 |

FOREIGN PATENT DOCUMENTS

| CN | 104152437 A | 11/2014 |
| WO | WO 2015/085105 A1 | 6/2015 |
| WO | WO 2016164259 A1 | 10/2016 |

OTHER PUBLICATIONS

Leichty, A.R. and Brisson, D., 2014. Selective whole genome amplification for resequencing target microbial species from complex natural samples. Genetics, 198(2), pp. 473-481. (Year: 2014).*
Leichty et al., 2014. Supporting Information. Genetics, 198(2), pp. 2SI-16S1. (Year: 2014).*
Bowers et al., 2015. Impactof library preparation protocols and template quantity on the metagenomic reconstruction of a mock microbial community. BMC Genomics, 16(1), pp. 1-12. (Year: 2015).*
Bowers et al., 2015. BMC Genomics, 16(1), pp. 1-12, Supporting, pp. 1-7. (Year: 2015).*
Oyola et al., 2016. Whole genome sequencing of Plasmodium falciparum from dried blood spots using selective whole genome amplification. Malaria journal, 15(1), pp. 1-12. (Year: 2016).*
Oyola et al., 2016., Malaria journal, 15(1), pp. 1-12, Supporting document (pp. 1-5). (Year: 2016).*
Jiang, B., Song, K., Ren, J., Deng, M., Sun, F. and Zhang, X., 2012. Comparison of metagenomic samples using sequence signatures. BMC genomics, 13(1), pp. 1-17. (Year: 2012).*
SantaLucia Jr, John. Physical principles and visual-OMP software for optimal PCR design. PCR Primer Design. Humana Press, 2007: pp. 3-33. (Year: 2007).*
Sundararaman SA, Plenderleith LJ, Liu W, Loy DE, Learn GH, Li Y, Shaw KS, et al. Genomes of cryptic chimpanzee *Plasmodium* species reveal key evolutionary events leading to human malaria. Nat Commun. 201;7:11078,. pp. 1-14 (Year: 2016).*
Dubinkina, Veronika B. et al.: "Assessment of k-mer spectrum applicability for magnetic dissimilarity analysis"; in: BMC Bioinformatics; vol. 17; No. 1; pp. 1-11; 2016.
Ge, Fang et al.: "Preferential Amplification of Pathogenic Sequences", in: Scientific Reports, vol. 5:11047; Jun. 11, 2015, pp. 1-14.
Koslicki, David et al.: "ARK: Aggregation of Reads by K—Means for Estimation of Bacterial Community Composition"; in: PLOS ONE; vol. 10; No. 10; Oct. 23, 2015, pp. 1-16.
Molzym Life Science, www.molzym.com/index.php/products/dnaisolationproducts/pathogendnamolysis/molysistechnology; p. 1 (Accessed Oct. 18, 2016).

(Continued)

*Primary Examiner* — Teresa E Strzelecka
*Assistant Examiner* — Olayinka A Oyeyemi
(74) *Attorney, Agent, or Firm* — BakerHostetler

(57) ABSTRACT

The present invention relates to a method of selectively amplifying at least one nucleic acid sequence of at least one microorganism and/or virus in a sample of a subject, wherein k-mers 3 are applied that show a difference in frequency and/or context in the genome 2 of the at least one microorganism and/or virus compared to the genome of the subject 1.

31 Claims, 3 Drawing Sheets
Specification includes a Sequence Listing.

(56) References Cited

OTHER PUBLICATIONS

NEBNext Microbiome DNA Enrichment Kit, www.neb.com/products/e2612nebnextmicrobiomednaenrichmentkit; pp. 1-4; (Accessed Oct. 18, 2016).
Flygare, Steven et al.: "Taxonomer: an interactive metagenomics analysis portal for universal pathogen detection and host mRNA expression profiling"; in: Genome Biology; vol. 17; No. 1; 2016, pp. 1-18.
Onate, Florian Plaza et al: "Quality control of microbiota metagenomics by k-mer analysis", BMC Genomics, Biomed Central Ltd, London, UK, vol. 16, No. 1, p. 183, ISSN: 1471-2164, 2015, pp. 1-10 and supplemental tables pp. 1-5.
Tabb, Loni Philipp et al.: "Characterizing the Empirical Distribution of Prokaryotik Genome n-mers in the Presence of Nullomers"; in: Journal of Computational Biology; vol. 21; No. 10; pp. 732-740; 2014.
European Search Report of European Application No. EP16205822 dated May 31, 2017.
International Search Report & Written Opinion of International Application No. PCT/EP2017/080666 dated Feb. 12, 2018.

* cited by examiner

SEQUENCE LISTING

<160> NUMBER OF SEQ ID NOS: 486

<210> SEQ ID NO 1
<211> LENGTH: 6
<212> TYPE: DNA
<213> ORGANISM: Artificial Sequence
<220> FEATURE:
<223> OTHER INFORMATION: k-mer

```
<220> FEATURE:
<221> NAME/KEY: misc_feature
<222> LOCATION: (3)..(6)
<223> OTHER INFORMATION: n is a, c, g, or t

<400> SEQUENCE: 1 cgnnnn                                                              6

<210> SEQ ID NO 2
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(6)
<223> OTHER INFORMATION: n is a, c, g, or t

<400> SEQUENCE: 2 ncgnnn                                                              6

<210> SEQ ID NO 3
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t

<400> SEQUENCE: 3 nncgnn                                                              6

<210> SEQ ID NO 4
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 4 nnncgn                                                              6

<210> SEQ ID NO 5
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(4)
```

```
<223> OTHER INFORMATION: n is a, c, g, or t

<400> SEQUENCE: 5 nnnncg                                                                      6

<210> SEQ ID NO 6
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (5)..(6)
<223> OTHER INFORMATION: n is a, c, g, or t

<400> SEQUENCE: 6 cgcgnn                                                                      6

<210> SEQ ID NO 7
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 7 cgncgn                                                                      6

<210> SEQ ID NO 8
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(4)
<223> OTHER INFORMATION: n is a, c, g, or t

<400> SEQUENCE: 8 cgnncg                                                                      6

<210> SEQ ID NO 9
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 9 ncgcgn                                                                      6
```

```
<210> SEQ ID NO 10
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 10 ncgncg                                                                  6

<210> SEQ ID NO 11
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(2)
<223> OTHER INFORMATION: n is a, c, g, or t

<400> SEQUENCE: 11 nncgcg                                                                  6

<210> SEQ ID NO 12
<211> LENGTH: 6
<212> TYPE: DNA
<213> ORGANISM: Artificial Sequence
<220> FEATURE:
<223> OTHER INFORMATION: k-mer

<400> SEQUENCE: 12 cgcgcg                                                                  6

<210> SEQ ID NO 13
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(7)
<223> OTHER INFORMATION: n is a, c, g, or t

<400> SEQUENCE: 13 cgnnnnn                                                                 7

<210> SEQ ID NO 14
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(7)
<223> OTHER INFORMATION: n is a, c, g, or t
```

```
<400> SEQUENCE: 14 ncgnnnn                                                              7

<210> SEQ ID NO 15
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (5)..(7)
<223> OTHER INFORMATION: n is a, c, g, or t

<400> SEQUENCE: 15 nncgnnn                                                              7

<210> SEQ ID NO 16
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t

<400> SEQUENCE: 16 nnncgnn                                                              7

<210> SEQ ID NO 17
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 17 nnnncgn                                                              7

<210> SEQ ID NO 18
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(5)
<223> OTHER INFORMATION: n is a, c, g, or t

<400> SEQUENCE: 18 nnnnncg                                                              7
```

```
<210> SEQ ID NO 19
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (5)..(7)
<223> OTHER INFORMATION: n is a, c, g, or t

<400> SEQUENCE: 19 cgcgnnn                                                                      7

<210> SEQ ID NO 20
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t

<400> SEQUENCE: 20 cgncgnn                                                                      7

<210> SEQ ID NO 21
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 21 cgnncgn                                                                      7

<210> SEQ ID NO 22
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(5)
<223> OTHER INFORMATION: n is a, c, g, or t

<400> SEQUENCE: 22 cgnnncg                                                                      7

<210> SEQ ID NO 23
<211> LENGTH: 7
<212> TYPE: DNA
<213> ORGANISM: Artificial Sequence
<220> FEATURE:
```

```
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t

<400> SEQUENCE: 23 ncgcgnn                                                               7

<210> SEQ ID NO 24
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 24 ncgncgn                                                               7

<210> SEQ ID NO 25
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t

<400> SEQUENCE: 25 ncgnncg                                                               7

<210> SEQ ID NO 26
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 26 nncgcgn                                                               7
```

```
<210> SEQ ID NO 27
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t

<400> SEQUENCE: 27 nncgncg                                                                 7

<210> SEQ ID NO 28
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(3)
<223> OTHER INFORMATION: n is a, c, g, or t

<400> SEQUENCE: 28 nnncgcg                                                                 7

<210> SEQ ID NO 29
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (7)..(7)
<223> OTHER INFORMATION: n is a, c, g, or t

<400> SEQUENCE: 29 cgcgcgn                                                                 7

<210> SEQ ID NO 30
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (5)..(5)
<223> OTHER INFORMATION: n is a, c, g, or t

<400> SEQUENCE: 30 cgcgncg                                                                 7

<210> SEQ ID NO 31
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(3)
<223> OTHER INFORMATION: n is a, c, g, or t
```

```
<400> SEQUENCE: 31 cgncgcg                                                               7

<210> SEQ ID NO 32
<211> LENGTH: 7
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t

<400> SEQUENCE: 32 ncgcgcg                                                               7

<210> SEQ ID NO 33
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(8)
<223> OTHER INFORMATION: n is a, c, g, or t

<400> SEQUENCE: 33 cgnnnnnn                                                              8

<210> SEQ ID NO 34
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(8)
<223> OTHER INFORMATION: n is a, c, g, or t

<400> SEQUENCE: 34 ncgnnnnn                                                              8

<210> SEQ ID NO 35
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (5)..(8)
<223> OTHER INFORMATION: n is a, c, g, or t

<400> SEQUENCE: 35 nncgnnnn                                                              8

<210> SEQ ID NO 36
<211> LENGTH: 8
```

-continued

```
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (6)..(8)
<223> OTHER INFORMATION: n is a, c, g, or t

<400> SEQUENCE: 36 nnncgnnn                                                                 8

<210> SEQ ID NO 37
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 37 nnnncgnn                                                                 8

<210> SEQ ID NO 38
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 38 nnnnncgn                                                                 8

<210> SEQ ID NO 39
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(6)
<223> OTHER INFORMATION: n is a, c, g, or t

<400> SEQUENCE: 39 nnnnnncg                                                                 8

<210> SEQ ID NO 40
<211> LENGTH: 8
<212> TYPE: DNA
<213> ORGANISM: Artificial Sequence
<220> FEATURE:
```

```
<223> OTHER INFORMATION: k-mer
<220> FEATURE:
<221> NAME/KEY: misc_feature
<222> LOCATION: (5)..(8)
<223> OTHER INFORMATION: n is a, c, g, or t

<400> SEQUENCE: 40 cgcgnnnn                                                                  8

<210> SEQ ID NO 41
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(8)
<223> OTHER INFORMATION: n is a, c, g, or t

<400> SEQUENCE: 41 cgncgnnn                                                                  8

<210> SEQ ID NO 42
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 42 cgnncgnn                                                                  8

<210> SEQ ID NO 43
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 43 cgnnncgn                                                                  8

<210> SEQ ID NO 44
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
```

```
<222> LOCATION: (3)..(6)
<223> OTHER INFORMATION: n is a, c, g, or t

<400> SEQUENCE: 44 cgnnnncg                                                                    8

<210> SEQ ID NO 45
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(8)
<223> OTHER INFORMATION: n is a, c, g, or t

<400> SEQUENCE: 45 ncgcgnnn                                                                    8

<210> SEQ ID NO 46
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 46 ncgncgnn                                                                    8

<210> SEQ ID NO 47
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 47 ncgnncgn                                                                    8

<210> SEQ ID NO 48
<211> LENGTH: 8
<212> TYPE: DNA
```

```
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(6)
<223> OTHER INFORMATION: n is a, c, g, or t

<400> SEQUENCE: 48 ncgnnncg                                                           8

<210> SEQ ID NO 49
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 49 nncgcgnn                                                           8

<210> SEQ ID NO 50
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 50 nncgncgn                                                           8

<210> SEQ ID NO 51
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t

<400> SEQUENCE: 51 nncgnncg                                                           8
```

<210> SEQ ID NO 52
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 52 nnncgcgn                                                              8

<210> SEQ ID NO 53
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 53 nnncgncg                                                              8

<210> SEQ ID NO 54
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(4)
<223> OTHER INFORMATION: n is a, c, g, or t

<400> SEQUENCE: 54 nnnncgcg                                                              8

<210> SEQ ID NO 55
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (7)..(8)
<223> OTHER INFORMATION: n is a, c, g, or t

<400> SEQUENCE: 55 cgcgcgnn                                                              8

<210> SEQ ID NO 56
<211> LENGTH: 8
<212> TYPE: DNA
<213> ORGANISM: Artificial Sequence
<220> FEATURE:

```
<223> OTHER INFORMATION: k-mer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 56 cgcgncgn                                                                   8

<210> SEQ ID NO 57
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (5)..(6)
<223> OTHER INFORMATION: n is a, c, g, or t

<400> SEQUENCE: 57 cgcgnncg                                                                   8

<210> SEQ ID NO 58
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 58 cgncgcgn                                                                   8

<210> SEQ ID NO 59
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 59 cgncgncg                                                                   8

<210> SEQ ID NO 60
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
```

```
<222> LOCATION: (3)..(4)
<223> OTHER INFORMATION: n is a, c, g, or t

<400> SEQUENCE: 60 cgnncgcg                                                                   8

<210> SEQ ID NO 61
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 61 ncgcgcgn                                                                   8

<210> SEQ ID NO 62
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 62 ncgcgncg                                                                   8

<210> SEQ ID NO 63
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 63 ncgncgcg                                                                   8

<210> SEQ ID NO 64
<211> LENGTH: 8
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(2)
<223> OTHER INFORMATION: n is a, c, g, or t
```

```
<400> SEQUENCE: 64 nncgcgcg                                                                    8

<210> SEQ ID NO 65
<211> LENGTH: 8
<212> TYPE: DNA
<213> ORGANISM: Artificial Sequence
<220> FEATURE:
<223> OTHER INFORMATION: k-mer

<400> SEQUENCE: 65 cgcgcgcg                                                                    8

<210> SEQ ID NO 66
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(2)
<223> OTHER INFORMATION: n is a, c, g, or t

<400> SEQUENCE: 66 nngcgc                                                                      6

<210> SEQ ID NO 67
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(2)
<223> OTHER INFORMATION: n is a, c, g, or t

<400> SEQUENCE: 67 nncggc                                                                      6

<210> SEQ ID NO 68
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 68 ngcgcn                                                                      6

<210> SEQ ID NO 69
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
```

-continued

```
<220> FEATURE:
<221> NAME/KEY: misc_feature
<222> LOCATION: (4)..(4)
<223> OTHER INFORMATION: n is a, c, g, or t

<400> SEQUENCE: 69 ngcngc                                                                6

<210> SEQ ID NO 70
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (5)..(6)
<223> OTHER INFORMATION: n is a, c, g, or t

<400> SEQUENCE: 70 gccgnn                                                                6

<210> SEQ ID NO 71
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (5)..(6)
<223> OTHER INFORMATION: n is a, c, g, or t

<400> SEQUENCE: 71 gcgcnn                                                                6

<210> SEQ ID NO 72
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(4)
<223> OTHER INFORMATION: n is a, c, g, or t

<400> SEQUENCE: 72 cgnngc                                                                6

<210> SEQ ID NO 73
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 73 ncggcn                                                                6

<210> SEQ ID NO 74
```

```
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (5)..(6)
<223> OTHER INFORMATION: n is a, c, g, or t

<400> SEQUENCE: 74 cggcnn                                                                  6

<210> SEQ ID NO 75
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(2)
<223> OTHER INFORMATION: n is a, c, g, or t

<400> SEQUENCE: 75 nngccg                                                                  6

<210> SEQ ID NO 76
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 76 ngccgn                                                                  6

<210> SEQ ID NO 77
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 77 ngcncg                                                                  6

<210> SEQ ID NO 78
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
```

```
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 78 gcncgn                                                                   6

<210> SEQ ID NO 79
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 79 ncgngc                                                                   6

<210> SEQ ID NO 80
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 80 cgngcn                                                                   6

<210> SEQ ID NO 81
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 81 gcngcn                                                                   6

<210> SEQ ID NO 82
<211> LENGTH: 6
<212> TYPE: DNA
<213> ORGANISM: Artificial Sequence
<220> FEATURE:
<223> OTHER INFORMATION: k-mer
<220> FEATURE:
```

```
<221> NAME/KEY: misc_feature
<222> LOCATION: (3)..(4)
<223> OTHER INFORMATION: n is a, c, g, or t

<400> SEQUENCE: 82 gcnngc                                                                     6

<210> SEQ ID NO 83
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (3)..(4)
<223> OTHER INFORMATION: n is a, c, g, or t

<400> SEQUENCE: 83 gcnncg                                                                     6

<210> SEQ ID NO 84
<211> LENGTH: 6
<212> TYPE: DNA
<213> ORGANISM: Artificial Sequence
<220> FEATURE:
<223> OTHER INFORMATION: k-mer
<220> FEATURE:
<221> NAME/KEY: misc_feature
<222> LOCATION: (6)..(6)
<223> OTHER INFORMATION: n is a, c, g, or t

<400> SEQUENCE: 84 cgacgn                                                                     6

<210> SEQ ID NO 85
<211> LENGTH: 6
<212> TYPE: DNA
<213> ORGANISM: Artificial Sequence
<220> FEATURE:
<223> OTHER INFORMATION: k-mer

<400> SEQUENCE: 85 cgacgc                                                                     6

<210> SEQ ID NO 86
<211> LENGTH: 6
<212> TYPE: DNA
<213> ORGANISM: Artificial Sequence
<220> FEATURE:
<223> OTHER INFORMATION: k-mer

<400> SEQUENCE: 86 cggcgc                                                                     6

<210> SEQ ID NO 87
<211> LENGTH: 8
<212> TYPE: DNA
<213> ORGANISM: Artificial Sequence
<220> FEATURE:
<223> OTHER INFORMATION: k-mer

<400> SEQUENCE: 87 cgacgata                                                                   8

<210> SEQ ID NO 88
<211> LENGTH: 8
```

```
<212> TYPE: DNA
<213> ORGANISM: Artificial Sequence
<220> FEATURE:
<223> OTHER INFORMATION: k-mer

<400> SEQUENCE: 88 gcgcgtaa                                                              8

<210> SEQ ID NO 89
<211> LENGTH: 8
<212> TYPE: DNA
<213> ORGANISM: Artificial Sequence
<220> FEATURE:
<223> OTHER INFORMATION: k-mer

<400> SEQUENCE: 89 attacgcg                                                              8

<210> SEQ ID NO 90
<211> LENGTH: 8
<212> TYPE: DNA
<213> ORGANISM: Artificial Sequence
<220> FEATURE:
<223> OTHER INFORMATION: k-mer

<400> SEQUENCE: 90 cgtcgata                                                              8

<210> SEQ ID NO 91
<211> LENGTH: 8
<212> TYPE: DNA
<213> ORGANISM: Artificial Sequence
<220> FEATURE:
<223> OTHER INFORMATION: k-mer

<400> SEQUENCE: 91 cgataacg                                                              8

<210> SEQ ID NO 92
<211> LENGTH: 8
<212> TYPE: DNA
<213> ORGANISM: Artificial Sequence
<220> FEATURE:
<223> OTHER INFORMATION: k-mer

<400> SEQUENCE: 92 cgcgataa                                                              8

<210> SEQ ID NO 93
<211> LENGTH: 8
<212> TYPE: DNA
<213> ORGANISM: Artificial Sequence
<220> FEATURE:
<223> OTHER INFORMATION: k-mer

<400> SEQUENCE: 93 cgataccg                                                              8

<210> SEQ ID NO 94
<211> LENGTH: 8
<212> TYPE: DNA
<213> ORGANISM: Artificial Sequence
<220> FEATURE:
<223> OTHER INFORMATION: k-mer
```

```
<400> SEQUENCE: 94 cgccgata                                                                    8

<210> SEQ ID NO 95
<211> LENGTH: 8
<212> TYPE: DNA
<213> ORGANISM: Artificial Sequence
<220> FEATURE:
<223> OTHER INFORMATION: k-mer

<400> SEQUENCE: 95 tatcgcga                                                                    8

<210> SEQ ID NO 96
<211> LENGTH: 8
<212> TYPE: DNA
<213> ORGANISM: Artificial Sequence
<220> FEATURE:
<223> OTHER INFORMATION: k-mer

<400> SEQUENCE: 96 cgcgtaaa                                                                    8

<210> SEQ ID NO 97
<211> LENGTH: 8
<212> TYPE: DNA
<213> ORGANISM: Artificial Sequence
<220> FEATURE:
<223> OTHER INFORMATION: k-mer

<400> SEQUENCE: 97 atcgtcgc                                                                    8

<210> SEQ ID NO 98
<211> LENGTH: 8
<212> TYPE: DNA
<213> ORGANISM: Artificial Sequence
<220> FEATURE:
<223> OTHER INFORMATION: k-mer

<400> SEQUENCE: 98 cggcgata                                                                    8

<210> SEQ ID NO 99
<211> LENGTH: 8
<212> TYPE: DNA
<213> ORGANISM: Artificial Sequence
<220> FEATURE:
<223> OTHER INFORMATION: k-mer

<400> SEQUENCE: 99 cgatacgc                                                                    8

<210> SEQ ID NO 100
<211> LENGTH: 8
<212> TYPE: DNA
<213> ORGANISM: Artificial Sequence
<220> FEATURE:
<223> OTHER INFORMATION: k-mer

<400> SEQUENCE: 100 atcgcgat                                                                    8

<210> SEQ ID NO 101
```

```
<211> LENGTH: 8
<212> TYPE: DNA
<213> ORGANISM: Artificial Sequence
<220> FEATURE:
<223> OTHER INFORMATION: k-mer

<400> SEQUENCE: 101 cggtacgc                                                                  8

<210> SEQ ID NO 102
<211> LENGTH: 8
<212> TYPE: DNA
<213> ORGANISM: Artificial Sequence
<220> FEATURE:
<223> OTHER INFORMATION: k-mer

<400> SEQUENCE: 102 attgcgcg                                                                  8

<210> SEQ ID NO 103
<211> LENGTH: 8
<212> TYPE: DNA
<213> ORGANISM: Artificial Sequence
<220> FEATURE:
<223> OTHER INFORMATION: k-mer

<400> SEQUENCE: 103 aatcgacg                                                                  8

<210> SEQ ID NO 104
<211> LENGTH: 8
<212> TYPE: DNA
<213> ORGANISM: Artificial Sequence
<220> FEATURE:
<223> OTHER INFORMATION: k-mer

<400> SEQUENCE: 104 cgatagcg                                                                  8

<210> SEQ ID NO 105
<211> LENGTH: 8
<212> TYPE: DNA
<213> ORGANISM: Artificial Sequence
<220> FEATURE:
<223> OTHER INFORMATION: k-mer

<400> SEQUENCE: 105 cgttacgc                                                                  8

<210> SEQ ID NO 106
<211> LENGTH: 8
<212> TYPE: DNA
<213> ORGANISM: Artificial Sequence
<220> FEATURE:
<223> OTHER INFORMATION: k-mer

<400> SEQUENCE: 106 ataacgcg                                                                  8

<210> SEQ ID NO 107
<211> LENGTH: 8
<212> TYPE: DNA
<213> ORGANISM: Artificial Sequence
<220> FEATURE:
<223> OTHER INFORMATION: k-mer
```

```
<400> SEQUENCE: 107 cgcgatac                                                             8

<210> SEQ ID NO 108
<211> LENGTH: 8
<212> TYPE: DNA
<213> ORGANISM: Artificial Sequence
<220> FEATURE:
<223> OTHER INFORMATION: k-mer

<400> SEQUENCE: 108 cgcgaata                                                             8

<210> SEQ ID NO 109
<211> LENGTH: 8
<212> TYPE: DNA
<213> ORGANISM: Artificial Sequence
<220> FEATURE:
<223> OTHER INFORMATION: k-mer

<400> SEQUENCE: 109 tcgcgtaa                                                             8

<210> SEQ ID NO 110
<211> LENGTH: 8
<212> TYPE: DNA
<213> ORGANISM: Artificial Sequence
<220> FEATURE:
<223> OTHER INFORMATION: k-mer

<400> SEQUENCE: 110 aacgcgat                                                             8

<210> SEQ ID NO 111
<211> LENGTH: 8
<212> TYPE: DNA
<213> ORGANISM: Artificial Sequence
<220> FEATURE:
<223> OTHER INFORMATION: k-mer

<400> SEQUENCE: 111 atttcgcg                                                             8

<210> SEQ ID NO 112
<211> LENGTH: 8
<212> TYPE: DNA
<213> ORGANISM: Artificial Sequence
<220> FEATURE:
<223> OTHER INFORMATION: k-mer

<400> SEQUENCE: 112 cgtatcga                                                             8

<210> SEQ ID NO 113
<211> LENGTH: 8
<212> TYPE: DNA
<213> ORGANISM: Artificial Sequence
<220> FEATURE:
<223> OTHER INFORMATION: k-mer

<400> SEQUENCE: 113 atcgacga                                                             8

<210> SEQ ID NO 114
```

```
<211> LENGTH: 8
<212> TYPE: DNA
<213> ORGANISM: Artificial Sequence
<220> FEATURE:
<223> OTHER INFORMATION: k-mer

<400> SEQUENCE: 114 cgtaccga                                                                 8

<210> SEQ ID NO 115
<211> LENGTH: 8
<212> TYPE: DNA
<213> ORGANISM: Artificial Sequence
<220> FEATURE:
<223> OTHER INFORMATION: k-mer

<400> SEQUENCE: 115 tcgcgaaa                                                                 8

<210> SEQ ID NO 116
<211> LENGTH: 8
<212> TYPE: DNA
<213> ORGANISM: Artificial Sequence
<220> FEATURE:
<223> OTHER INFORMATION: k-mer

<400> SEQUENCE: 116 atacgcgc                                                                 8

<210> SEQ ID NO 117
<211> LENGTH: 8
<212> TYPE: DNA
<213> ORGANISM: Artificial Sequence
<220> FEATURE:
<223> OTHER INFORMATION: k-mer

<400> SEQUENCE: 117 cgatatcg                                                                 8

<210> SEQ ID NO 118
<211> LENGTH: 8
<212> TYPE: DNA
<213> ORGANISM: Artificial Sequence
<220> FEATURE:
<223> OTHER INFORMATION: k-mer

<400> SEQUENCE: 118 cgtaaacg                                                                 8

<210> SEQ ID NO 119
<211> LENGTH: 8
<212> TYPE: DNA
<213> ORGANISM: Artificial Sequence
<220> FEATURE:
<223> OTHER INFORMATION: k-mer

<400> SEQUENCE: 119 cgacgatc                                                                 8

<210> SEQ ID NO 120
<211> LENGTH: 8
<212> TYPE: DNA
<213> ORGANISM: Artificial Sequence
<220> FEATURE:
<223> OTHER INFORMATION: k-mer
```

```
<400> SEQUENCE: 120 cgattacg                                                               8

<210> SEQ ID NO 121
<211> LENGTH: 8
<212> TYPE: DNA
<213> ORGANISM: Artificial Sequence
<220> FEATURE:
<223> OTHER INFORMATION: k-mer

<400> SEQUENCE: 121 aatcgtcg                                                               8

<210> SEQ ID NO 122
<211> LENGTH: 8
<212> TYPE: DNA
<213> ORGANISM: Artificial Sequence
<220> FEATURE:
<223> OTHER INFORMATION: k-mer

<400> SEQUENCE: 122 cgccgtta                                                               8

<210> SEQ ID NO 123
<211> LENGTH: 8
<212> TYPE: DNA
<213> ORGANISM: Artificial Sequence
<220> FEATURE:
<223> OTHER INFORMATION: k-mer

<400> SEQUENCE: 123 atcgacgc                                                               8

<210> SEQ ID NO 124
<211> LENGTH: 8
<212> TYPE: DNA
<213> ORGANISM: Artificial Sequence
<220> FEATURE:
<223> OTHER INFORMATION: k-mer

<400> SEQUENCE: 124 cggcgtaa                                                               8

<210> SEQ ID NO 125
<211> LENGTH: 8
<212> TYPE: DNA
<213> ORGANISM: Artificial Sequence
<220> FEATURE:
<223> OTHER INFORMATION: k-mer

<400> SEQUENCE: 125 cgtatcgc                                                               8

<210> SEQ ID NO 126
<211> LENGTH: 8
<212> TYPE: DNA
<213> ORGANISM: Artificial Sequence
<220> FEATURE:
<223> OTHER INFORMATION: k-mer

<400> SEQUENCE: 126 atcgcgaa                                                               8

<210> SEQ ID NO 127
```

```
<211> LENGTH: 8
<212> TYPE: DNA
<213> ORGANISM: Artificial Sequence
<220> FEATURE:
<223> OTHER INFORMATION: k-mer

<400> SEQUENCE: 127 tacgacga                                                                 8

<210> SEQ ID NO 128
<211> LENGTH: 8
<212> TYPE: DNA
<213> ORGANISM: Artificial Sequence
<220> FEATURE:
<223> OTHER INFORMATION: k-mer

<400> SEQUENCE: 128 atatcgcg                                                                 8

<210> SEQ ID NO 129
<211> LENGTH: 8
<212> TYPE: DNA
<213> ORGANISM: Artificial Sequence
<220> FEATURE:
<223> OTHER INFORMATION: k-mer

<400> SEQUENCE: 129 acgcgata                                                                 8

<210> SEQ ID NO 130
<211> LENGTH: 8
<212> TYPE: DNA
<213> ORGANISM: Artificial Sequence
<220> FEATURE:
<223> OTHER INFORMATION: k-mer

<400> SEQUENCE: 130 gcgtcgta                                                                 8

<210> SEQ ID NO 131
<211> LENGTH: 8
<212> TYPE: DNA
<213> ORGANISM: Artificial Sequence
<220> FEATURE:
<223> OTHER INFORMATION: k-mer

<400> SEQUENCE: 131 cgattgcg                                                                 8

<210> SEQ ID NO 132
<211> LENGTH: 8
<212> TYPE: DNA
<213> ORGANISM: Artificial Sequence
<220> FEATURE:
<223> OTHER INFORMATION: k-mer

<400> SEQUENCE: 132 cggtaacg                                                                 8

<210> SEQ ID NO 133
<211> LENGTH: 8
<212> TYPE: DNA
<213> ORGANISM: Artificial Sequence
<220> FEATURE:
<223> OTHER INFORMATION: k-mer
```

```
<400> SEQUENCE: 133 attcgtcg                                                            8

<210> SEQ ID NO 134
<211> LENGTH: 8
<212> TYPE: DNA
<213> ORGANISM: Artificial Sequence
<220> FEATURE:
<223> OTHER INFORMATION: k-mer

<400> SEQUENCE: 134 cgcgtcga                                                            8

<210> SEQ ID NO 135
<211> LENGTH: 8
<212> TYPE: DNA
<213> ORGANISM: Artificial Sequence
<220> FEATURE:
<223> OTHER INFORMATION: k-mer

<400> SEQUENCE: 135 gcgcgata                                                            8

<210> SEQ ID NO 136
<211> LENGTH: 8
<212> TYPE: DNA
<213> ORGANISM: Artificial Sequence
<220> FEATURE:
<223> OTHER INFORMATION: k-mer

<400> SEQUENCE: 136 cgcgatta                                                            8

<210> SEQ ID NO 137
<211> LENGTH: 8
<212> TYPE: DNA
<213> ORGANISM: Artificial Sequence
<220> FEATURE:
<223> OTHER INFORMATION: k-mer

<400> SEQUENCE: 137 acgcgtaa                                                            8

<210> SEQ ID NO 138
<211> LENGTH: 8
<212> TYPE: DNA
<213> ORGANISM: Artificial Sequence
<220> FEATURE:
<223> OTHER INFORMATION: k-mer

<400> SEQUENCE: 138 cgttacga                                                            8

<210> SEQ ID NO 139
<211> LENGTH: 8
<212> TYPE: DNA
<213> ORGANISM: Artificial Sequence
<220> FEATURE:
<223> OTHER INFORMATION: k-mer

<400> SEQUENCE: 139 tacgcgca                                                            8

<210> SEQ ID NO 140
```

```
<211> LENGTH: 8
<212> TYPE: DNA
<213> ORGANISM: Artificial Sequence
<220> FEATURE:
<223> OTHER INFORMATION: k-mer

<400> SEQUENCE: 140 cgcgtaac                                                               8

<210> SEQ ID NO 141
<211> LENGTH: 8
<212> TYPE: DNA
<213> ORGANISM: Artificial Sequence
<220> FEATURE:
<223> OTHER INFORMATION: k-mer

<400> SEQUENCE: 141 cgtaccgc                                                               8

<210> SEQ ID NO 142
<211> LENGTH: 8
<212> TYPE: DNA
<213> ORGANISM: Artificial Sequence
<220> FEATURE:
<223> OTHER INFORMATION: k-mer

<400> SEQUENCE: 142 atcgcgcg                                                               8

<210> SEQ ID NO 143
<211> LENGTH: 8
<212> TYPE: DNA
<213> ORGANISM: Artificial Sequence
<220> FEATURE:
<223> OTHER INFORMATION: k-mer

<400> SEQUENCE: 143 cgtcgtaa                                                               8

<210> SEQ ID NO 144
<211> LENGTH: 8
<212> TYPE: DNA
<213> ORGANISM: Artificial Sequence
<220> FEATURE:
<223> OTHER INFORMATION: k-mer

<400> SEQUENCE: 144 aatacgcg                                                               8

<210> SEQ ID NO 145
<211> LENGTH: 8
<212> TYPE: DNA
<213> ORGANISM: Artificial Sequence
<220> FEATURE:
<223> OTHER INFORMATION: k-mer

<400> SEQUENCE: 145 atcggcga                                                               8

<210> SEQ ID NO 146
<211> LENGTH: 8
<212> TYPE: DNA
<213> ORGANISM: Artificial Sequence
<220> FEATURE:
<223> OTHER INFORMATION: k-mer
```

```
<400> SEQUENCE: 146 cgcgaaaa                                                                    8

<210> SEQ ID NO 147
<211> LENGTH: 8
<212> TYPE: DNA
<213> ORGANISM: Artificial Sequence
<220> FEATURE:
<223> OTHER INFORMATION: k-mer

<400> SEQUENCE: 147 tacgcgaa                                                                    8

<210> SEQ ID NO 148
<211> LENGTH: 8
<212> TYPE: DNA
<213> ORGANISM: Artificial Sequence
<220> FEATURE:
<223> OTHER INFORMATION: k-mer

<400> SEQUENCE: 148 acgtatcg                                                                    8

<210> SEQ ID NO 149
<211> LENGTH: 8
<212> TYPE: DNA
<213> ORGANISM: Artificial Sequence
<220> FEATURE:
<223> OTHER INFORMATION: k-mer

<400> SEQUENCE: 149 gtacgcga                                                                    8

<210> SEQ ID NO 150
<211> LENGTH: 8
<212> TYPE: DNA
<213> ORGANISM: Artificial Sequence
<220> FEATURE:
<223> OTHER INFORMATION: k-mer

<400> SEQUENCE: 150 attcgcga                                                                    8

<210> SEQ ID NO 151
<211> LENGTH: 8
<212> TYPE: DNA
<213> ORGANISM: Artificial Sequence
<220> FEATURE:
<223> OTHER INFORMATION: k-mer

<400> SEQUENCE: 151 acgacgat                                                                    8

<210> SEQ ID NO 152
<211> LENGTH: 8
<212> TYPE: DNA
<213> ORGANISM: Artificial Sequence
<220> FEATURE:
<223> OTHER INFORMATION: k-mer

<400> SEQUENCE: 152 cgcgaacg                                                                    8

<210> SEQ ID NO 153
```

```
<211> LENGTH: 8
<212> TYPE: DNA
<213> ORGANISM: Artificial Sequence
<220> FEATURE:
<223> OTHER INFORMATION: k-mer

<400> SEQUENCE: 153 cgcgacga                                                                 8

<210> SEQ ID NO 154
<211> LENGTH: 8
<212> TYPE: DNA
<213> ORGANISM: Artificial Sequence
<220> FEATURE:
<223> OTHER INFORMATION: k-mer

<400> SEQUENCE: 154 cgcgacaa                                                                 8

<210> SEQ ID NO 155
<211> LENGTH: 8
<212> TYPE: DNA
<213> ORGANISM: Artificial Sequence
<220> FEATURE:
<223> OTHER INFORMATION: k-mer

<400> SEQUENCE: 155 cgtaacga                                                                 8

<210> SEQ ID NO 156
<211> LENGTH: 8
<212> TYPE: DNA
<213> ORGANISM: Artificial Sequence
<220> FEATURE:
<223> OTHER INFORMATION: k-mer

<400> SEQUENCE: 156 attcgcgc                                                                 8

<210> SEQ ID NO 157
<211> LENGTH: 8
<212> TYPE: DNA
<213> ORGANISM: Artificial Sequence
<220> FEATURE:
<223> OTHER INFORMATION: k-mer

<400> SEQUENCE: 157 atcgtcga                                                                 8

<210> SEQ ID NO 158
<211> LENGTH: 8
<212> TYPE: DNA
<213> ORGANISM: Artificial Sequence
<220> FEATURE:
<223> OTHER INFORMATION: k-mer

<400> SEQUENCE: 158 atcgacgg                                                                 8

<210> SEQ ID NO 159
<211> LENGTH: 8
<212> TYPE: DNA
<213> ORGANISM: Artificial Sequence
<220> FEATURE:
<223> OTHER INFORMATION: k-mer
```

```
<400> SEQUENCE: 159 ccgcgata                                                            8

<210> SEQ ID NO 160
<211> LENGTH: 8
<212> TYPE: DNA
<213> ORGANISM: Artificial Sequence
<220> FEATURE:
<223> OTHER INFORMATION: k-mer

<400> SEQUENCE: 160 acgaatcg                                                            8

<210> SEQ ID NO 161
<211> LENGTH: 8
<212> TYPE: DNA
<213> ORGANISM: Artificial Sequence
<220> FEATURE:
<223> OTHER INFORMATION: k-mer

<400> SEQUENCE: 161 acgacgcg                                                            8

<210> SEQ ID NO 162
<211> LENGTH: 8
<212> TYPE: DNA
<213> ORGANISM: Artificial Sequence
<220> FEATURE:
<223> OTHER INFORMATION: k-mer

<400> SEQUENCE: 162 cgaatacg                                                            8

<210> SEQ ID NO 163
<211> LENGTH: 8
<212> TYPE: DNA
<213> ORGANISM: Artificial Sequence
<220> FEATURE:
<223> OTHER INFORMATION: k-mer

<400> SEQUENCE: 163 agcgcgta                                                            8

<210> SEQ ID NO 164
<211> LENGTH: 8
<212> TYPE: DNA
<213> ORGANISM: Artificial Sequence
<220> FEATURE:
<223> OTHER INFORMATION: k-mer

<400> SEQUENCE: 164 atcgttcg                                                            8

<210> SEQ ID NO 165
<211> LENGTH: 8
<212> TYPE: DNA
<213> ORGANISM: Artificial Sequence
<220> FEATURE:
<223> OTHER INFORMATION: k-mer

<400> SEQUENCE: 165 gcgcgtta                                                            8

<210> SEQ ID NO 166
```

```
<211> LENGTH: 8
<212> TYPE: DNA
<213> ORGANISM: Artificial Sequence
<220> FEATURE:
<223> OTHER INFORMATION: k-mer

<400> SEQUENCE: 166 atgcgacg                                                                 8

<210> SEQ ID NO 167
<211> LENGTH: 8
<212> TYPE: DNA
<213> ORGANISM: Artificial Sequence
<220> FEATURE:
<223> OTHER INFORMATION: k-mer

<400> SEQUENCE: 167 gtcgcgta                                                                 8

<210> SEQ ID NO 168
<211> LENGTH: 8
<212> TYPE: DNA
<213> ORGANISM: Artificial Sequence
<220> FEATURE:
<223> OTHER INFORMATION: k-mer

<400> SEQUENCE: 168 acgcgcaa                                                                 8

<210> SEQ ID NO 169
<211> LENGTH: 8
<212> TYPE: DNA
<213> ORGANISM: Artificial Sequence
<220> FEATURE:
<223> OTHER INFORMATION: k-mer

<400> SEQUENCE: 169 acgatacg                                                                 8

<210> SEQ ID NO 170
<211> LENGTH: 8
<212> TYPE: DNA
<213> ORGANISM: Artificial Sequence
<220> FEATURE:
<223> OTHER INFORMATION: k-mer

<400> SEQUENCE: 170 tcgcgcaa                                                                 8

<210> SEQ ID NO 171
<211> LENGTH: 8
<212> TYPE: DNA
<213> ORGANISM: Artificial Sequence
<220> FEATURE:
<223> OTHER INFORMATION: k-mer

<400> SEQUENCE: 171 aatgcgcg                                                                 8

<210> SEQ ID NO 172
<211> LENGTH: 8
<212> TYPE: DNA
<213> ORGANISM: Artificial Sequence
<220> FEATURE:
<223> OTHER INFORMATION: k-mer
```

```
<400> SEQUENCE: 172 cgcggtaa                                                                 8

<210> SEQ ID NO 173
<211> LENGTH: 8
<212> TYPE: DNA
<213> ORGANISM: Artificial Sequence
<220> FEATURE:
<223> OTHER INFORMATION: k-mer

<400> SEQUENCE: 173 cggtacga                                                                 8

<210> SEQ ID NO 174
<211> LENGTH: 8
<212> TYPE: DNA
<213> ORGANISM: Artificial Sequence
<220> FEATURE:
<223> OTHER INFORMATION: k-mer

<400> SEQUENCE: 174 taccgcga                                                                 8

<210> SEQ ID NO 175
<211> LENGTH: 8
<212> TYPE: DNA
<213> ORGANISM: Artificial Sequence
<220> FEATURE:
<223> OTHER INFORMATION: k-mer

<400> SEQUENCE: 175 aacgcgta                                                                 8

<210> SEQ ID NO 176
<211> LENGTH: 8
<212> TYPE: DNA
<213> ORGANISM: Artificial Sequence
<220> FEATURE:
<223> OTHER INFORMATION: k-mer

<400> SEQUENCE: 176 atacgccg                                                                 8

<210> SEQ ID NO 177
<211> LENGTH: 8
<212> TYPE: DNA
<213> ORGANISM: Artificial Sequence
<220> FEATURE:
<223> OTHER INFORMATION: k-mer

<400> SEQUENCE: 177 cgacggta                                                                 8

<210> SEQ ID NO 178
<211> LENGTH: 8
<212> TYPE: DNA
<213> ORGANISM: Artificial Sequence
<220> FEATURE:
<223> OTHER INFORMATION: k-mer

<400> SEQUENCE: 178 ccgatacg                                                                 8

<210> SEQ ID NO 179
```

-continued

```
<211> LENGTH: 8
<212> TYPE: DNA
<213> ORGANISM: Artificial Sequence
<220> FEATURE:
<223> OTHER INFORMATION: k-mer

<400> SEQUENCE: 179 gcgcgaaa                                                                 8

<210> SEQ ID NO 180
<211> LENGTH: 8
<212> TYPE: DNA
<213> ORGANISM: Artificial Sequence
<220> FEATURE:
<223> OTHER INFORMATION: k-mer

<400> SEQUENCE: 180 cgtcgtta                                                                 8

<210> SEQ ID NO 181
<211> LENGTH: 8
<212> TYPE: DNA
<213> ORGANISM: Artificial Sequence
<220> FEATURE:
<223> OTHER INFORMATION: k-mer

<400> SEQUENCE: 181 tgcgcgaa                                                                 8

<210> SEQ ID NO 182
<211> LENGTH: 8
<212> TYPE: DNA
<213> ORGANISM: Artificial Sequence
<220> FEATURE:
<223> OTHER INFORMATION: k-mer

<400> SEQUENCE: 182 cgtcaacg                                                                 8

<210> SEQ ID NO 183
<211> LENGTH: 8
<212> TYPE: DNA
<213> ORGANISM: Artificial Sequence
<220> FEATURE:
<223> OTHER INFORMATION: k-mer

<400> SEQUENCE: 183 tcgacgaa                                                                 8

<210> SEQ ID NO 184
<211> LENGTH: 8
<212> TYPE: DNA
<213> ORGANISM: Artificial Sequence
<220> FEATURE:
<223> OTHER INFORMATION: k-mer

<400> SEQUENCE: 184 cgcgcata                                                                 8

<210> SEQ ID NO 185
<211> LENGTH: 8
<212> TYPE: DNA
<213> ORGANISM: Artificial Sequence
<220> FEATURE:
<223> OTHER INFORMATION: k-mer
```

-continued

```
<400> SEQUENCE: 185 cgtcgtac                                                              8

<210> SEQ ID NO 186
<211> LENGTH: 8
<212> TYPE: DNA
<213> ORGANISM: Artificial Sequence
<220> FEATURE:
<223> OTHER INFORMATION: k-mer

<400> SEQUENCE: 186 cgttgcga                                                              8

<210> SEQ ID NO 187
<211> LENGTH: 6
<212> TYPE: DNA
<213> ORGANISM: Artificial Sequence
<220> FEATURE:
<223> OTHER INFORMATION: k-mer

<400> SEQUENCE: 187 cgtcga                                                                6

<210> SEQ ID NO 188
<211> LENGTH: 6
<212> TYPE: DNA
<213> ORGANISM: Artificial Sequence
<220> FEATURE:
<223> OTHER INFORMATION: k-mer

<400> SEQUENCE: 188 cgacga                                                                6

<210> SEQ ID NO 189
<211> LENGTH: 6
<212> TYPE: DNA
<213> ORGANISM: Artificial Sequence
<220> FEATURE:
<223> OTHER INFORMATION: k-mer

<400> SEQUENCE: 189 cgacgc                                                                6

<210> SEQ ID NO 190
<211> LENGTH: 6
<212> TYPE: DNA
<213> ORGANISM: Artificial Sequence
<220> FEATURE:
<223> OTHER INFORMATION: k-mer

<400> SEQUENCE: 190 cgatcg                                                                6

<210> SEQ ID NO 191
<211> LENGTH: 6
<212> TYPE: DNA
<213> ORGANISM: Artificial Sequence
<220> FEATURE:
<223> OTHER INFORMATION: k-mer

<400> SEQUENCE: 191 cgtcgc                                                                6

<210> SEQ ID NO 192
```

```
<211> LENGTH: 6
<212> TYPE: DNA
<213> ORGANISM: Artificial Sequence
<220> FEATURE:
<223> OTHER INFORMATION: k-mer

<400> SEQUENCE: 192 acgacg                                                                      6

<210> SEQ ID NO 193
<211> LENGTH: 6
<212> TYPE: DNA
<213> ORGANISM: Artificial Sequence
<220> FEATURE:
<223> OTHER INFORMATION: k-mer

<400> SEQUENCE: 193 cgcgac                                                                      6

<210> SEQ ID NO 194
<211> LENGTH: 6
<212> TYPE: DNA
<213> ORGANISM: Artificial Sequence
<220> FEATURE:
<223> OTHER INFORMATION: k-mer

<400> SEQUENCE: 194 cgaccg                                                                      6

<210> SEQ ID NO 195
<211> LENGTH: 6
<212> TYPE: DNA
<213> ORGANISM: Artificial Sequence
<220> FEATURE:
<223> OTHER INFORMATION: k-mer

<400> SEQUENCE: 195 cgccga                                                                      6

<210> SEQ ID NO 196
<211> LENGTH: 6
<212> TYPE: DNA
<213> ORGANISM: Artificial Sequence
<220> FEATURE:
<223> OTHER INFORMATION: k-mer

<400> SEQUENCE: 196 acgtcg                                                                      6

<210> SEQ ID NO 197
<211> LENGTH: 6
<212> TYPE: DNA
<213> ORGANISM: Artificial Sequence
<220> FEATURE:
<223> OTHER INFORMATION: k-mer

<400> SEQUENCE: 197 tcgcga                                                                      6

<210> SEQ ID NO 198
<211> LENGTH: 6
<212> TYPE: DNA
<213> ORGANISM: Artificial Sequence
<220> FEATURE:
<223> OTHER INFORMATION: k-mer
```

```
<400> SEQUENCE: 198 acgcgc                                                              6

<210> SEQ ID NO 199
<211> LENGTH: 6
<212> TYPE: DNA
<213> ORGANISM: Artificial Sequence
<220> FEATURE:
<223> OTHER INFORMATION: k-mer

<400> SEQUENCE: 199 cgcgta                                                              6

<210> SEQ ID NO 200
<211> LENGTH: 6
<212> TYPE: DNA
<213> ORGANISM: Artificial Sequence
<220> FEATURE:
<223> OTHER INFORMATION: k-mer

<400> SEQUENCE: 200 gtcgac                                                              6

<210> SEQ ID NO 201
<211> LENGTH: 6
<212> TYPE: DNA
<213> ORGANISM: Artificial Sequence
<220> FEATURE:
<223> OTHER INFORMATION: k-mer

<400> SEQUENCE: 201 acgcga                                                              6

<210> SEQ ID NO 202
<211> LENGTH: 6
<212> TYPE: DNA
<213> ORGANISM: Artificial Sequence
<220> FEATURE:
<223> OTHER INFORMATION: k-mer

<400> SEQUENCE: 202 cgcgaa                                                              6

<210> SEQ ID NO 203
<211> LENGTH: 6
<212> TYPE: DNA
<213> ORGANISM: Artificial Sequence
<220> FEATURE:
<223> OTHER INFORMATION: k-mer

<400> SEQUENCE: 203 aacgcg                                                              6

<210> SEQ ID NO 204
<211> LENGTH: 6
<212> TYPE: DNA
<213> ORGANISM: Artificial Sequence
<220> FEATURE:
<223> OTHER INFORMATION: k-mer

<400> SEQUENCE: 204 cgtacg                                                              6

<210> SEQ ID NO 205
```

```
<211> LENGTH: 6
<212> TYPE: DNA
<213> ORGANISM: Artificial Sequence
<220> FEATURE:
<223> OTHER INFORMATION: k-mer

<400> SEQUENCE: 205 gacgac                                                                     6

<210> SEQ ID NO 206
<211> LENGTH: 6
<212> TYPE: DNA
<213> ORGANISM: Artificial Sequence
<220> FEATURE:
<223> OTHER INFORMATION: k-mer

<400> SEQUENCE: 206 acgcgt                                                                     6

<210> SEQ ID NO 207
<211> LENGTH: 6
<212> TYPE: DNA
<213> ORGANISM: Artificial Sequence
<220> FEATURE:
<223> OTHER INFORMATION: k-mer

<400> SEQUENCE: 207 cgaacg                                                                     6

<210> SEQ ID NO 208
<211> LENGTH: 6
<212> TYPE: DNA
<213> ORGANISM: Artificial Sequence
<220> FEATURE:
<223> OTHER INFORMATION: k-mer

<400> SEQUENCE: 208 atcgac                                                                     6

<210> SEQ ID NO 209
<211> LENGTH: 6
<212> TYPE: DNA
<213> ORGANISM: Artificial Sequence
<220> FEATURE:
<223> OTHER INFORMATION: k-mer

<400> SEQUENCE: 209 atcgcg                                                                     6

<210> SEQ ID NO 210
<211> LENGTH: 6
<212> TYPE: DNA
<213> ORGANISM: Artificial Sequence
<220> FEATURE:
<223> OTHER INFORMATION: k-mer

<400> SEQUENCE: 210 gcgcaa                                                                     6

<210> SEQ ID NO 211
<211> LENGTH: 6
<212> TYPE: DNA
<213> ORGANISM: Artificial Sequence
<220> FEATURE:
<223> OTHER INFORMATION: k-mer
```

```
<400> SEQUENCE: 211 cgccaa                                                              6

<210> SEQ ID NO 212
<211> LENGTH: 6
<212> TYPE: DNA
<213> ORGANISM: Artificial Sequence
<220> FEATURE:
<223> OTHER INFORMATION: k-mer

<400> SEQUENCE: 212 cgacaa                                                              6

<210> SEQ ID NO 213
<211> LENGTH: 6
<212> TYPE: DNA
<213> ORGANISM: Artificial Sequence
<220> FEATURE:
<223> OTHER INFORMATION: k-mer

<400> SEQUENCE: 213 atgcgc                                                              6

<210> SEQ ID NO 214
<211> LENGTH: 6
<212> TYPE: DNA
<213> ORGANISM: Artificial Sequence
<220> FEATURE:
<223> OTHER INFORMATION: k-mer

<400> SEQUENCE: 214 gtcgca                                                              6

<210> SEQ ID NO 215
<211> LENGTH: 6
<212> TYPE: DNA
<213> ORGANISM: Artificial Sequence
<220> FEATURE:
<223> OTHER INFORMATION: k-mer

<400> SEQUENCE: 215 cgatgc                                                              6

<210> SEQ ID NO 216
<211> LENGTH: 6
<212> TYPE: DNA
<213> ORGANISM: Artificial Sequence
<220> FEATURE:
<223> OTHER INFORMATION: k-mer

<400> SEQUENCE: 216 gcgtac                                                              6

<210> SEQ ID NO 217
<211> LENGTH: 6
<212> TYPE: DNA
<213> ORGANISM: Artificial Sequence
<220> FEATURE:
<223> OTHER INFORMATION: k-mer

<400> SEQUENCE: 217 acgacc                                                              6

<210> SEQ ID NO 218
```

```
<211> LENGTH: 6
<212> TYPE: DNA
<213> ORGANISM: Artificial Sequence
<220> FEATURE:
<223> OTHER INFORMATION: k-mer

<400> SEQUENCE: 218 gcggta                                                                    6

<210> SEQ ID NO 219
<211> LENGTH: 6
<212> TYPE: DNA
<213> ORGANISM: Artificial Sequence
<220> FEATURE:
<223> OTHER INFORMATION: k-mer

<400> SEQUENCE: 219 caacgc                                                                    6

<210> SEQ ID NO 220
<211> LENGTH: 6
<212> TYPE: DNA
<213> ORGANISM: Artificial Sequence
<220> FEATURE:
<223> OTHER INFORMATION: k-mer

<400> SEQUENCE: 220 tgcgca                                                                    6

<210> SEQ ID NO 221
<211> LENGTH: 6
<212> TYPE: DNA
<213> ORGANISM: Artificial Sequence
<220> FEATURE:
<223> OTHER INFORMATION: k-mer

<400> SEQUENCE: 221 atcgtc                                                                    6

<210> SEQ ID NO 222
<211> LENGTH: 6
<212> TYPE: DNA
<213> ORGANISM: Artificial Sequence
<220> FEATURE:
<223> OTHER INFORMATION: k-mer

<400> SEQUENCE: 222 cgcaac                                                                    6

<210> SEQ ID NO 223
<211> LENGTH: 6
<212> TYPE: DNA
<213> ORGANISM: Artificial Sequence
<220> FEATURE:
<223> OTHER INFORMATION: k-mer

<400> SEQUENCE: 223 catcgc                                                                    6

<210> SEQ ID NO 224
<211> LENGTH: 6
<212> TYPE: DNA
<213> ORGANISM: Artificial Sequence
<220> FEATURE:
<223> OTHER INFORMATION: k-mer
```

```
<400> SEQUENCE: 224 cgatac                                                                    6

<210> SEQ ID NO 225
<211> LENGTH: 6
<212> TYPE: DNA
<213> ORGANISM: Artificial Sequence
<220> FEATURE:
<223> OTHER INFORMATION: k-mer

<400> SEQUENCE: 225 cgcatc                                                                    6

<210> SEQ ID NO 226
<211> LENGTH: 6
<212> TYPE: DNA
<213> ORGANISM: Artificial Sequence
<220> FEATURE:
<223> OTHER INFORMATION: k-mer

<400> SEQUENCE: 226 tcgaca                                                                    6

<210> SEQ ID NO 227
<211> LENGTH: 6
<212> TYPE: DNA
<213> ORGANISM: Artificial Sequence
<220> FEATURE:
<223> OTHER INFORMATION: k-mer

<400> SEQUENCE: 227 gcgata                                                                    6

<210> SEQ ID NO 228
<211> LENGTH: 6
<212> TYPE: DNA
<213> ORGANISM: Artificial Sequence
<220> FEATURE:
<223> OTHER INFORMATION: k-mer

<400> SEQUENCE: 228 agcgac                                                                    6

<210> SEQ ID NO 229
<211> LENGTH: 6
<212> TYPE: DNA
<213> ORGANISM: Artificial Sequence
<220> FEATURE:
<223> OTHER INFORMATION: k-mer

<400> SEQUENCE: 229 cgataa                                                                    6

<210> SEQ ID NO 230
<211> LENGTH: 6
<212> TYPE: DNA
<213> ORGANISM: Artificial Sequence
<220> FEATURE:
<223> OTHER INFORMATION: k-mer

<400> SEQUENCE: 230 cgttgc                                                                    6

<210> SEQ ID NO 231
```

```
<211> LENGTH: 6
<212> TYPE: DNA
<213> ORGANISM: Artificial Sequence
<220> FEATURE:
<223> OTHER INFORMATION: k-mer

<400> SEQUENCE: 231 gcgtca                                                                      6

<210> SEQ ID NO 232
<211> LENGTH: 6
<212> TYPE: DNA
<213> ORGANISM: Artificial Sequence
<220> FEATURE:
<223> OTHER INFORMATION: k-mer

<400> SEQUENCE: 232 gcgaac                                                                      6

<210> SEQ ID NO 233
<211> LENGTH: 6
<212> TYPE: DNA
<213> ORGANISM: Artificial Sequence
<220> FEATURE:
<223> OTHER INFORMATION: k-mer

<400> SEQUENCE: 233 aacgcc                                                                      6

<210> SEQ ID NO 234
<211> LENGTH: 6
<212> TYPE: DNA
<213> ORGANISM: Artificial Sequence
<220> FEATURE:
<223> OTHER INFORMATION: k-mer

<400> SEQUENCE: 234 atgtcg                                                                      6

<210> SEQ ID NO 235
<211> LENGTH: 6
<212> TYPE: DNA
<213> ORGANISM: Artificial Sequence
<220> FEATURE:
<223> OTHER INFORMATION: k-mer

<400> SEQUENCE: 235 cggtac                                                                      6

<210> SEQ ID NO 236
<211> LENGTH: 6
<212> TYPE: DNA
<213> ORGANISM: Artificial Sequence
<220> FEATURE:
<223> OTHER INFORMATION: k-mer

<400> SEQUENCE: 236 caatcg                                                                      6

<210> SEQ ID NO 237
<211> LENGTH: 6
<212> TYPE: DNA
<213> ORGANISM: Artificial Sequence
<220> FEATURE:
<223> OTHER INFORMATION: k-mer
```

-continued

```
<400> SEQUENCE: 237 tatcga                                                              6

<210> SEQ ID NO 238
<211> LENGTH: 6
<212> TYPE: DNA
<213> ORGANISM: Artificial Sequence
<220> FEATURE:
<223> OTHER INFORMATION: k-mer

<400> SEQUENCE: 238 cgcaaa                                                              6

<210> SEQ ID NO 239
<211> LENGTH: 6
<212> TYPE: DNA
<213> ORGANISM: Artificial Sequence
<220> FEATURE:
<223> OTHER INFORMATION: k-mer

<400> SEQUENCE: 239 accgat                                                              6

<210> SEQ ID NO 240
<211> LENGTH: 6
<212> TYPE: DNA
<213> ORGANISM: Artificial Sequence
<220> FEATURE:
<223> OTHER INFORMATION: k-mer

<400> SEQUENCE: 240 aagcgc                                                              6

<210> SEQ ID NO 241
<211> LENGTH: 6
<212> TYPE: DNA
<213> ORGANISM: Artificial Sequence
<220> FEATURE:
<223> OTHER INFORMATION: k-mer

<400> SEQUENCE: 241 gcgcta                                                              6

<210> SEQ ID NO 242
<211> LENGTH: 6
<212> TYPE: DNA
<213> ORGANISM: Artificial Sequence
<220> FEATURE:
<223> OTHER INFORMATION: k-mer

<400> SEQUENCE: 242 gtcgta                                                              6

<210> SEQ ID NO 243
<211> LENGTH: 6
<212> TYPE: DNA
<213> ORGANISM: Artificial Sequence
<220> FEATURE:
<223> OTHER INFORMATION: k-mer

<400> SEQUENCE: 243 ccgata                                                              6

<210> SEQ ID NO 244
```

```
<211> LENGTH: 6
<212> TYPE: DNA
<213> ORGANISM: Artificial Sequence
<220> FEATURE:
<223> OTHER INFORMATION: k-mer

<400> SEQUENCE: 244 gcgtaa                                                                    6

<210> SEQ ID NO 245
<211> LENGTH: 6
<212> TYPE: DNA
<213> ORGANISM: Artificial Sequence
<220> FEATURE:
<223> OTHER INFORMATION: k-mer

<400> SEQUENCE: 245 catcga                                                                    6

<210> SEQ ID NO 246
<211> LENGTH: 6
<212> TYPE: DNA
<213> ORGANISM: Artificial Sequence
<220> FEATURE:
<223> OTHER INFORMATION: k-mer

<400> SEQUENCE: 246 ggcgta                                                                    6

<210> SEQ ID NO 247
<211> LENGTH: 6
<212> TYPE: DNA
<213> ORGANISM: Artificial Sequence
<220> FEATURE:
<223> OTHER INFORMATION: k-mer

<400> SEQUENCE: 247 attcgc                                                                    6

<210> SEQ ID NO 248
<211> LENGTH: 6
<212> TYPE: DNA
<213> ORGANISM: Artificial Sequence
<220> FEATURE:
<223> OTHER INFORMATION: k-mer

<400> SEQUENCE: 248 atcgat                                                                    6

<210> SEQ ID NO 249
<211> LENGTH: 6
<212> TYPE: DNA
<213> ORGANISM: Artificial Sequence
<220> FEATURE:
<223> OTHER INFORMATION: k-mer

<400> SEQUENCE: 249 cgtcaa                                                                    6

<210> SEQ ID NO 250
<211> LENGTH: 6
<212> TYPE: DNA
<213> ORGANISM: Artificial Sequence
<220> FEATURE:
<223> OTHER INFORMATION: k-mer
```

```
<400> SEQUENCE: 250 aacgac                                                                      6

<210> SEQ ID NO 251
<211> LENGTH: 6
<212> TYPE: DNA
<213> ORGANISM: Artificial Sequence
<220> FEATURE:
<223> OTHER INFORMATION: k-mer

<400> SEQUENCE: 251 atatcg                                                                      6

<210> SEQ ID NO 252
<211> LENGTH: 6
<212> TYPE: DNA
<213> ORGANISM: Artificial Sequence
<220> FEATURE:
<223> OTHER INFORMATION: k-mer

<400> SEQUENCE: 252 acgaca                                                                      6

<210> SEQ ID NO 253
<211> LENGTH: 6
<212> TYPE: DNA
<213> ORGANISM: Artificial Sequence
<220> FEATURE:
<223> OTHER INFORMATION: k-mer

<400> SEQUENCE: 253 cgatga                                                                      6

<210> SEQ ID NO 254
<211> LENGTH: 6
<212> TYPE: DNA
<213> ORGANISM: Artificial Sequence
<220> FEATURE:
<223> OTHER INFORMATION: k-mer

<400> SEQUENCE: 254 ataccg                                                                      6

<210> SEQ ID NO 255
<211> LENGTH: 6
<212> TYPE: DNA
<213> ORGANISM: Artificial Sequence
<220> FEATURE:
<223> OTHER INFORMATION: k-mer

<400> SEQUENCE: 255 cgctac                                                                      6

<210> SEQ ID NO 256
<211> LENGTH: 6
<212> TYPE: DNA
<213> ORGANISM: Artificial Sequence
<220> FEATURE:
<223> OTHER INFORMATION: k-mer

<400> SEQUENCE: 256 aatgcg                                                                      6

<210> SEQ ID NO 257
```

-continued

```
<211> LENGTH: 6
<212> TYPE: DNA
<213> ORGANISM: Artificial Sequence
<220> FEATURE:
<223> OTHER INFORMATION: k-mer

<400> SEQUENCE: 257 tcgcaa                                                                    6

<210> SEQ ID NO 258
<211> LENGTH: 6
<212> TYPE: DNA
<213> ORGANISM: Artificial Sequence
<220> FEATURE:
<223> OTHER INFORMATION: k-mer

<400> SEQUENCE: 258 gtcgaa                                                                    6

<210> SEQ ID NO 259
<211> LENGTH: 6
<212> TYPE: DNA
<213> ORGANISM: Artificial Sequence
<220> FEATURE:
<223> OTHER INFORMATION: k-mer

<400> SEQUENCE: 259 caacga                                                                    6

<210> SEQ ID NO 260
<211> LENGTH: 6
<212> TYPE: DNA
<213> ORGANISM: Artificial Sequence
<220> FEATURE:
<223> OTHER INFORMATION: k-mer

<400> SEQUENCE: 260 attgcg                                                                    6

<210> SEQ ID NO 261
<211> LENGTH: 6
<212> TYPE: DNA
<213> ORGANISM: Artificial Sequence
<220> FEATURE:
<223> OTHER INFORMATION: k-mer

<400> SEQUENCE: 261 cgttga                                                                    6

<210> SEQ ID NO 262
<211> LENGTH: 6
<212> TYPE: DNA
<213> ORGANISM: Artificial Sequence
<220> FEATURE:
<223> OTHER INFORMATION: k-mer

<400> SEQUENCE: 262 cgatca                                                                    6

<210> SEQ ID NO 263
<211> LENGTH: 6
<212> TYPE: DNA
<213> ORGANISM: Artificial Sequence
<220> FEATURE:
<223> OTHER INFORMATION: k-mer
```

```
<400> SEQUENCE: 263 tcgtca                                                              6

<210> SEQ ID NO 264
<211> LENGTH: 6
<212> TYPE: DNA
<213> ORGANISM: Artificial Sequence
<220> FEATURE:
<223> OTHER INFORMATION: k-mer

<400> SEQUENCE: 264 gcgaaa                                                              6

<210> SEQ ID NO 265
<211> LENGTH: 6
<212> TYPE: DNA
<213> ORGANISM: Artificial Sequence
<220> FEATURE:
<223> OTHER INFORMATION: k-mer

<400> SEQUENCE: 265 atacgc                                                              6

<210> SEQ ID NO 266
<211> LENGTH: 6
<212> TYPE: DNA
<213> ORGANISM: Artificial Sequence
<220> FEATURE:
<223> OTHER INFORMATION: k-mer

<400> SEQUENCE: 266 taccga                                                              6

<210> SEQ ID NO 267
<211> LENGTH: 6
<212> TYPE: DNA
<213> ORGANISM: Artificial Sequence
<220> FEATURE:
<223> OTHER INFORMATION: k-mer

<400> SEQUENCE: 267 atgcga                                                              6

<210> SEQ ID NO 268
<211> LENGTH: 6
<212> TYPE: DNA
<213> ORGANISM: Artificial Sequence
<220> FEATURE:
<223> OTHER INFORMATION: k-mer

<400> SEQUENCE: 268 cgtacc                                                              6

<210> SEQ ID NO 269
<211> LENGTH: 6
<212> TYPE: DNA
<213> ORGANISM: Artificial Sequence
<220> FEATURE:
<223> OTHER INFORMATION: k-mer

<400> SEQUENCE: 269 aaagcg                                                              6

<210> SEQ ID NO 270
```

```
<211> LENGTH: 6
<212> TYPE: DNA
<213> ORGANISM: Artificial Sequence
<220> FEATURE:
<223> OTHER INFORMATION: k-mer

<400> SEQUENCE: 270 atgacg                                                                        6

<210> SEQ ID NO 271
<211> LENGTH: 6
<212> TYPE: DNA
<213> ORGANISM: Artificial Sequence
<220> FEATURE:
<223> OTHER INFORMATION: k-mer

<400> SEQUENCE: 271 gtacga                                                                        6

<210> SEQ ID NO 272
<211> LENGTH: 6
<212> TYPE: DNA
<213> ORGANISM: Artificial Sequence
<220> FEATURE:
<223> OTHER INFORMATION: k-mer

<400> SEQUENCE: 272 cgaaaa                                                                        6

<210> SEQ ID NO 273
<211> LENGTH: 6
<212> TYPE: DNA
<213> ORGANISM: Artificial Sequence
<220> FEATURE:
<223> OTHER INFORMATION: k-mer

<400> SEQUENCE: 273 acgata                                                                        6

<210> SEQ ID NO 274
<211> LENGTH: 6
<212> TYPE: DNA
<213> ORGANISM: Artificial Sequence
<220> FEATURE:
<223> OTHER INFORMATION: k-mer

<400> SEQUENCE: 274 cggata                                                                        6

<210> SEQ ID NO 275
<211> LENGTH: 6
<212> TYPE: DNA
<213> ORGANISM: Artificial Sequence
<220> FEATURE:
<223> OTHER INFORMATION: k-mer

<400> SEQUENCE: 275 cggtta                                                                        6

<210> SEQ ID NO 276
<211> LENGTH: 6
<212> TYPE: DNA
<213> ORGANISM: Artificial Sequence
<220> FEATURE:
<223> OTHER INFORMATION: k-mer
```

```
<400> SEQUENCE: 276 agtcga                                                              6

<210> SEQ ID NO 277
<211> LENGTH: 6
<212> TYPE: DNA
<213> ORGANISM: Artificial Sequence
<220> FEATURE:
<223> OTHER INFORMATION: k-mer

<400> SEQUENCE: 277 cgacta                                                              6

<210> SEQ ID NO 278
<211> LENGTH: 6
<212> TYPE: DNA
<213> ORGANISM: Artificial Sequence
<220> FEATURE:
<223> OTHER INFORMATION: k-mer

<400> SEQUENCE: 278 cgcata                                                              6

<210> SEQ ID NO 279
<211> LENGTH: 6
<212> TYPE: DNA
<213> ORGANISM: Artificial Sequence
<220> FEATURE:
<223> OTHER INFORMATION: k-mer

<400> SEQUENCE: 279 acgcaa                                                              6

<210> SEQ ID NO 280
<211> LENGTH: 6
<212> TYPE: DNA
<213> ORGANISM: Artificial Sequence
<220> FEATURE:
<223> OTHER INFORMATION: k-mer

<400> SEQUENCE: 280 atagcg                                                              6

<210> SEQ ID NO 281
<211> LENGTH: 6
<212> TYPE: DNA
<213> ORGANISM: Artificial Sequence
<220> FEATURE:
<223> OTHER INFORMATION: k-mer

<400> SEQUENCE: 281 gacgaa                                                              6

<210> SEQ ID NO 282
<211> LENGTH: 6
<212> TYPE: DNA
<213> ORGANISM: Artificial Sequence
<220> FEATURE:
<223> OTHER INFORMATION: k-mer

<400> SEQUENCE: 282 aacggt                                                              6

<210> SEQ ID NO 283
```

```
<211> LENGTH: 6
<212> TYPE: DNA
<213> ORGANISM: Artificial Sequence
<220> FEATURE:
<223> OTHER INFORMATION: k-mer

<400> SEQUENCE: 283 acaacg                                                                          6

<210> SEQ ID NO 284
<211> LENGTH: 6
<212> TYPE: DNA
<213> ORGANISM: Artificial Sequence
<220> FEATURE:
<223> OTHER INFORMATION: k-mer

<400> SEQUENCE: 284 cgatag                                                                          6

<210> SEQ ID NO 285
<211> LENGTH: 6
<212> TYPE: DNA
<213> ORGANISM: Artificial Sequence
<220> FEATURE:
<223> OTHER INFORMATION: k-mer

<400> SEQUENCE: 285 acatcg                                                                          6

<210> SEQ ID NO 286
<211> LENGTH: 6
<212> TYPE: DNA
<213> ORGANISM: Artificial Sequence
<220> FEATURE:
<223> OTHER INFORMATION: k-mer

<400> SEQUENCE: 286 acgatg                                                                          6

<210> SEQ ID NO 287
<211> LENGTH: 7
<212> TYPE: DNA
<213> ORGANISM: Artificial Sequence
<220> FEATURE:
<223> OTHER INFORMATION: k-mer

<400> SEQUENCE: 287 cgtcgac                                                                         7

<210> SEQ ID NO 288
<211> LENGTH: 7
<212> TYPE: DNA
<213> ORGANISM: Artificial Sequence
<220> FEATURE:
<223> OTHER INFORMATION: k-mer

<400> SEQUENCE: 288 cgacgac                                                                         7

<210> SEQ ID NO 289
<211> LENGTH: 7
<212> TYPE: DNA
<213> ORGANISM: Artificial Sequence
<220> FEATURE:
<223> OTHER INFORMATION: k-mer
```

-continued

```
<400> SEQUENCE: 289 cgcgacg                                                              7

<210> SEQ ID NO 290
<211> LENGTH: 7
<212> TYPE: DNA
<213> ORGANISM: Artificial Sequence
<220> FEATURE:
<223> OTHER INFORMATION: k-mer

<400> SEQUENCE: 290 cgacgcg                                                              7

<210> SEQ ID NO 291
<211> LENGTH: 7
<212> TYPE: DNA
<213> ORGANISM: Artificial Sequence
<220> FEATURE:
<223> OTHER INFORMATION: k-mer

<400> SEQUENCE: 291 gcgtcga                                                              7

<210> SEQ ID NO 292
<211> LENGTH: 7
<212> TYPE: DNA
<213> ORGANISM: Artificial Sequence
<220> FEATURE:
<223> OTHER INFORMATION: k-mer

<400> SEQUENCE: 292 tcgacga                                                              7

<210> SEQ ID NO 293
<211> LENGTH: 7
<212> TYPE: DNA
<213> ORGANISM: Artificial Sequence
<220> FEATURE:
<223> OTHER INFORMATION: k-mer

<400> SEQUENCE: 293 cgcgcga                                                              7

<210> SEQ ID NO 294
<211> LENGTH: 7
<212> TYPE: DNA
<213> ORGANISM: Artificial Sequence
<220> FEATURE:
<223> OTHER INFORMATION: k-mer

<400> SEQUENCE: 294 cgtcgtc                                                              7

<210> SEQ ID NO 295
<211> LENGTH: 7
<212> TYPE: DNA
<213> ORGANISM: Artificial Sequence
<220> FEATURE:
<223> OTHER INFORMATION: k-mer

<400> SEQUENCE: 295 gcgacga                                                              7

<210> SEQ ID NO 296
```

```
<211> LENGTH: 7
<212> TYPE: DNA
<213> ORGANISM: Artificial Sequence
<220> FEATURE:
<223> OTHER INFORMATION: k-mer

<400> SEQUENCE: 296 ccgtcga                                                                 7

<210> SEQ ID NO 297
<211> LENGTH: 7
<212> TYPE: DNA
<213> ORGANISM: Artificial Sequence
<220> FEATURE:
<223> OTHER INFORMATION: k-mer

<400> SEQUENCE: 297 atcgtcg                                                                 7

<210> SEQ ID NO 298
<211> LENGTH: 7
<212> TYPE: DNA
<213> ORGANISM: Artificial Sequence
<220> FEATURE:
<223> OTHER INFORMATION: k-mer

<400> SEQUENCE: 298 atcgacg                                                                 7

<210> SEQ ID NO 299
<211> LENGTH: 7
<212> TYPE: DNA
<213> ORGANISM: Artificial Sequence
<220> FEATURE:
<223> OTHER INFORMATION: k-mer

<400> SEQUENCE: 299 cggtcga                                                                 7

<210> SEQ ID NO 300
<211> LENGTH: 7
<212> TYPE: DNA
<213> ORGANISM: Artificial Sequence
<220> FEATURE:
<223> OTHER INFORMATION: k-mer

<400> SEQUENCE: 300 cgtcgag                                                                 7

<210> SEQ ID NO 301
<211> LENGTH: 7
<212> TYPE: DNA
<213> ORGANISM: Artificial Sequence
<220> FEATURE:
<223> OTHER INFORMATION: k-mer

<400> SEQUENCE: 301 cgcgcaa                                                                 7

<210> SEQ ID NO 302
<211> LENGTH: 7
<212> TYPE: DNA
<213> ORGANISM: Artificial Sequence
<220> FEATURE:
<223> OTHER INFORMATION: k-mer
```

-continued

<400> SEQUENCE: 302 atcggcg                                                              7

<210> SEQ ID NO 303
<211> LENGTH: 7
<212> TYPE: DNA
<213> ORGANISM: Artificial Sequence
<220> FEATURE:
<223> OTHER INFORMATION: k-mer

<400> SEQUENCE: 303 acgacga                                                              7

<210> SEQ ID NO 304
<211> LENGTH: 7
<212> TYPE: DNA
<213> ORGANISM: Artificial Sequence
<220> FEATURE:
<223> OTHER INFORMATION: k-mer

<400> SEQUENCE: 304 cgatcga                                                              7

<210> SEQ ID NO 305
<211> LENGTH: 7
<212> TYPE: DNA
<213> ORGANISM: Artificial Sequence
<220> FEATURE:
<223> OTHER INFORMATION: k-mer

<400> SEQUENCE: 305 ccgacga                                                              7

<210> SEQ ID NO 306
<211> LENGTH: 7
<212> TYPE: DNA
<213> ORGANISM: Artificial Sequence
<220> FEATURE:
<223> OTHER INFORMATION: k-mer

<400> SEQUENCE: 306 cgatcgc                                                              7

<210> SEQ ID NO 307
<211> LENGTH: 7
<212> TYPE: DNA
<213> ORGANISM: Artificial Sequence
<220> FEATURE:
<223> OTHER INFORMATION: k-mer

<400> SEQUENCE: 307 atcgccg                                                              7

<210> SEQ ID NO 308
<211> LENGTH: 7
<212> TYPE: DNA
<213> ORGANISM: Artificial Sequence
<220> FEATURE:
<223> OTHER INFORMATION: k-mer

<400> SEQUENCE: 308 cgaccga                                                              7

<210> SEQ ID NO 309

-continued

```
<211> LENGTH: 7
<212> TYPE: DNA
<213> ORGANISM: Artificial Sequence
<220> FEATURE:
<223> OTHER INFORMATION: k-mer

<400> SEQUENCE: 309 acgtcga                                                                    7

<210> SEQ ID NO 310
<211> LENGTH: 7
<212> TYPE: DNA
<213> ORGANISM: Artificial Sequence
<220> FEATURE:
<223> OTHER INFORMATION: k-mer

<400> SEQUENCE: 310 cgacgtc                                                                    7

<210> SEQ ID NO 311
<211> LENGTH: 7
<212> TYPE: DNA
<213> ORGANISM: Artificial Sequence
<220> FEATURE:
<223> OTHER INFORMATION: k-mer

<400> SEQUENCE: 311 acgacgc                                                                    7

<210> SEQ ID NO 312
<211> LENGTH: 7
<212> TYPE: DNA
<213> ORGANISM: Artificial Sequence
<220> FEATURE:
<223> OTHER INFORMATION: k-mer

<400> SEQUENCE: 312 cggtacg                                                                    7

<210> SEQ ID NO 313
<211> LENGTH: 7
<212> TYPE: DNA
<213> ORGANISM: Artificial Sequence
<220> FEATURE:
<223> OTHER INFORMATION: k-mer

<400> SEQUENCE: 313 accgacg                                                                    7

<210> SEQ ID NO 314
<211> LENGTH: 7
<212> TYPE: DNA
<213> ORGANISM: Artificial Sequence
<220> FEATURE:
<223> OTHER INFORMATION: k-mer

<400> SEQUENCE: 314 cgcgata                                                                    7

<210> SEQ ID NO 315
<211> LENGTH: 7
<212> TYPE: DNA
<213> ORGANISM: Artificial Sequence
<220> FEATURE:
<223> OTHER INFORMATION: k-mer
```

-continued

```
<400> SEQUENCE: 315 ccgatcg                                                                  7

<210> SEQ ID NO 316
<211> LENGTH: 7
<212> TYPE: DNA
<213> ORGANISM: Artificial Sequence
<220> FEATURE:
<223> OTHER INFORMATION: k-mer

<400> SEQUENCE: 316 accgtcg                                                                  7

<210> SEQ ID NO 317
<211> LENGTH: 7
<212> TYPE: DNA
<213> ORGANISM: Artificial Sequence
<220> FEATURE:
<223> OTHER INFORMATION: k-mer

<400> SEQUENCE: 317 tcgcgca                                                                  7

<210> SEQ ID NO 318
<211> LENGTH: 7
<212> TYPE: DNA
<213> ORGANISM: Artificial Sequence
<220> FEATURE:
<223> OTHER INFORMATION: k-mer

<400> SEQUENCE: 318 gcgcgta                                                                  7

<210> SEQ ID NO 319
<211> LENGTH: 7
<212> TYPE: DNA
<213> ORGANISM: Artificial Sequence
<220> FEATURE:
<223> OTHER INFORMATION: k-mer

<400> SEQUENCE: 319 cgacgag                                                                  7

<210> SEQ ID NO 320
<211> LENGTH: 7
<212> TYPE: DNA
<213> ORGANISM: Artificial Sequence
<220> FEATURE:
<223> OTHER INFORMATION: k-mer

<400> SEQUENCE: 320 acgcgac                                                                  7

<210> SEQ ID NO 321
<211> LENGTH: 7
<212> TYPE: DNA
<213> ORGANISM: Artificial Sequence
<220> FEATURE:
<223> OTHER INFORMATION: k-mer

<400> SEQUENCE: 321 cgaccgc                                                                  7

<210> SEQ ID NO 322
```

```
<211> LENGTH: 7
<212> TYPE: DNA
<213> ORGANISM: Artificial Sequence
<220> FEATURE:
<223> OTHER INFORMATION: k-mer

<400> SEQUENCE: 322 cgcgaca                                                                    7

<210> SEQ ID NO 323
<211> LENGTH: 7
<212> TYPE: DNA
<213> ORGANISM: Artificial Sequence
<220> FEATURE:
<223> OTHER INFORMATION: k-mer

<400> SEQUENCE: 323 tcgccga                                                                    7

<210> SEQ ID NO 324
<211> LENGTH: 7
<212> TYPE: DNA
<213> ORGANISM: Artificial Sequence
<220> FEATURE:
<223> OTHER INFORMATION: k-mer

<400> SEQUENCE: 324 gtcgcga                                                                    7

<210> SEQ ID NO 325
<211> LENGTH: 7
<212> TYPE: DNA
<213> ORGANISM: Artificial Sequence
<220> FEATURE:
<223> OTHER INFORMATION: k-mer

<400> SEQUENCE: 325 cgcgaaa                                                                    7

<210> SEQ ID NO 326
<211> LENGTH: 7
<212> TYPE: DNA
<213> ORGANISM: Artificial Sequence
<220> FEATURE:
<223> OTHER INFORMATION: k-mer

<400> SEQUENCE: 326 cggcgta                                                                    7

<210> SEQ ID NO 327
<211> LENGTH: 7
<212> TYPE: DNA
<213> ORGANISM: Artificial Sequence
<220> FEATURE:
<223> OTHER INFORMATION: k-mer

<400> SEQUENCE: 327 gacgcgc                                                                    7

<210> SEQ ID NO 328
<211> LENGTH: 7
<212> TYPE: DNA
<213> ORGANISM: Artificial Sequence
<220> FEATURE:
<223> OTHER INFORMATION: k-mer
```

```
-continued

<400> SEQUENCE: 328 gcgccga                                                              7

<210> SEQ ID NO 329
<211> LENGTH: 7
<212> TYPE: DNA
<213> ORGANISM: Artificial Sequence
<220> FEATURE:
<223> OTHER INFORMATION: k-mer

<400> SEQUENCE: 329 cgcaacg                                                              7

<210> SEQ ID NO 330
<211> LENGTH: 7
<212> TYPE: DNA
<213> ORGANISM: Artificial Sequence
<220> FEATURE:
<223> OTHER INFORMATION: k-mer

<400> SEQUENCE: 330 cgcacga                                                              7

<210> SEQ ID NO 331
<211> LENGTH: 7
<212> TYPE: DNA
<213> ORGANISM: Artificial Sequence
<220> FEATURE:
<223> OTHER INFORMATION: k-mer

<400> SEQUENCE: 331 acgaccg                                                              7

<210> SEQ ID NO 332
<211> LENGTH: 7
<212> TYPE: DNA
<213> ORGANISM: Artificial Sequence
<220> FEATURE:
<223> OTHER INFORMATION: k-mer

<400> SEQUENCE: 332 cgcgtaa                                                              7

<210> SEQ ID NO 333
<211> LENGTH: 7
<212> TYPE: DNA
<213> ORGANISM: Artificial Sequence
<220> FEATURE:
<223> OTHER INFORMATION: k-mer

<400> SEQUENCE: 333 cgatacg                                                              7

<210> SEQ ID NO 334
<211> LENGTH: 7
<212> TYPE: DNA
<213> ORGANISM: Artificial Sequence
<220> FEATURE:
<223> OTHER INFORMATION: k-mer

<400> SEQUENCE: 334 acggtcg                                                              7

<210> SEQ ID NO 335
```

```
<211> LENGTH: 7
<212> TYPE: DNA
<213> ORGANISM: Artificial Sequence
<220> FEATURE:
<223> OTHER INFORMATION: k-mer

<400> SEQUENCE: 335 atgcgcg                                                                    7

<210> SEQ ID NO 336
<211> LENGTH: 7
<212> TYPE: DNA
<213> ORGANISM: Artificial Sequence
<220> FEATURE:
<223> OTHER INFORMATION: k-mer

<400> SEQUENCE: 336 cgtcgca                                                                    7

<210> SEQ ID NO 337
<211> LENGTH: 7
<212> TYPE: DNA
<213> ORGANISM: Artificial Sequence
<220> FEATURE:
<223> OTHER INFORMATION: k-mer

<400> SEQUENCE: 337 acgacgg                                                                    7

<210> SEQ ID NO 338
<211> LENGTH: 7
<212> TYPE: DNA
<213> ORGANISM: Artificial Sequence
<220> FEATURE:
<223> OTHER INFORMATION: k-mer

<400> SEQUENCE: 338 acgtcgc                                                                    7

<210> SEQ ID NO 339
<211> LENGTH: 7
<212> TYPE: DNA
<213> ORGANISM: Artificial Sequence
<220> FEATURE:
<223> OTHER INFORMATION: k-mer

<400> SEQUENCE: 339 acgccga                                                                    7

<210> SEQ ID NO 340
<211> LENGTH: 7
<212> TYPE: DNA
<213> ORGANISM: Artificial Sequence
<220> FEATURE:
<223> OTHER INFORMATION: k-mer

<400> SEQUENCE: 340 acgatcg                                                                    7

<210> SEQ ID NO 341
<211> LENGTH: 7
<212> TYPE: DNA
<213> ORGANISM: Artificial Sequence
<220> FEATURE:
<223> OTHER INFORMATION: k-mer
```

```
<400> SEQUENCE: 341 acggcga                                                              7

<210> SEQ ID NO 342
<211> LENGTH: 7
<212> TYPE: DNA
<213> ORGANISM: Artificial Sequence
<220> FEATURE:
<223> OTHER INFORMATION: k-mer

<400> SEQUENCE: 342 cgccgta                                                              7

<210> SEQ ID NO 343
<211> LENGTH: 7
<212> TYPE: DNA
<213> ORGANISM: Artificial Sequence
<220> FEATURE:
<223> OTHER INFORMATION: k-mer

<400> SEQUENCE: 343 cgacgaa                                                              7

<210> SEQ ID NO 344
<211> LENGTH: 7
<212> TYPE: DNA
<213> ORGANISM: Artificial Sequence
<220> FEATURE:
<223> OTHER INFORMATION: k-mer

<400> SEQUENCE: 344 atcgcga                                                              7

<210> SEQ ID NO 345
<211> LENGTH: 7
<212> TYPE: DNA
<213> ORGANISM: Artificial Sequence
<220> FEATURE:
<223> OTHER INFORMATION: k-mer

<400> SEQUENCE: 345 cgacgca                                                              7

<210> SEQ ID NO 346
<211> LENGTH: 7
<212> TYPE: DNA
<213> ORGANISM: Artificial Sequence
<220> FEATURE:
<223> OTHER INFORMATION: k-mer

<400> SEQUENCE: 346 gcgcgaa                                                              7

<210> SEQ ID NO 347
<211> LENGTH: 7
<212> TYPE: DNA
<213> ORGANISM: Artificial Sequence
<220> FEATURE:
<223> OTHER INFORMATION: k-mer

<400> SEQUENCE: 347 cgaaccg                                                              7

<210> SEQ ID NO 348
```

```
<211> LENGTH: 7
<212> TYPE: DNA
<213> ORGANISM: Artificial Sequence
<220> FEATURE:
<223> OTHER INFORMATION: k-mer

<400> SEQUENCE: 348 cgtcgta                                                                    7

<210> SEQ ID NO 349
<211> LENGTH: 7
<212> TYPE: DNA
<213> ORGANISM: Artificial Sequence
<220> FEATURE:
<223> OTHER INFORMATION: k-mer

<400> SEQUENCE: 349 cgacacg                                                                    7

<210> SEQ ID NO 350
<211> LENGTH: 7
<212> TYPE: DNA
<213> ORGANISM: Artificial Sequence
<220> FEATURE:
<223> OTHER INFORMATION: k-mer

<400> SEQUENCE: 350 agcgtcg                                                                    7

<210> SEQ ID NO 351
<211> LENGTH: 7
<212> TYPE: DNA
<213> ORGANISM: Artificial Sequence
<220> FEATURE:
<223> OTHER INFORMATION: k-mer

<400> SEQUENCE: 351 cgatgcg                                                                    7

<210> SEQ ID NO 352
<211> LENGTH: 7
<212> TYPE: DNA
<213> ORGANISM: Artificial Sequence
<220> FEATURE:
<223> OTHER INFORMATION: k-mer

<400> SEQUENCE: 352 cgctacg                                                                    7

<210> SEQ ID NO 353
<211> LENGTH: 7
<212> TYPE: DNA
<213> ORGANISM: Artificial Sequence
<220> FEATURE:
<223> OTHER INFORMATION: k-mer

<400> SEQUENCE: 353 cgccgaa                                                                    7

<210> SEQ ID NO 354
<211> LENGTH: 7
<212> TYPE: DNA
<213> ORGANISM: Artificial Sequence
<220> FEATURE:
<223> OTHER INFORMATION: k-mer
```

```
<400> SEQUENCE: 354 tacgcga                                                             7

<210> SEQ ID NO 355
<211> LENGTH: 7
<212> TYPE: DNA
<213> ORGANISM: Artificial Sequence
<220> FEATURE:
<223> OTHER INFORMATION: k-mer

<400> SEQUENCE: 355 aacgcgc                                                             7

<210> SEQ ID NO 356
<211> LENGTH: 7
<212> TYPE: DNA
<213> ORGANISM: Artificial Sequence
<220> FEATURE:
<223> OTHER INFORMATION: k-mer

<400> SEQUENCE: 356 attcgcg                                                             7

<210> SEQ ID NO 357
<211> LENGTH: 7
<212> TYPE: DNA
<213> ORGANISM: Artificial Sequence
<220> FEATURE:
<223> OTHER INFORMATION: k-mer

<400> SEQUENCE: 357 cgcgtac                                                             7

<210> SEQ ID NO 358
<211> LENGTH: 7
<212> TYPE: DNA
<213> ORGANISM: Artificial Sequence
<220> FEATURE:
<223> OTHER INFORMATION: k-mer

<400> SEQUENCE: 358 aacggcg                                                             7

<210> SEQ ID NO 359
<211> LENGTH: 7
<212> TYPE: DNA
<213> ORGANISM: Artificial Sequence
<220> FEATURE:
<223> OTHER INFORMATION: k-mer

<400> SEQUENCE: 359 acgcgct                                                             7

<210> SEQ ID NO 360
<211> LENGTH: 7
<212> TYPE: DNA
<213> ORGANISM: Artificial Sequence
<220> FEATURE:
<223> OTHER INFORMATION: k-mer

<400> SEQUENCE: 360 cacgacg                                                             7

<210> SEQ ID NO 361
```

```
<211> LENGTH: 7
<212> TYPE: DNA
<213> ORGANISM: Artificial Sequence
<220> FEATURE:
<223> OTHER INFORMATION: k-mer

<400> SEQUENCE: 361 tcgcgaa                                                                  7

<210> SEQ ID NO 362
<211> LENGTH: 7
<212> TYPE: DNA
<213> ORGANISM: Artificial Sequence
<220> FEATURE:
<223> OTHER INFORMATION: k-mer

<400> SEQUENCE: 362 cgtcgaa                                                                  7

<210> SEQ ID NO 363
<211> LENGTH: 7
<212> TYPE: DNA
<213> ORGANISM: Artificial Sequence
<220> FEATURE:
<223> OTHER INFORMATION: k-mer

<400> SEQUENCE: 363 cgctcga                                                                  7

<210> SEQ ID NO 364
<211> LENGTH: 7
<212> TYPE: DNA
<213> ORGANISM: Artificial Sequence
<220> FEATURE:
<223> OTHER INFORMATION: k-mer

<400> SEQUENCE: 364 acgcgca                                                                  7

<210> SEQ ID NO 365
<211> LENGTH: 7
<212> TYPE: DNA
<213> ORGANISM: Artificial Sequence
<220> FEATURE:
<223> OTHER INFORMATION: k-mer

<400> SEQUENCE: 365 cgtacgc                                                                  7

<210> SEQ ID NO 366
<211> LENGTH: 7
<212> TYPE: DNA
<213> ORGANISM: Artificial Sequence
<220> FEATURE:
<223> OTHER INFORMATION: k-mer

<400> SEQUENCE: 366 catcgcg                                                                  7

<210> SEQ ID NO 367
<211> LENGTH: 7
<212> TYPE: DNA
<213> ORGANISM: Artificial Sequence
<220> FEATURE:
<223> OTHER INFORMATION: k-mer
```

```
<400> SEQUENCE: 367 cgtgcga                                                              7

<210> SEQ ID NO 368
<211> LENGTH: 7
<212> TYPE: DNA
<213> ORGANISM: Artificial Sequence
<220> FEATURE:
<223> OTHER INFORMATION: k-mer

<400> SEQUENCE: 368 cgaatcg                                                              7

<210> SEQ ID NO 369
<211> LENGTH: 7
<212> TYPE: DNA
<213> ORGANISM: Artificial Sequence
<220> FEATURE:
<223> OTHER INFORMATION: k-mer

<400> SEQUENCE: 369 cgactcg                                                              7

<210> SEQ ID NO 370
<211> LENGTH: 7
<212> TYPE: DNA
<213> ORGANISM: Artificial Sequence
<220> FEATURE:
<223> OTHER INFORMATION: k-mer

<400> SEQUENCE: 370 aatcgcg                                                              7

<210> SEQ ID NO 371
<211> LENGTH: 7
<212> TYPE: DNA
<213> ORGANISM: Artificial Sequence
<220> FEATURE:
<223> OTHER INFORMATION: k-mer

<400> SEQUENCE: 371 caacgcg                                                              7

<210> SEQ ID NO 372
<211> LENGTH: 7
<212> TYPE: DNA
<213> ORGANISM: Artificial Sequence
<220> FEATURE:
<223> OTHER INFORMATION: k-mer

<400> SEQUENCE: 372 acgagcg                                                              7

<210> SEQ ID NO 373
<211> LENGTH: 7
<212> TYPE: DNA
<213> ORGANISM: Artificial Sequence
<220> FEATURE:
<223> OTHER INFORMATION: k-mer

<400> SEQUENCE: 373 atacgcg                                                              7

<210> SEQ ID NO 374
```

```
<211> LENGTH: 7
<212> TYPE: DNA
<213> ORGANISM: Artificial Sequence
<220> FEATURE:
<223> OTHER INFORMATION: k-mer

<400> SEQUENCE: 374 aacgacg                                                                    7

<210> SEQ ID NO 375
<211> LENGTH: 7
<212> TYPE: DNA
<213> ORGANISM: Artificial Sequence
<220> FEATURE:
<223> OTHER INFORMATION: k-mer

<400> SEQUENCE: 375 aagcgcg                                                                    7

<210> SEQ ID NO 376
<211> LENGTH: 7
<212> TYPE: DNA
<213> ORGANISM: Artificial Sequence
<220> FEATURE:
<223> OTHER INFORMATION: k-mer

<400> SEQUENCE: 376 acgccgt                                                                    7

<210> SEQ ID NO 377
<211> LENGTH: 7
<212> TYPE: DNA
<213> ORGANISM: Artificial Sequence
<220> FEATURE:
<223> OTHER INFORMATION: k-mer

<400> SEQUENCE: 377 cacgtcg                                                                    7

<210> SEQ ID NO 378
<211> LENGTH: 7
<212> TYPE: DNA
<213> ORGANISM: Artificial Sequence
<220> FEATURE:
<223> OTHER INFORMATION: k-mer

<400> SEQUENCE: 378 atcgcgg                                                                    7

<210> SEQ ID NO 379
<211> LENGTH: 7
<212> TYPE: DNA
<213> ORGANISM: Artificial Sequence
<220> FEATURE:
<223> OTHER INFORMATION: k-mer

<400> SEQUENCE: 379 aacgtcg                                                                    7

<210> SEQ ID NO 380
<211> LENGTH: 7
<212> TYPE: DNA
<213> ORGANISM: Artificial Sequence
<220> FEATURE:
<223> OTHER INFORMATION: k-mer
```

```
<400> SEQUENCE: 380 cgtaacg                                                              7

<210> SEQ ID NO 381
<211> LENGTH: 7
<212> TYPE: DNA
<213> ORGANISM: Artificial Sequence
<220> FEATURE:
<223> OTHER INFORMATION: k-mer

<400> SEQUENCE: 381 cgcggta                                                              7

<210> SEQ ID NO 382
<211> LENGTH: 7
<212> TYPE: DNA
<213> ORGANISM: Artificial Sequence
<220> FEATURE:
<223> OTHER INFORMATION: k-mer

<400> SEQUENCE: 382 agcgcga                                                              7

<210> SEQ ID NO 383
<211> LENGTH: 7
<212> TYPE: DNA
<213> ORGANISM: Artificial Sequence
<220> FEATURE:
<223> OTHER INFORMATION: k-mer

<400> SEQUENCE: 383 gacgcga                                                              7

<210> SEQ ID NO 384
<211> LENGTH: 7
<212> TYPE: DNA
<213> ORGANISM: Artificial Sequence
<220> FEATURE:
<223> OTHER INFORMATION: k-mer

<400> SEQUENCE: 384 acgacgt                                                              7

<210> SEQ ID NO 385
<211> LENGTH: 7
<212> TYPE: DNA
<213> ORGANISM: Artificial Sequence
<220> FEATURE:
<223> OTHER INFORMATION: k-mer

<400> SEQUENCE: 385 cgacgta                                                              7

<210> SEQ ID NO 386
<211> LENGTH: 7
<212> TYPE: DNA
<213> ORGANISM: Artificial Sequence
<220> FEATURE:
<223> OTHER INFORMATION: k-mer

<400> SEQUENCE: 386 acgcgtc                                                              7

<210> SEQ ID NO 387
```

```
<211> LENGTH: 6
<212> TYPE: DNA
<213> ORGANISM: Artificial Sequence
<220> FEATURE:
<223> OTHER INFORMATION: k-mer

<400> SEQUENCE: 387 cgtcga                                                                     6

<210> SEQ ID NO 388
<211> LENGTH: 6
<212> TYPE: DNA
<213> ORGANISM: Artificial Sequence
<220> FEATURE:
<223> OTHER INFORMATION: k-mer

<400> SEQUENCE: 388 cgacga                                                                     6

<210> SEQ ID NO 389
<211> LENGTH: 6
<212> TYPE: DNA
<213> ORGANISM: Artificial Sequence
<220> FEATURE:
<223> OTHER INFORMATION: k-mer

<400> SEQUENCE: 389 cgatcg                                                                     6

<210> SEQ ID NO 390
<211> LENGTH: 6
<212> TYPE: DNA
<213> ORGANISM: Artificial Sequence
<220> FEATURE:
<223> OTHER INFORMATION: k-mer

<400> SEQUENCE: 390 cggcga                                                                     6

<210> SEQ ID NO 391
<211> LENGTH: 6
<212> TYPE: DNA
<213> ORGANISM: Artificial Sequence
<220> FEATURE:
<223> OTHER INFORMATION: k-mer

<400> SEQUENCE: 391 cgccga                                                                     6

<210> SEQ ID NO 392
<211> LENGTH: 6
<212> TYPE: DNA
<213> ORGANISM: Artificial Sequence
<220> FEATURE:
<223> OTHER INFORMATION: k-mer

<400> SEQUENCE: 392 cgcgaa                                                                     6

<210> SEQ ID NO 393
<211> LENGTH: 6
<212> TYPE: DNA
<213> ORGANISM: Artificial Sequence
<220> FEATURE:
<223> OTHER INFORMATION: k-mer
```

```
<400> SEQUENCE: 393 cgaccg                                                                   6

<210> SEQ ID NO 394
<211> LENGTH: 6
<212> TYPE: DNA
<213> ORGANISM: Artificial Sequence
<220> FEATURE:
<223> OTHER INFORMATION: k-mer

<400> SEQUENCE: 394 cgaacg                                                                   6

<210> SEQ ID NO 395
<211> LENGTH: 6
<212> TYPE: DNA
<213> ORGANISM: Artificial Sequence
<220> FEATURE:
<223> OTHER INFORMATION: k-mer

<400> SEQUENCE: 395 tcgcga                                                                   6

<210> SEQ ID NO 396
<211> LENGTH: 6
<212> TYPE: DNA
<213> ORGANISM: Artificial Sequence
<220> FEATURE:
<223> OTHER INFORMATION: k-mer

<400> SEQUENCE: 396 acgacg                                                                   6

<210> SEQ ID NO 397
<211> LENGTH: 6
<212> TYPE: DNA
<213> ORGANISM: Artificial Sequence
<220> FEATURE:
<223> OTHER INFORMATION: k-mer

<400> SEQUENCE: 397 ccgtcg                                                                   6

<210> SEQ ID NO 398
<211> LENGTH: 6
<212> TYPE: DNA
<213> ORGANISM: Artificial Sequence
<220> FEATURE:
<223> OTHER INFORMATION: k-mer

<400> SEQUENCE: 398 cgtcgc                                                                   6

<210> SEQ ID NO 399
<211> LENGTH: 6
<212> TYPE: DNA
<213> ORGANISM: Artificial Sequence
<220> FEATURE:
<223> OTHER INFORMATION: k-mer

<400> SEQUENCE: 399 cgacgc                                                                   6

<210> SEQ ID NO 400
```

```
<211> LENGTH: 6
<212> TYPE: DNA
<213> ORGANISM: Artificial Sequence
<220> FEATURE:
<223> OTHER INFORMATION: k-mer

<400> SEQUENCE: 400 acgccg                                                                    6

<210> SEQ ID NO 401
<211> LENGTH: 6
<212> TYPE: DNA
<213> ORGANISM: Artificial Sequence
<220> FEATURE:
<223> OTHER INFORMATION: k-mer

<400> SEQUENCE: 401 acggcg                                                                    6

<210> SEQ ID NO 402
<211> LENGTH: 6
<212> TYPE: DNA
<213> ORGANISM: Artificial Sequence
<220> FEATURE:
<223> OTHER INFORMATION: k-mer

<400> SEQUENCE: 402 cgcgac                                                                    6

<210> SEQ ID NO 403
<211> LENGTH: 6
<212> TYPE: DNA
<213> ORGANISM: Artificial Sequence
<220> FEATURE:
<223> OTHER INFORMATION: k-mer

<400> SEQUENCE: 403 ccgacg                                                                    6

<210> SEQ ID NO 404
<211> LENGTH: 6
<212> TYPE: DNA
<213> ORGANISM: Artificial Sequence
<220> FEATURE:
<223> OTHER INFORMATION: k-mer

<400> SEQUENCE: 404 cgcgta                                                                    6

<210> SEQ ID NO 405
<211> LENGTH: 6
<212> TYPE: DNA
<213> ORGANISM: Artificial Sequence
<220> FEATURE:
<223> OTHER INFORMATION: k-mer

<400> SEQUENCE: 405 acgtcg                                                                    6

<210> SEQ ID NO 406
<211> LENGTH: 6
<212> TYPE: DNA
<213> ORGANISM: Artificial Sequence
<220> FEATURE:
<223> OTHER INFORMATION: k-mer
```

-continued

```
<400> SEQUENCE: 406 aacgcg                                                                    6

<210> SEQ ID NO 407
<211> LENGTH: 6
<212> TYPE: DNA
<213> ORGANISM: Artificial Sequence
<220> FEATURE:
<223> OTHER INFORMATION: k-mer

<400> SEQUENCE: 407 ccgcga                                                                    6

<210> SEQ ID NO 408
<211> LENGTH: 6
<212> TYPE: DNA
<213> ORGANISM: Artificial Sequence
<220> FEATURE:
<223> OTHER INFORMATION: k-mer

<400> SEQUENCE: 408 acgcga                                                                    6

<210> SEQ ID NO 409
<211> LENGTH: 6
<212> TYPE: DNA
<213> ORGANISM: Artificial Sequence
<220> FEATURE:
<223> OTHER INFORMATION: k-mer

<400> SEQUENCE: 409 atcggc                                                                    6

<210> SEQ ID NO 410
<211> LENGTH: 6
<212> TYPE: DNA
<213> ORGANISM: Artificial Sequence
<220> FEATURE:
<223> OTHER INFORMATION: k-mer

<400> SEQUENCE: 410 cgagcg                                                                    6

<210> SEQ ID NO 411
<211> LENGTH: 6
<212> TYPE: DNA
<213> ORGANISM: Artificial Sequence
<220> FEATURE:
<223> OTHER INFORMATION: k-mer

<400> SEQUENCE: 411 ccggcg                                                                    6

<210> SEQ ID NO 412
<211> LENGTH: 6
<212> TYPE: DNA
<213> ORGANISM: Artificial Sequence
<220> FEATURE:
<223> OTHER INFORMATION: k-mer

<400> SEQUENCE: 412 cgtacg                                                                    6

<210> SEQ ID NO 413
```

```
<211> LENGTH: 6
<212> TYPE: DNA
<213> ORGANISM: Artificial Sequence
<220> FEATURE:
<223> OTHER INFORMATION: k-mer

<400> SEQUENCE: 413 atcgac                                                                     6

<210> SEQ ID NO 414
<211> LENGTH: 6
<212> TYPE: DNA
<213> ORGANISM: Artificial Sequence
<220> FEATURE:
<223> OTHER INFORMATION: k-mer

<400> SEQUENCE: 414 agcgcg                                                                     6

<210> SEQ ID NO 415
<211> LENGTH: 6
<212> TYPE: DNA
<213> ORGANISM: Artificial Sequence
<220> FEATURE:
<223> OTHER INFORMATION: k-mer

<400> SEQUENCE: 415 ccgccg                                                                     6

<210> SEQ ID NO 416
<211> LENGTH: 6
<212> TYPE: DNA
<213> ORGANISM: Artificial Sequence
<220> FEATURE:
<223> OTHER INFORMATION: k-mer

<400> SEQUENCE: 416 cgcgga                                                                     6

<210> SEQ ID NO 417
<211> LENGTH: 6
<212> TYPE: DNA
<213> ORGANISM: Artificial Sequence
<220> FEATURE:
<223> OTHER INFORMATION: k-mer

<400> SEQUENCE: 417 atcgcc                                                                     6

<210> SEQ ID NO 418
<211> LENGTH: 6
<212> TYPE: DNA
<213> ORGANISM: Artificial Sequence
<220> FEATURE:
<223> OTHER INFORMATION: k-mer

<400> SEQUENCE: 418 cggcgc                                                                     6

<210> SEQ ID NO 419
<211> LENGTH: 6
<212> TYPE: DNA
<213> ORGANISM: Artificial Sequence
<220> FEATURE:
<223> OTHER INFORMATION: k-mer
```

```
<400> SEQUENCE: 419 cgccgc                                                              6

<210> SEQ ID NO 420
<211> LENGTH: 6
<212> TYPE: DNA
<213> ORGANISM: Artificial Sequence
<220> FEATURE:
<223> OTHER INFORMATION: k-mer

<400> SEQUENCE: 420 cgcgca                                                              6

<210> SEQ ID NO 421
<211> LENGTH: 6
<212> TYPE: DNA
<213> ORGANISM: Artificial Sequence
<220> FEATURE:
<223> OTHER INFORMATION: k-mer

<400> SEQUENCE: 421 gcgaac                                                              6

<210> SEQ ID NO 422
<211> LENGTH: 6
<212> TYPE: DNA
<213> ORGANISM: Artificial Sequence
<220> FEATURE:
<223> OTHER INFORMATION: k-mer

<400> SEQUENCE: 422 cgcgtc                                                              6

<210> SEQ ID NO 423
<211> LENGTH: 6
<212> TYPE: DNA
<213> ORGANISM: Artificial Sequence
<220> FEATURE:
<223> OTHER INFORMATION: k-mer

<400> SEQUENCE: 423 cggcaa                                                              6

<210> SEQ ID NO 424
<211> LENGTH: 6
<212> TYPE: DNA
<213> ORGANISM: Artificial Sequence
<220> FEATURE:
<223> OTHER INFORMATION: k-mer

<400> SEQUENCE: 424 ccgatc                                                              6

<210> SEQ ID NO 425
<211> LENGTH: 6
<212> TYPE: DNA
<213> ORGANISM: Artificial Sequence
<220> FEATURE:
<223> OTHER INFORMATION: k-mer

<400> SEQUENCE: 425 cggacg                                                              6

<210> SEQ ID NO 426
```

```
<211> LENGTH: 6
<212> TYPE: DNA
<213> ORGANISM: Artificial Sequence
<220> FEATURE:
<223> OTHER INFORMATION: k-mer

<400> SEQUENCE: 426 gccgac                                                                     6

<210> SEQ ID NO 427
<211> LENGTH: 6
<212> TYPE: DNA
<213> ORGANISM: Artificial Sequence
<220> FEATURE:
<223> OTHER INFORMATION: k-mer

<400> SEQUENCE: 427 cgcgag                                                                     6

<210> SEQ ID NO 428
<211> LENGTH: 6
<212> TYPE: DNA
<213> ORGANISM: Artificial Sequence
<220> FEATURE:
<223> OTHER INFORMATION: k-mer

<400> SEQUENCE: 428 acgcgg                                                                     6

<210> SEQ ID NO 429
<211> LENGTH: 6
<212> TYPE: DNA
<213> ORGANISM: Artificial Sequence
<220> FEATURE:
<223> OTHER INFORMATION: k-mer

<400> SEQUENCE: 429 gcggta                                                                     6

<210> SEQ ID NO 430
<211> LENGTH: 6
<212> TYPE: DNA
<213> ORGANISM: Artificial Sequence
<220> FEATURE:
<223> OTHER INFORMATION: k-mer

<400> SEQUENCE: 430 acgcgc                                                                     6

<210> SEQ ID NO 431
<211> LENGTH: 6
<212> TYPE: DNA
<213> ORGANISM: Artificial Sequence
<220> FEATURE:
<223> OTHER INFORMATION: k-mer

<400> SEQUENCE: 431 accggc                                                                     6

<210> SEQ ID NO 432
<211> LENGTH: 6
<212> TYPE: DNA
<213> ORGANISM: Artificial Sequence
<220> FEATURE:
<223> OTHER INFORMATION: k-mer
```

-continued

<400> SEQUENCE: 432 atcgcg                                                                    6

<210> SEQ ID NO 433
<211> LENGTH: 6
<212> TYPE: DNA
<213> ORGANISM: Artificial Sequence
<220> FEATURE:
<223> OTHER INFORMATION: k-mer

<400> SEQUENCE: 433 catcgg                                                                    6

<210> SEQ ID NO 434
<211> LENGTH: 6
<212> TYPE: DNA
<213> ORGANISM: Artificial Sequence
<220> FEATURE:
<223> OTHER INFORMATION: k-mer

<400> SEQUENCE: 434 cgatgc                                                                    6

<210> SEQ ID NO 435
<211> LENGTH: 6
<212> TYPE: DNA
<213> ORGANISM: Artificial Sequence
<220> FEATURE:
<223> OTHER INFORMATION: k-mer

<400> SEQUENCE: 435 atgccg                                                                    6

<210> SEQ ID NO 436
<211> LENGTH: 6
<212> TYPE: DNA
<213> ORGANISM: Artificial Sequence
<220> FEATURE:
<223> OTHER INFORMATION: k-mer

<400> SEQUENCE: 436 tcggca                                                                    6

<210> SEQ ID NO 437
<211> LENGTH: 6
<212> TYPE: DNA
<213> ORGANISM: Artificial Sequence
<220> FEATURE:
<223> OTHER INFORMATION: k-mer

<400> SEQUENCE: 437 gccgaa                                                                    6

<210> SEQ ID NO 438
<211> LENGTH: 6
<212> TYPE: DNA
<213> ORGANISM: Artificial Sequence
<220> FEATURE:
<223> OTHER INFORMATION: k-mer

<400> SEQUENCE: 438 cgcggc                                                                    6

<210> SEQ ID NO 439

```
<211> LENGTH: 6
<212> TYPE: DNA
<213> ORGANISM: Artificial Sequence
<220> FEATURE:
<223> OTHER INFORMATION: k-mer

<400> SEQUENCE: 439 cgatga                                                                   6

<210> SEQ ID NO 440
<211> LENGTH: 6
<212> TYPE: DNA
<213> ORGANISM: Artificial Sequence
<220> FEATURE:
<223> OTHER INFORMATION: k-mer

<400> SEQUENCE: 440 atcgtc                                                                   6

<210> SEQ ID NO 441
<211> LENGTH: 6
<212> TYPE: DNA
<213> ORGANISM: Artificial Sequence
<220> FEATURE:
<223> OTHER INFORMATION: k-mer

<400> SEQUENCE: 441 accgac                                                                   6

<210> SEQ ID NO 442
<211> LENGTH: 6
<212> TYPE: DNA
<213> ORGANISM: Artificial Sequence
<220> FEATURE:
<223> OTHER INFORMATION: k-mer

<400> SEQUENCE: 442 ccgaac                                                                   6

<210> SEQ ID NO 443
<211> LENGTH: 6
<212> TYPE: DNA
<213> ORGANISM: Artificial Sequence
<220> FEATURE:
<223> OTHER INFORMATION: k-mer

<400> SEQUENCE: 443 accgcc                                                                   6

<210> SEQ ID NO 444
<211> LENGTH: 6
<212> TYPE: DNA
<213> ORGANISM: Artificial Sequence
<220> FEATURE:
<223> OTHER INFORMATION: k-mer

<400> SEQUENCE: 444 gtcgaa                                                                   6

<210> SEQ ID NO 445
<211> LENGTH: 6
<212> TYPE: DNA
<213> ORGANISM: Artificial Sequence
<220> FEATURE:
<223> OTHER INFORMATION: k-mer
```

```
<400> SEQUENCE: 445 gcgacc                                                              6

<210> SEQ ID NO 446
<211> LENGTH: 6
<212> TYPE: DNA
<213> ORGANISM: Artificial Sequence
<220> FEATURE:
<223> OTHER INFORMATION: k-mer

<400> SEQUENCE: 446 accgat                                                              6

<210> SEQ ID NO 447
<211> LENGTH: 6
<212> TYPE: DNA
<213> ORGANISM: Artificial Sequence
<220> FEATURE:
<223> OTHER INFORMATION: k-mer

<400> SEQUENCE: 447 aacggc                                                              6

<210> SEQ ID NO 448
<211> LENGTH: 6
<212> TYPE: DNA
<213> ORGANISM: Artificial Sequence
<220> FEATURE:
<223> OTHER INFORMATION: k-mer

<400> SEQUENCE: 448 catcga                                                              6

<210> SEQ ID NO 449
<211> LENGTH: 6
<212> TYPE: DNA
<213> ORGANISM: Artificial Sequence
<220> FEATURE:
<223> OTHER INFORMATION: k-mer

<400> SEQUENCE: 449 catcgc                                                              6

<210> SEQ ID NO 450
<211> LENGTH: 6
<212> TYPE: DNA
<213> ORGANISM: Artificial Sequence
<220> FEATURE:
<223> OTHER INFORMATION: k-mer

<400> SEQUENCE: 450 gccgta                                                              6

<210> SEQ ID NO 451
<211> LENGTH: 6
<212> TYPE: DNA
<213> ORGANISM: Artificial Sequence
<220> FEATURE:
<223> OTHER INFORMATION: k-mer

<400> SEQUENCE: 451 gacgac                                                              6

<210> SEQ ID NO 452
```

```
<211> LENGTH: 6
<212> TYPE: DNA
<213> ORGANISM: Artificial Sequence
<220> FEATURE:
<223> OTHER INFORMATION: k-mer

<400> SEQUENCE: 452 cgatac                                                                    6

<210> SEQ ID NO 453
<211> LENGTH: 6
<212> TYPE: DNA
<213> ORGANISM: Artificial Sequence
<220> FEATURE:
<223> OTHER INFORMATION: k-mer

<400> SEQUENCE: 453 cgccaa                                                                    6

<210> SEQ ID NO 454
<211> LENGTH: 6
<212> TYPE: DNA
<213> ORGANISM: Artificial Sequence
<220> FEATURE:
<223> OTHER INFORMATION: k-mer

<400> SEQUENCE: 454 gtcgac                                                                    6

<210> SEQ ID NO 455
<211> LENGTH: 6
<212> TYPE: DNA
<213> ORGANISM: Artificial Sequence
<220> FEATURE:
<223> OTHER INFORMATION: k-mer

<400> SEQUENCE: 455 ccgata                                                                    6

<210> SEQ ID NO 456
<211> LENGTH: 6
<212> TYPE: DNA
<213> ORGANISM: Artificial Sequence
<220> FEATURE:
<223> OTHER INFORMATION: k-mer

<400> SEQUENCE: 456 gaccgc                                                                    6

<210> SEQ ID NO 457
<211> LENGTH: 6
<212> TYPE: DNA
<213> ORGANISM: Artificial Sequence
<220> FEATURE:
<223> OTHER INFORMATION: k-mer

<400> SEQUENCE: 457 ggtcga                                                                    6

<210> SEQ ID NO 458
<211> LENGTH: 6
<212> TYPE: DNA
<213> ORGANISM: Artificial Sequence
<220> FEATURE:
<223> OTHER INFORMATION: k-mer
```

```
-continued

<400> SEQUENCE: 458 cgatca                                                              6

<210> SEQ ID NO 459
<211> LENGTH: 6
<212> TYPE: DNA
<213> ORGANISM: Artificial Sequence
<220> FEATURE:
<223> OTHER INFORMATION: k-mer

<400> SEQUENCE: 459 cgcatc                                                              6

<210> SEQ ID NO 460
<211> LENGTH: 6
<212> TYPE: DNA
<213> ORGANISM: Artificial Sequence
<220> FEATURE:
<223> OTHER INFORMATION: k-mer

<400> SEQUENCE: 460 cgacca                                                              6

<210> SEQ ID NO 461
<211> LENGTH: 6
<212> TYPE: DNA
<213> ORGANISM: Artificial Sequence
<220> FEATURE:
<223> OTHER INFORMATION: k-mer

<400> SEQUENCE: 461 gacggc                                                              6

<210> SEQ ID NO 462
<211> LENGTH: 6
<212> TYPE: DNA
<213> ORGANISM: Artificial Sequence
<220> FEATURE:
<223> OTHER INFORMATION: k-mer

<400> SEQUENCE: 462 accggt                                                              6

<210> SEQ ID NO 463
<211> LENGTH: 6
<212> TYPE: DNA
<213> ORGANISM: Artificial Sequence
<220> FEATURE:
<223> OTHER INFORMATION: k-mer

<400> SEQUENCE: 463 atccgg                                                              6

<210> SEQ ID NO 464
<211> LENGTH: 6
<212> TYPE: DNA
<213> ORGANISM: Artificial Sequence
<220> FEATURE:
<223> OTHER INFORMATION: k-mer

<400> SEQUENCE: 464 acgcgt                                                              6

<210> SEQ ID NO 465
```

```
<211> LENGTH: 6
<212> TYPE: DNA
<213> ORGANISM: Artificial Sequence
<220> FEATURE:
<223> OTHER INFORMATION: k-mer

<400> SEQUENCE: 465 aacgcc                                                                   6

<210> SEQ ID NO 466
<211> LENGTH: 6
<212> TYPE: DNA
<213> ORGANISM: Artificial Sequence
<220> FEATURE:
<223> OTHER INFORMATION: k-mer

<400> SEQUENCE: 466 ccggta                                                                   6

<210> SEQ ID NO 467
<211> LENGTH: 6
<212> TYPE: DNA
<213> ORGANISM: Artificial Sequence
<220> FEATURE:
<223> OTHER INFORMATION: k-mer

<400> SEQUENCE: 467 cggtac                                                                   6

<210> SEQ ID NO 468
<211> LENGTH: 6
<212> TYPE: DNA
<213> ORGANISM: Artificial Sequence
<220> FEATURE:
<223> OTHER INFORMATION: k-mer

<400> SEQUENCE: 468 aaccgc                                                                   6

<210> SEQ ID NO 469
<211> LENGTH: 6
<212> TYPE: DNA
<213> ORGANISM: Artificial Sequence
<220> FEATURE:
<223> OTHER INFORMATION: k-mer

<400> SEQUENCE: 469 cgcacg                                                                   6

<210> SEQ ID NO 470
<211> LENGTH: 6
<212> TYPE: DNA
<213> ORGANISM: Artificial Sequence
<220> FEATURE:
<223> OTHER INFORMATION: k-mer

<400> SEQUENCE: 470 gcggca                                                                   6

<210> SEQ ID NO 471
<211> LENGTH: 6
<212> TYPE: DNA
<213> ORGANISM: Artificial Sequence
<220> FEATURE:
<223> OTHER INFORMATION: k-mer
```

```
<400> SEQUENCE: 471 caacgc                                                                  6

<210> SEQ ID NO 472
<211> LENGTH: 6
<212> TYPE: DNA
<213> ORGANISM: Artificial Sequence
<220> FEATURE:
<223> OTHER INFORMATION: k-mer

<400> SEQUENCE: 472 gcgcga                                                                  6

<210> SEQ ID NO 473
<211> LENGTH: 6
<212> TYPE: DNA
<213> ORGANISM: Artificial Sequence
<220> FEATURE:
<223> OTHER INFORMATION: k-mer

<400> SEQUENCE: 473 gcgtac                                                                  6

<210> SEQ ID NO 474
<211> LENGTH: 6
<212> TYPE: DNA
<213> ORGANISM: Artificial Sequence
<220> FEATURE:
<223> OTHER INFORMATION: k-mer

<400> SEQUENCE: 474 cgaacc                                                                  6

<210> SEQ ID NO 475
<211> LENGTH: 6
<212> TYPE: DNA
<213> ORGANISM: Artificial Sequence
<220> FEATURE:
<223> OTHER INFORMATION: k-mer

<400> SEQUENCE: 475 ggcgaa                                                                  6

<210> SEQ ID NO 476
<211> LENGTH: 6
<212> TYPE: DNA
<213> ORGANISM: Artificial Sequence
<220> FEATURE:
<223> OTHER INFORMATION: k-mer

<400> SEQUENCE: 476 gctcga                                                                  6

<210> SEQ ID NO 477
<211> LENGTH: 6
<212> TYPE: DNA
<213> ORGANISM: Artificial Sequence
<220> FEATURE:
<223> OTHER INFORMATION: k-mer

<400> SEQUENCE: 477 acgacc                                                                  6

<210> SEQ ID NO 478
```

```
<211> LENGTH: 6
<212> TYPE: DNA
<213> ORGANISM: Artificial Sequence
<220> FEATURE:
<223> OTHER INFORMATION: k-mer

<400> SEQUENCE: 478 cggtca                                                                    6

<210> SEQ ID NO 479
<211> LENGTH: 6
<212> TYPE: DNA
<213> ORGANISM: Artificial Sequence
<220> FEATURE:
<223> OTHER INFORMATION: k-mer

<400> SEQUENCE: 479 gcgata                                                                    6

<210> SEQ ID NO 480
<211> LENGTH: 6
<212> TYPE: DNA
<213> ORGANISM: Artificial Sequence
<220> FEATURE:
<223> OTHER INFORMATION: k-mer

<400> SEQUENCE: 480 cgcaac                                                                    6

<210> SEQ ID NO 481
<211> LENGTH: 6
<212> TYPE: DNA
<213> ORGANISM: Artificial Sequence
<220> FEATURE:
<223> OTHER INFORMATION: k-mer

<400> SEQUENCE: 481 cgaagc                                                                    6

<210> SEQ ID NO 482
<211> LENGTH: 6
<212> TYPE: DNA
<213> ORGANISM: Artificial Sequence
<220> FEATURE:
<223> OTHER INFORMATION: k-mer

<400> SEQUENCE: 482 gccgga                                                                    6

<210> SEQ ID NO 483
<211> LENGTH: 6
<212> TYPE: DNA
<213> ORGANISM: Artificial Sequence
<220> FEATURE:
<223> OTHER INFORMATION: k-mer

<400> SEQUENCE: 483 gcggaa                                                                    6

<210> SEQ ID NO 484
<211> LENGTH: 6
<212> TYPE: DNA
<213> ORGANISM: Artificial Sequence
<220> FEATURE:
<223> OTHER INFORMATION: k-mer
```

```
<400> SEQUENCE: 484 cgacaa                                                                      6

<210> SEQ ID NO 485
<211> LENGTH: 6
<212> TYPE: DNA
<213> ORGANISM: Artificial Sequence
<220> FEATURE:
<223> OTHER INFORMATION: k-mer

<400> SEQUENCE: 485 cttcgc                                                                      6

<210> SEQ ID NO 486
<211> LENGTH: 6
<212> TYPE: DNA
<213> ORGANISM: Artificial Sequence
<220> FEATURE:
<223> OTHER INFORMATION: k-mer

<400> SEQUENCE: 486 caaccg                                                                      6
```

AMPLIFICATION-INTEGRATED GENETIC MATERIAL DEPLETION OF NON-TARGET ORGANISMS USING DIFFERENTIALLY ABUNDANT K-MERS

CROSS REFERENCE TO RELATED APPLICATIONS

This is a 371 of PCT/EP2017/080666, filed Nov. 28, 2017, which claims priority to European Patent Application No. EP 16205822.6, filed Dec. 21, 2016, which is hereby incorporated by reference herein in its entirety for all purposes.

FIELD

The present invention relates to a method of selectively amplifying at least one nucleic acid sequence of at least one microorganism and/or virus in a sample of a subject, wherein k-mers are applied that show a difference in frequency and/or context in the genome of the at least one microorganism and/or virus compared to the genome of the subject.

BACKGROUND

Infections by bacteria, viruses, or parasites have always been a threat to humans, and will continue to count for a high number of deaths in the world. The most widely used strategies to fight infections are:
a) prevention (e.g. by vaccination) or
b) treatment (e.g. by antibiotics or antiviral agents).

For both these strategies, diagnostic methods that detect ongoing infections (for treatment) or previous infections (to check if immunity by a previous infection or a vaccination is provided) are needed.

Detection of a pathogen infection in a subject can be done in various ways, one of which is the detection of nucleic acid sequences of the pathogen in a sample of the subject.

For this purpose, sequencing of the nucleic acid sequences in the sample can be carried out.

However, when sequencing nucleic acid sequences in a complex sample of a subject, the direct sequencing of such samples like complex biological biospecimen (e.g., blood, urine etc.) for detection of pathogens (e.g., bacteria, viruses, etc.) is often hampered by the high background level of the nucleic acid sequences of the subject itself, e.g., (human) host DNA. Especially for blood, surplus human DNA dominates extractable DNA pools by as much as $10^{10}$. For infectious disease diagnostics, regularly the nucleic acid sequences of the subject, e.g., human DNA, is not of interest. Therefore direct sequencing of highly host-contaminated samples is inefficient and subsequently not cost-effective.

Currently, several techniques for host (e.g., human) DNA removal exist, but these are usually costly and often require additional sample preparation steps.

Some techniques employ a depletion of human DNA by targeting eukaryotic DNA specialties, e.g., the presence of CpG-methylation sites and histones. These techniques involve a subsequent antibody targeting, as e.g., described for the NEBNext® Microbiome DNA Enrichment Kit of New England Biolabs® Inc. (https://www.neb.com/products/e2612-nebnext-microbiome-dna-enrichment-kit#pd-references), or in CN 104152437.

Further, also differences in the cell membrane/wall can be used, leading to a selective lysis approach, as, e.g., obtainable using MolYsis™ of Molzym GmbH & Co. KG (http://www.molzym.com/products/dna-isolation-products/pathogen-dna-molysis), or as disclosed in U.S. Pat. No. 7,893,251.

However, these techniques are not working when the host organism changes and/or the target organisms are closely related organism (eukaryotes), e.g., the human parasites *Plasmodium falciparum*, an organism also showing methylation and histones.

Furthermore, other enrichment techniques like microfluidic multiple displacement amplification (MDA), ultracentrifugation of DNA with histones, and selective lysis of human cells, etc., exist.

Recently, Ge et al., "Preferential Amplification of Pathogenic Sequences", Scientific Reports 5, Article number: 11047, (2015), doi:10.1038/srep11047 proposed a strategy primarily designed for transcriptomes where viral transcripts are to be expected. The principle is based on 8, 9 or 10 mers not matching the 2000 most abundant human transcripts. These "non-human" primers were subsequently used in a reverse transcription reaction to produce cDNA libraries from RNA material.

However, a need exists for a further improvement for methods of enriching nucleic acid sequences of microorganisms and/or viruses in a sample of a subject.

SUMMARY OF THE INVENTION

The inventors found that a further improvement in nucleic acid sequence enrichment of microorganisms can be obtained by a technique that uses differences in genomic signatures, herein specific k-mers, for selectively amplifying nucleic acid sequences of the microorganisms, i.e., pathogen DNA. The inventors found that specific k-mers can be used that preferentially amplify the target sequence by selecting k-mers that show differences in frequency and/or context between that target and background. In case of an unbiased amplification of bacterial DNA from blood samples, for example, the target of the selective amplification would correspond to the collection of microbial genome(s), and the subject, which represents the background nucleic acid sequences, to the human genome.

According to a first aspect, the present invention relates to a method of selectively amplifying at least one pathogen DNA sequence of at least one microorganism, which is chosen from archaea, bacteria, protists, and/or fungi, in a sample of a subject, which is a human patient, comprising:
providing a sample of the subject containing at least one pathogen DNA sequence of the at least one microorganism and at least one human DNA sequence of the subject;
determining at least one k-mer that shows a difference in frequency and/or context in the genome of the at least one microorganism compared to the genome of the subject; and
amplifying the pathogen DNA sequences in the sample using the at least one k-mer determined as primer,
characterized in that the at least one k-mer has a length of six nucleic acids.

In addition, a method of selectively amplifying at least one pathogen DNA sequence of at least one microorganism, which is chosen from archaea, bacteria, protists, and/or fungi, in a sample of a subject, which is a human patient, is disclosed in a further aspect, comprising:
providing a sample of the subject containing at least one pathogen DNA sequence of the at least one microorganism and at least one human DNA sequence of the subject; and
amplifying the pathogen DNA sequences in the sample using at least one k-mer that shows a difference in frequency and/or context in the genome of the at least one microorganism compared to the genome of the subject as primer, characterized in that the at least one k-mer has a length of six nucleic acids.

Furthermore disclosed is a data base, comprising a multitude of k-mers that shows a difference in frequency and/or context in the genome of at least one microorganism, which is chosen from archaea, bacteria, protists, and/or fungi, compared to the genome of a subject, which is a human patient, characterized in that the multitude of k-mers have a length of six nucleic acids.

In addition, the present invention relates to a method of selectively amplifying at least one pathogen DNA sequence of at least one microorganism, which is chosen from archaea, bacteria, protists, and/or fungi, in a sample of a subject, which is a human patient, comprising:

providing a sample of the subject containing at least one pathogen DNA sequence of the at least one microorganism and at least one human DNA sequence of the subject; and amplifying the pathogen DNA sequences in the sample using at least one k-mer, characterized in that the at least one k-mer has a length of six nucleic acids and that the at least one k-mer has a nucleotide sequence selected from the following group I as primer:

group I: CGNNNN (SEQ ID No. 1), NCGNNN (SEQ ID No. 2), NNCGNN (SEQ ID No. 3), NNNCGN (SEQ ID No. 4), NNNNCG (SEQ ID No. 5), CGCGNN (SEQ ID No. 6), CGNCGN (SEQ ID No. 7), CGNNCG (SEQ ID No. 8), NCGCGN (SEQ ID No. 9), NCGNCG (SEQ ID No. 10), NNCGCG (SEQ ID No. 11), CGCGCG (SEQ ID No. 12), wherein N is any nucleotide, preferably A, T, G, C or U.

Also disclosed is a method of selectively amplifying at least one pathogen DNA of at least one microorganism, which is chosen from archaea, bacteria, protists, and/or fungi, in a sample of a subject, which is a human patient, comprising:

providing a sample of the subject containing at least one pathogen DNA sequence of the at least one microorganism and at least one human DNA sequence of the subject; and amplifying the pathogen DNA sequences in the sample using at least one k-mer as primer, wherein the k-mer comprises in its sequence at least the sequence CG at any location of the k-mer sequence, characterized in that the at least one k-mer has a length of six nucleic acids.

Furthermore the present invention provides a kit for DNA amplification, comprising:

at least one polymerase; and at least one k-mer, characterized in that the at least one k-mer has a length of six nucleic acids and that the at least one k-mer has a nucleotide sequence selected from the following group I:

group I: CGNNNN (SEQ ID No. 1), NCGNNN (SEQ ID No. 2), NNCGNN (SEQ ID No. 3), NNNCGN (SEQ ID No. 4), NNNNCG (SEQ ID No. 5), CGCGNN (SEQ ID No. 6), CGNCGN (SEQ ID No. 7), CGNNCG (SEQ ID No. 8), NCGCGN (SEQ ID No. 9), NCGNCG (SEQ ID No. 10), NNCGCG (SEQ ID No. 11), CGCGCG (SEQ ID No. 12), wherein N is any nucleotide, preferably A, T, G, C or U.

Furthermore, the present invention provides a kit for DNA amplification, comprising:

at least one polymerase; and at least one k-mer comprising in its sequence at least the sequence CG at any location of the k-mer sequence, characterized in that the at least one k-mer has a length of six nucleic acids.

Further aspects and embodiments of the invention are disclosed in the dependent claims and can be taken from the following description, figures and examples, without being limited thereto.

BRIEF DESCRIPTION OF THE DRAWINGS

The enclosed drawings should illustrate embodiments of the present invention and convey a further understanding thereof. In connection with the description they serve as explanation of concepts and principles of the invention. Other embodiments and many of the stated advantages can be derived in relation to the drawings. The elements of the drawings are not necessarily to scale towards each other. Identical, functionally equivalent and acting equal features and components are denoted in the figures of the drawings with the same reference numbers, unless noted otherwise.

DETAILED DESCRIPTION OF THE INVENTION

Definitions

Figure 1:
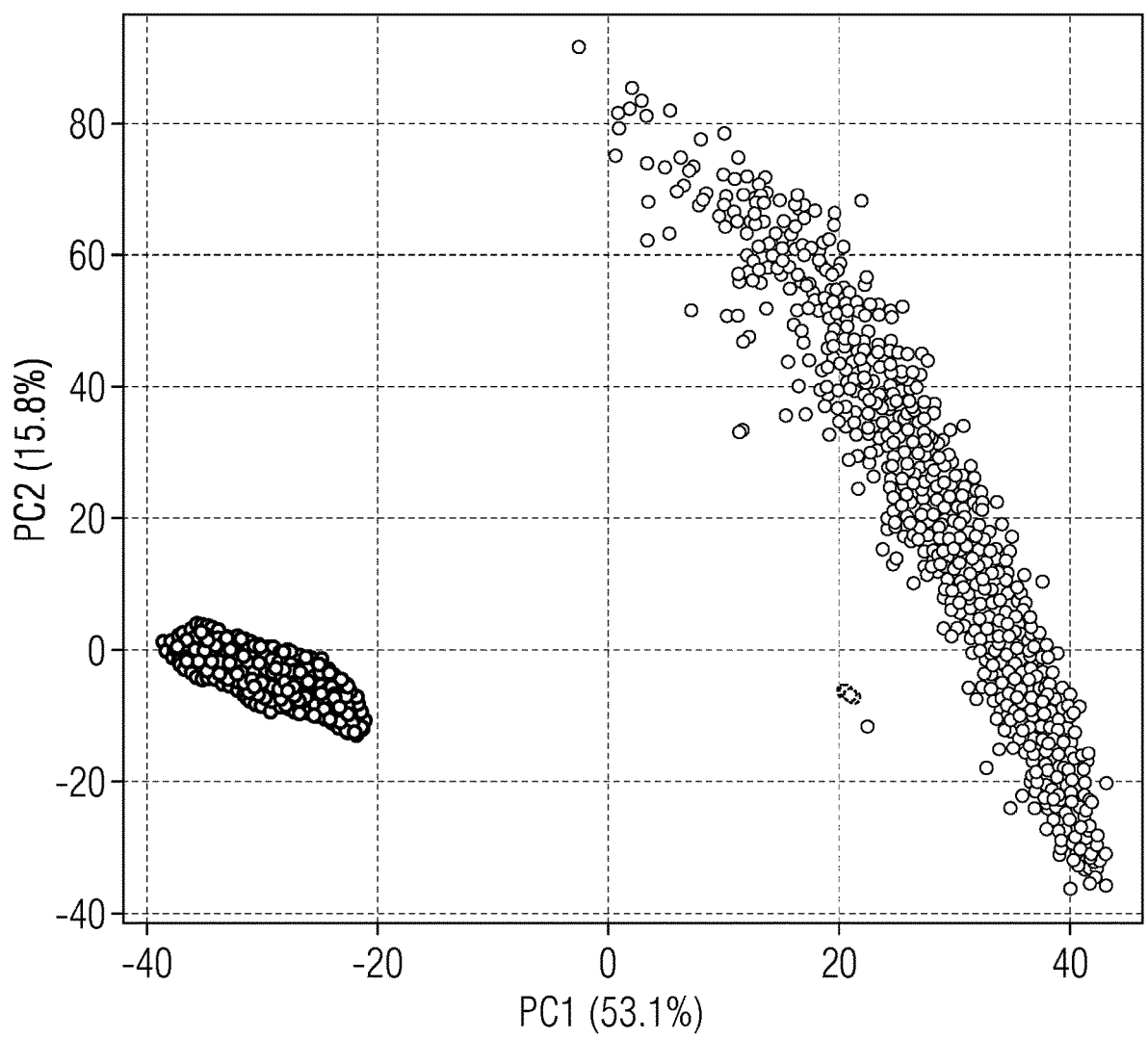
FIG. 1 shows a result of a principle component analysis regarding specific hexamers in an example of the invention.

Unless defined otherwise, technical and scientific terms used herein have the same meaning as commonly understood by one of ordinary skill in the art to which this invention belongs.

The term "nucleic acid molecule" refers to a polynucleotide molecule having a defined sequence. It comprises DNA molecules, RNA molecules, nucleotide analog molecules and combinations and derivatives thereof, such as DNA molecules or RNA molecules with incorporated nucleotide analogs or cDNA. Similarly, a nucleic acid sequence is the sequence of the polynucleotide, comprising DNA sequences, RNA sequences, sequences of nucleotide analog molecules and combinations and derivatives thereof, such as DNA molecules or RNA molecules with incorporated nucleotide analogs or cDNA. A nucleic acid sequence, also termed nucleotide sequence, is a sequence comprising more than one nucleotide. The nucleotides comprised therein are not particularly limited and can, e.g., comprise nucleotides found in nature, e.g., in genetic material, e.g., the nucleotide bases A (adenine), C (cytosine), G (guanine), T (thymine) and/or U (uracil).

In the context of the present invention, a "sample" of a subject is a sample which comprises at least one nucleic acid sequence of the at least one microorganism and/or virus and at least one nucleic acid sequence of the subject. Examples for samples are: samples of a subject like a patient, e.g., a human patient, e.g., cells, tissue, and/or biopsy specimens, etc.; body fluids such as blood, urine, saliva, sputum, plasma, serum, cell culture supernatant, swab sample, and others. Also included are samples taken from a natural and/or artificial surrounding comprising at least one microorganism and/or virus, e.g., soil samples, e.g., with a background of nucleic acid sequences of vertebrates, other animals like insects, etc., and/or of plants, etc.; deposits like fouling, etc.; biofilms, e.g., from waste management or in sanitary appliances, etc., and/or other microbiological consortia. According to certain embodiments, the sample is a patient sample (clinical isolate). Exemplary samples are serum, plasma, and/or whole blood of a patient. With the present methods, also more than one sample can be used at a time.

Within the present description the term "microorganism" comprises the term microbe. The type of microorganism is not particularly restricted, unless noted otherwise or obvious, and, for example, comprises bacteria, microscopic fungi, e.g., mold and/or yeast, microscopic algae, protozoa, and other protists, other unicellular organisms like amoeba, etc., as well as combinations thereof. A protist is therein any eukaryotic organism that is not an animal, plant, or fungus. According to certain embodiments, the at least one microorganism is chosen from archaea, bacteria, protists, and/or fungi.

A subject within the present invention can refer to an individual organism or a group of organisms of interest for selectively amplifying at least one nucleic acid sequence of at least one microorganism and/or virus, like, e.g., in a microbial consortium. It is therein not excluded that the group of organisms also includes nucleic acid sequences of non-living organisms, like lyzed bacteria, viruses, etc. Thus, it is also possible to enrich the nucleic acid sequences of, e.g., a specific archaea and/or bacterium can be selectively amplified in a sample comprising a microbial consortium. The subject can be, e.g., an animal like a vertebrate or an invertebrate, a plant, a fungus, a microbial consortium, etc., and is not particularly limited as long as a sample thereof comprises at least one nucleic acid sequence of the at least one microorganism and/or virus and at least one nucleic acid sequence of the subject. According to certain embodiments, the subject is a vertebrate or a microbial consortium.

A vertebrate within the present invention refers to animals having a vertebrate, which includes mammals—including humans, birds, reptiles, amphibians, and fishes. According to certain embodiments, the subject in the present methods is a vertebrate, more preferably a mammal, and most preferred a human, e.g., a patient. In this regard, it is especially of advantage to use a sample wherein the subject has a highly conserved genome, e.g., a human. However, also other organisms can be used as subject, e.g., a mouse, used, e.g., in a mouse model for medical analysis, a rat, etc.

A k-mer within the present invention refers to a nucleic acid sequence with a number k of nucleic acids, k being an integer with a value of 2 or more. According to certain embodiments, the k-mer has a length from 3 to 30 nucleic acids, preferably from 4 to 20 nucleic acids, further preferably from 5 to 15 nucleic acids, e.g., from 5 to 12, 6 to 11, or 6 to 10 nucleic acids, particularly 6 to 8 nucleic acids, e.g., being 6, 7 and/or 8 nucleic acids. The k-mer, which is used as a primer, can be in any shape.

A transcriptome refers to a set of nucleic acid sequences containing all messenger RNA molecules in one cell or a population of cells of an organism.

In contrast, the genome refers to the whole genetic material of the organism, and includes the genes, i.e., the coding regions, noncoding nucleic acid sequences like non-coding DNA of the whole organism, including the genetic material from mitochondria and/or chloroplasts.

A microbial consortium represents a set of two or more microbial groups living symbiotically, an example thereof being a biofilm. It is not excluded within this invention that the microbial consortium contains further organisms, etc., like viruses, plasmodes, amoeba, phages, etc. In microbial consortia, coverage of an organism of interest can be enhanced using the present methods.

Isothermal amplification is carried out at constant temperature and differs in this aspect from polymerase chain reaction (PCR). Multiple displacement amplification (MDA) is a nucleic acid sequence, e.g., DNA, amplification technique and uses isothermal amplification. It is usually carried out using a high fidelity enzyme, e.g., 029 DNA polymerase, at a constant temperature. Compared with conventional PCR amplification techniques, MDA generally generates larger sized products with a lower error frequency.

The present invention relates in a first aspect to a method of selectively amplifying at least one nucleic acid sequence of at least one microorganism and/or virus in a sample of a subject, comprising:

obtaining or providing a sample of the subject containing at least one nucleic acid sequence of the at least one microorganism and/or virus and at least one nucleic acid sequence of the subject;

determining at least one k-mer that shows a difference in frequency and/or context in the genome of the at least one microorganism and/or virus compared to the genome of the subject; and amplifying the nucleic acid sequences in the sample using the at least one k-mer determined as primer.

In this method, the sample can be provided or obtained in any way, preferably non-invasive, and can be, e.g., provided as an in vitro sample or prepared as in vitro sample.

Also, determining at least one k-mer that shows a difference in frequency and/or context in the genome of the at least one microorganism and/or virus compared to the genome of the subject is not particularly restricted. Thus, k-mers can show a difference in frequency in the genome of the at least one microorganism and/or virus compared to the genome of the subject, a difference in context in the genome of the at least one microorganism and/or virus compared to the genome of the subject, or a difference in frequency and context in the genome of the at least one microorganism and/or virus compared to the genome of the subject.

A difference in frequency in the genome of the at least one microorganism and/or virus compared to the genome of the subject is thereby an increased amount of a specific k-mer in the at least one microorganism and/or virus in relation to the genome size of the at least one microorganism and/or virus compared to the amount of the specific k-mer in the subject in relation to the genome of the subject. This means that a specific k-mer is relatively more abundant in its amount (i.e., number of occurrence in the genome) in the at least one microorganism and/or virus per genome size compared to the amount of the specific k-mer per genome size of the subject.

A difference in context refers to a difference in nucleic acid sequence, e.g., in pattern, of the k-mer in the at least one microorganism and/or virus compared to genome of the subject, i.e., if a specific k-mer sequence is only found in the at least one microorganism and/or virus.

Thus, the determining also encompasses cases wherein a specific k-mer is only found in the at least one microorganism and/or virus, so that no amplification of the genome of the subject takes place in the subsequent amplification step. However, also a selective amplification due to a relatively increased number of amplifications in the genome of the at least one microorganism and/or virus compared to the subject, i.e., a difference in frequency, or a combination of both is covered.

According to certain embodiments the determining of the at least one k-mer that shows a difference in frequency and/or context in the genome of the at least one microorganism and/or virus compared to the genome of the subject is carried out using a data base comprising the genome of the subject and the at least one microorganism and/or virus. The data base is not particularly restricted, and genome data can be obtained from, e.g., publicly available data bases like at the NCBI, JGI IMG, (JGI) GOLD, MBGD, Ensembl, 1000 Genomes Project, Exome Aggregation Consortium, etc., but also other data bases can be used.

The analysis of the data for the occurrence of k-mers with differences in frequency and/or context in the genome of the at least one microorganism and/or virus compared to the genome of the subject is thereby not particularly restricted. It is possible to search for k-mers of a certain length k as well as for k-mers with different lengths k simultaneously, and it is thus also possible to use k-mers with one certain length k or k-mers of several lengths k in the following amplifying step. According to certain embodiments, k-mers having a length from 3 to 30 nucleic acids, preferably from 4 to 20 nucleic acids, further preferably from 5 to 15 nucleic acids, e.g., from 5 to 12, 6 to 11, or 6 to 10 nucleic acids, particularly 6 to 8, e.g., having a length of 6, 7 and/or 8 nucleic acids, are determined.

According to certain embodiments, a multitude of k-mers is determined and used as primers in the amplification of the nucleic acid sequences in the sample. This way an unexpected increase in enrichment of nucleic acid sequences of the at least one microorganism and/or virus can be obtained.

According to certain embodiments, between 2-100000, e.g., between 5 and 100000, preferably between 50 and 30000, further preferably between 80 and 3000, e.g., from 100 to 200 k-mers are determined.

The amplifying of the nucleic acid sequences in the sample using the at least one k-mer determined in the step of determining at least one k-mer that shows a difference in frequency and/or context in the genome of the at least one microorganism and/or virus compared to the genome of the subject as primer is also not particularly restricted. As already discussed, it is also possible to use a multitude of k-mers as primers.

The amplifying method is not particularly restricted, and can be based on a PCR (polymerase chain reaction)-based and/or isothermal amplification-based technique, as known to the skilled person. According to certain embodiments, amplifying the nucleic acid sequences in the sample using the at least one k-mer determined as primer is carried out using isothermal amplification, preferably multiple displacement amplification. Also polymerases used in the amplification are not particularly restricted, and can be, e.g., a BST DNA enzyme, Φ29 DNA polymerase, etc.

In a second aspect, the present invention relates to a method of selectively amplifying at least one nucleic acid sequence of at least one microorganism and/or virus in a sample of a subject, comprising:

obtaining or providing a sample of the subject containing at least one nucleic acid sequence of the at least one microorganism and/or virus and at least one nucleic acid sequence of the subject; and amplifying the nucleic acid sequences in the sample using at least one k-mer that shows a difference in frequency and/or context in the genome of the at least one microorganism and/or virus compared to the genome of the subject as primer.

In the method of the first aspect, a data base comprising a multitude of k-mers can be generated in determining of the at least one k-mer that shows a difference in frequency and/or context in the genome of the at least one microorganism and/or virus compared to the genome of the subject, wherein all k-mers can be collected that show a difference in frequency and/or context in the genome of the at least one microorganism and/or virus compared to the genome of the subject. The data base that is generated therein can then be specific for all types of a specific at least one microorganism and/or virus, e.g., E. coli, compared to all types of a specific subject, e.g., different humans, and can be used in a further selective amplification when the subject of a sample is again a human and the microorganism of interest is again E. coli, and the determination step of the method of the first aspect does not have to be carried out again, as the data for specific k-mers are already known from the method of the first aspect. This means that for a specific type of microorganism and/or virus and/or more than one of each, and/or mixtures thereof, and a specific type of subject the determination of the at least one k-mer in the determining at least one k-mer that shows a difference in frequency and/or context in the genome of the at least one microorganism and/or virus compared to the genome of the subject only has to be carried out once, resulting in a data base with k-mers that show a difference in frequency and/or context in the genome of a specific at least one microorganism and/or virus compared to the genome of the specific subject.

This data base can then be used to suitably select at least one k-mer in a further sample wherein the nucleic acid sequences of the same specific at least one microorganism and/or virus are to be selectively amplified compared to the nucleic acid sequences of the same subject. Such a method is the method of the second aspect of the invention.

Accordingly, the obtaining or providing a sample of the subject containing at least one nucleic acid sequence of the at least one microorganism and/or virus and at least one nucleic acid sequence of the subject; and the amplifying the nucleic acid sequences in the sample using at least one k-mer that shows a difference in frequency and/or context in the genome of the at least one microorganism and/or virus compared to the genome of the subject as primer can be carried out as in the method of the first aspect of the present invention, and are likewise not particularly restricted.

Also, other embodiments of the first aspect apply also to the method of the second aspect, as far as they are applicable, e.g., regarding the use of multiple k-mers, etc.

According to certain embodiments, a multitude of k-mers that shows a difference in frequency and/or context in the genome of the at least one microorganism and/or virus compared to the genome of the subject are used as primers in amplifying the nucleic acid sequences in the sample.

The present invention also relates—in a third aspect—to a data base, comprising a multitude of k-mers that shows a difference in frequency and/or context in the genome of at least one microorganism and/or virus compared to the genome of a subject. As described above, this data base can be obtained in determining the at least one k-mer that shows a difference in frequency and/or context in the genome of the at least one microorganism and/or virus compared to the genome of the subject in the method of the first aspect, wherein all k-mers that show a difference in frequency and/or context in the genome of the at least one microorganism and/or virus compared to the genome of the subject can be contained in the data base. Further, as discussed above, the data base is then specific for the at least one microorganism and/or virus in a specific subject, and can be used accordingly when the nucleic acid sequences of at least one microorganism and/or virus of the same type of the specific at least one microorganism and/or virus, e.g., another *E. coli* bacteria, is to be selectively amplified in a sample of a subject of the same type, e.g., another human.

According to certain embodiments, the subject for the data base is a vertebrate and/or a microbial consortium, e.g., a vertebrate, particularly a human.

The inventors have further found that with particular k-mers, respectively k-mer sets, e.g., hexamers, heptamers, and/or octamers, particularly with specific sequences or at least specific sequence parts, a further enrichment of nucleic acid sequence of the at least one microorganism and/or virus in the sample can be achieved.

According to certain embodiments, at least one k-mer in the multitude of k-mers of the data base of the third aspect is a k-mer having a nucleotide sequence selected from the following groups I, II, and/or III:

group I: CGNNNN (SEQ ID No. 1), NCGNNN (SEQ ID No. 2), NNCGNN (SEQ ID No. 3), NNNCGN (SEQ ID No. 4), NNNNCG (SEQ ID No. 5), CGCGNN (SEQ ID No. 6), CGNCGN (SEQ ID No. 7), CGNNCG (SEQ ID No. 8), NCGCGN (SEQ ID No. 9), NCGNCG (SEQ ID No. 10), NNCGCG (SEQ ID No. 11), CGCGCG (SEQ ID No. 12);

group II: CGNNNNN (SEQ ID No. 13), NCGNNNN (SEQ ID No. 14), NNCGNNN (SEQ ID No. 15), NNNCGNN (SEQ ID No. 16), NNNNCGN (SEQ ID No. 17), NNNNNCG (SEQ ID No. 18), CGCGNNN (SEQ ID No. 19), CGNCGNN (SEQ ID No. 20), CGNNCGN (SEQ ID No. 21), CGNNNCG (SEQ ID No. 22), NCGCGNN (SEQ ID No. 23), NCGNCGN (SEQ ID No. 24), NCGNNCG (SEQ ID No. 25), NNCGCGN (SEQ ID No. 26), NNCGNCG (SEQ ID No. 27), NNNCGCG (SEQ ID No. 28), CGCGCGN (SEQ ID No. 29), CGCGNCG (SEQ ID No. 30), CGNCGCG (SEQ ID No. 31), NCGCGCG (SEQ ID No. 32);

group III: CGNNNNNN (SEQ ID No. 33), NCGNNNNN (SEQ ID No. 34), NNCGNNNN (SEQ ID No. 35), NNNCGNNN (SEQ ID No. 36), NNNNCGNN (SEQ ID No. 37), NNNNNCGN (SEQ ID No. 38), NNNNNNCG (SEQ ID No. 39), CGCGNNNN (SEQ ID No. 40), CGNCGNNN (SEQ ID No. 41), CGNNCGNN (SEQ ID No. 42), CGNNNCGN (SEQ ID No. 43), CGNNNNCG (SEQ ID No. 44), NCGCGNNN (SEQ ID No. 45), NCGNCGNN (SEQ ID No. 46), NCGNNCGN (SEQ ID No. 47), NCGNNNCG (SEQ ID No. 48), NNCGCGNN (SEQ ID No. 49), NNCGNCGN (SEQ ID No. 50), NNCGNNCG (SEQ ID No. 51), NNNCGCGN (SEQ ID No. 52), NNNCGNCG (SEQ ID No. 53), NNNNCGCG (SEQ ID No. 54), CGCGCGNN (SEQ ID No. 55), CGCGNCGN (SEQ ID No. 56), CGCGNNCG (SEQ ID No. 57), CGNCGCGN (SEQ ID No. 58), CGNCGNCG (SEQ ID No. 59), CGNNCGCG (SEQ ID No. 60), NCGCGCGN (SEQ ID No. 61), NCGCGNCG (SEQ ID No. 62), NCGNCGCG (SEQ ID No. 63), NNCGCGCG (SEQ ID No. 64), CGCGCGCG (SEQ ID No. 65);

wherein N is any nucleotide, preferably A, T, G, C or U.

Thus, a multitude of sequences is possible for any sequence containing an N, as each N can stand for, e.g., A, C, G or T, etc., and NN thus for, e.g., AA, AC, AG, AT, CA, CC, CG, CT, GA, GC, GG, GT, TA, TC, TG, TT, etc., and so forth.

According to certain embodiments, more than one k-mer having a nucleotide sequence selected from the groups I, II, and/or III can be contained in the data base, e.g., 2, 3, 4, 5, 6, 7, 8, 9, 10, 11, 12, 13, 14, 15, 16, 17, 18, 19, 20, 21, 22, 23, 24, 25, or more k-mers.

According to certain embodiments, the data base comprises a k-mer or k-mer combination, i.e., a multitude of k-mers, chosen from the following:

IV: CGNCGN (SEQ ID No. 7), NCGNCG (SEQ ID No. 10), CGCGNN (SEQ ID No. 6), NCGCGN (SEQ ID No. 9), CGNNCG (SEQ ID No. 8), NNCGCG (SEQ ID No. 11), NNGCGC (SEQ ID No. 66), NNCGGC (SEQ ID No. 67), NGCGCN (SEQ ID No. 68), NGCNGC (SEQ ID No. 69), GCCGNN (SEQ ID No. 70), GCGCNN (SEQ ID No. 71), CGNNGC (SEQ ID No. 72), NCGGCN (SEQ ID No. 73), CGGCNN (SEQ ID No. 74), NNGCCG (SEQ ID No. 75), NGCCGN (SEQ ID No. 76), NGCNCG (SEQ ID No. 77), GCNCGN (SEQ ID No. 78), NCGNGC (SEQ ID No. 79), CGNGCN (SEQ ID No. 80), GCNGCN (SEQ ID No. 81), GCNNGC (SEQ ID No. 82), GCNNCG (SEQ ID No. 83);

V: CGNCGN (SEQ ID No. 7), NCGNCG (SEQ ID No. 10);

VI: CGNCGN (SEQ ID No. 7);

VII: CGACGN (SEQ ID No. 84);

VIII: CGACGC (SEQ ID No. 85);

IX: CGGCGC (SEQ ID No. 86); i.e. with the 24 k-mers of IV as primers, the 2 k-mers of V as primers, the k-mer of VII as primer, the k-mer of VIII as primer, or the k-mer of IX as primer. According to certain embodiments, the data base comprises the sequence CGGCGC (IX).

According to certain embodiments, at least one k-mer in the multitude of k-mers of the data base of the third aspect is a k-mer comprising in its sequence at least the sequence CG at any location of the k-mer sequence. The inventors found that particularly the sequence CG in a k-mer, particularly in hexamers, heptamers and/or octamers, can lead to a further enhancement of the selective amplification.

According to certain embodiments of the method of the second aspect, the above data base of the third aspect is used to select the at least one k-mer that shows a difference in frequency and/or context in the genome of the at least one microorganism and/or virus compared to the genome of the subject as primer in the amplification of the nucleic acid sequences in the sample.

In a fourth aspect, the present invention relates to a method of selectively amplifying at least one nucleic acid sequence of at least one microorganism and/or virus in a sample of a subject, comprising:

obtaining or providing a sample of the subject containing at least one nucleic acid sequence of the at least one microorganism and/or virus and at least one nucleic acid sequence of the subject; and amplifying the nucleic acid sequences in the sample using at least one k-mer having a nucleotide sequence selected from the following groups I, II, and/or III as primer:

group I: CGNNNN (SEQ ID No. 1), NCGNNN (SEQ ID No. 2), NNCGNN (SEQ ID No. 3), NNNCGN (SEQ ID No. 4), NNNNCG (SEQ ID No. 5), CGCGNN (SEQ ID No. 6), CGNCGN (SEQ ID No. 7), CGNNCG (SEQ ID No. 8), NCGCGN (SEQ ID No. 9), NCGNCG (SEQ ID No. 10), NNCGCG (SEQ ID No. 11), CGCGCG (SEQ ID No. 12);

group II: CGNNNNN (SEQ ID No. 13), NCGNNNN (SEQ ID No. 14), NNCGNNN (SEQ ID No. 15), NNNCGNN (SEQ ID No. 16), NNNNCGN (SEQ ID No. 17), NNNNNCG (SEQ ID No. 18), CGCGNNN (SEQ ID No. 19), CGNCGNN (SEQ ID No. 20), CGNNCGN (SEQ ID No. 21), CGNNNCG (SEQ ID No. 22), NCGCGNN (SEQ ID No. 23), NCGNCGN (SEQ ID No. 24), NCGNNCG (SEQ ID No. 25), NNCGCGN (SEQ ID No. 26), NNCGNCG (SEQ ID No. 27), NNNCGCG (SEQ ID No. 28), CGCGCGN (SEQ ID No. 29), CGCGNCG (SEQ ID No. 30), CGNCGCG (SEQ ID No. 31), NCGCGCG (SEQ ID No. 32);

group III: CGNNNNNN (SEQ ID No. 33), NCGNNNNN (SEQ ID No. 34), NNCGNNNN (SEQ ID No. 35), NNNCGNNN (SEQ ID No. 36), NNNNCGNN (SEQ ID No. 37), NNNNNCGN (SEQ ID No. 38), NNNNNNCG (SEQ ID No. 39), CGCGNNNN (SEQ ID No. 40), CGNCGNNN (SEQ ID No. 41), CGNNCGNN (SEQ ID No. 42), CGNNNCGN (SEQ ID No. 43), CGNNNNCG (SEQ ID No. 44), NCGCGNNN (SEQ ID No. 45), NCGNCGNN (SEQ ID No. 46), NCGNNCGN (SEQ ID No. 47), NCGNNNCG (SEQ ID No. 48), NNCGCGNN (SEQ ID No. 49), NNCGNCGN (SEQ ID No. 50), NNCGNNCG (SEQ ID No. 51), NNNCGCGN (SEQ ID No. 52), NNNCGNCG (SEQ ID No. 53), NNNNCGCG (SEQ ID No. 54), CGCGCGNN (SEQ ID No. 55), CGCGNCGN (SEQ ID No. 56), CGCGNNCG (SEQ ID No. 57), CGNCGCGN (SEQ ID No. 58), CGNCGNCG (SEQ ID No. 59), CGNNCGCG (SEQ ID No. 60), NCGCGCGN (SEQ ID No. 61), NCGCGNCG (SEQ ID No. 62), NCGNCGCG (SEQ ID No. 63), NNCGCGCG (SEQ ID No. 64), CGCGCGCG (SEQ ID No. 65);

wherein N is any nucleotide, preferably A, T, G, C or U.

According to certain embodiments, more than one nucleotide sequence selected from the following groups I, II, and/or III can be used as primer, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or more.

According to certain embodiments, the amplification is carried out using at least one k-mer having a nucleotide sequence selected from group I. According to certain embodiments, the amplification is carried out using hexamers as primers.

According to certain embodiments, the amplification is carried out using at least one k-mer having a nucleotide sequence selected from group II. According to certain embodiments, the amplification is carried out using heptamers as primers.

According to certain embodiments, the amplification is carried out using at least one k-mer having a nucleotide sequence selected from group III. According to certain embodiments, the amplification is carried out using octamers as primers.

According to certain embodiments, the amplification is carried out using a k-mer or k-mer combination, i.e., a multitude of k-mers, chosen from the following:

IV: CGNCGN (SEQ ID No. 7), NCGNCG (SEQ ID No. 10), CGCGNN (SEQ ID No. 6), NCGCGN (SEQ ID No. 9), CGNNCG (SEQ ID No. 8), NNCGCG (SEQ ID No. 11), NNGCGC (SEQ ID No. 66), NNCGGC (SEQ ID No. 67), NGCGCN (SEQ ID No. 68), NGCNGC (SEQ ID No. 69), GCCGNN (SEQ ID No. 70), GCGCNN (SEQ ID No. 71), CGNNGC (SEQ ID No. 72), NCGGCN (SEQ ID No. 73), CGGCNN (SEQ ID No. 74), NNGCCG (SEQ ID No. 75), NGCCGN (SEQ ID No. 76), NGCNCG (SEQ ID No. 77), GCNCGN (SEQ ID No. 78), NCGNGC (SEQ ID No. 79), CGNGCN (SEQ ID No. 80), GCNGCN (SEQ ID No. 81), GCNNGC (SEQ ID No. 82), GCNNCG (SEQ ID No. 83);

V: CGNCGN (SEQ ID No. 7), NCGNCG (SEQ ID No. 10);

VI: CGNCGN (SEQ ID No. 7);

VII: CGACGN (SEQ ID No. 84);

VIII: CGACGC (SEQ ID No. 85);

IX: CGGCGC (SEQ ID No. 86); i.e. with the 24 k-mers of IV as primers, the 2 k-mers of V as primers, the k-mer of VII as primer, the k-mer of VIII as primer, or the k-mer of IX as primer. According to certain embodiments, the amplification is carried out in the presence of the k-mer with the sequence CGGCGC (IX) as primer.

According to certain embodiments, a random k-mer is further used for amplification in the method of the fourth aspect. According to certain embodiments, the further k-mer has the same length as the at least one k-mer of group I, II, and/or III, i.e., is a hexamer, heptamer, and/or octamer. According to certain embodiments, the at least one k-mer of group I, II, and/or III is added in an amount of 1 µmol L$^{-1}$ to 1000 µmol L$^{-1}$, and the further k-mer is added in an amount of 1 µmol L$^{-1}$ to 100 nmol L$^{-1}$. Such an addition of a minor amount of a random k-mer, e.g., hexamer, e-g- in the µmol L-1 to nmol L-1 range, can shorten time of reaction in the amplification substantially.

According to certain embodiments, the amplification in the method of the fourth aspect is a multiple displacement amplification, e.g., as described above.

A fifth aspect of the present invention is directed to a method of selectively amplifying at least one nucleic acid sequence of at least one microorganism and/or virus in a sample of a subject, comprising:

obtaining or providing a sample of the subject containing at least one nucleic acid sequence of the at least one microorganism and/or virus and at least one nucleic acid sequence of the subject; and amplifying the nucleic acid sequences in the sample using at least one k-mer, particularly having a length from 3 to 30 nucleic acids, preferably from 4 to 20 nucleic acids, further preferably from 5 to 15 nucleic acids, e.g., from 5 to 12, 6 to 11, or 6 to 10 nucleic acids, particularly 6 to 8 nucleic acids, e.g., being 6, 7, and/or 8 nucleic acids, as primer, wherein the k-mer comprises in its sequence at least the sequence CG at any location of the k-mer sequence. As already explained above, the inventors found that the presence of the sequence CG in any k-mer sequence can lead to improved results in the enrichment of the nucleic acid sequence of the at least one microorganism and/or virus in a sample of the subject, even better than theoretically expected.

As in the fourth aspect, a random k-mer can be further used for amplification as primer in the method of the fifth aspect. The further k-mer can—according to certain embodiments—have the same length as the at least one k-mer comprising in its sequence at least the sequence CG at any location of the k-mer sequence. According to certain embodiments, the at least one k-mer comprising in its sequence at least the sequence CG at any location of the k-mer sequence is added in an amount of 1 µmol L$^{-1}$ to 1000 µmol L$^{-1}$, and the further k-mer is added in an amount of 1 µmol L$^{-1}$ to 100 nmol L$^{-1}$.

In a sixth aspect a kit for DNA amplification is disclosed, comprising:

at least one polymerase; and at least one k-mer having a nucleotide sequence selected from the following groups I, II, and/or III:

group I: CGNNNN (SEQ ID No. 1), NCGNNN (SEQ ID No. 2), NNCGNN (SEQ ID No. 3), NNNCGN (SEQ ID No. 4), NNNNCG (SEQ ID No. 5), CGCGNN (SEQ ID No. 6), CGNCGN (SEQ ID No. 7), CGNNCG (SEQ ID No. 8), NCGCGN (SEQ ID No. 9), NCGNCG (SEQ ID No. 10), NNCGCG (SEQ ID No. 11), CGCGCG (SEQ ID No. 12);

group II: CGNNNNN (SEQ ID No. 13), NCGNNNN (SEQ ID No. 14), NNCGNNN (SEQ ID No. 15), NNNCGNN (SEQ ID No. 16), NNNNCGN (SEQ ID No. 17), NNNNNCG (SEQ ID No. 18), CGCGNNN (SEQ ID No. 19), CGNCGNN (SEQ ID No. 20), CGNNCGN (SEQ ID No. 21), CGNNNCG (SEQ ID No. 22), NCGCGNN (SEQ ID No. 23), NCGNCGN (SEQ ID No. 24), NCGNNCG (SEQ ID No. 25), NNCGCGN (SEQ ID No.

26), NNCGNCG (SEQ ID No. 27), NNNCGCG (SEQ ID No. 28), CGCGCGN (SEQ ID No. 29), CGCGNCG (SEQ ID No. 30), CGNCGCG (SEQ ID No. 31), NCGCGCG (SEQ ID No. 32);

group III: CGNNNNNN (SEQ ID No. 33), NCGNNNNN (SEQ ID No. 34), NNCGNNNN (SEQ ID No. 35), NNNCGNNN (SEQ ID No. 36), NNNNCGNN (SEQ ID No. 37), NNNNNCGN (SEQ ID No. 38), NNNNNNCG (SEQ ID No. 39), CGCGNNNN (SEQ ID No. 40), CGNCGNNN (SEQ ID No. 41), CGNNCGNN (SEQ ID No. 42), CGNNNCGN (SEQ ID No. 43), CGNNNNCG (SEQ ID No. 44), NCGCGNNN (SEQ ID No. 45), NCGNCGNN (SEQ ID No. 46), NCGNNCGN (SEQ ID No. 47), NCGNNNCG (SEQ ID No. 48), NNCGCGNN (SEQ ID No. 49), NNCGNCGN (SEQ ID No. 50), NNCGNNCG (SEQ ID No. 51), NNNCGCGN (SEQ ID No. 52), NNNCGNCG (SEQ ID No. 53), NNNNCGCG (SEQ ID No. 54), CGCGCGNN (SEQ ID No. 55), CGCGNCGN (SEQ ID No. 56), CGCGNNCG (SEQ ID No. 57), CGNCGCGN (SEQ ID No. 58), CGNCGNCG (SEQ ID No. 59), CGNNCGCG (SEQ ID No. 60), NCGCGCGN (SEQ ID No. 61), NCGCGNCG (SEQ ID No. 62), NCGNCGCG (SEQ ID No. 63), NNCGCGCG (SEQ ID No. 64), CGCGCGCG (SEQ ID No. 65);

wherein N is any nucleotide, preferably A, T, G, C or U.

According to certain embodiments, the kit can comprise more than one nucleotide sequence selected from the following groups I, II, and/or III, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or more k-mers.

According to certain embodiments, the kit comprises a k-mer or k-mer combination, i.e., a multitude of k-mers, chosen from the following:

IV: CGNCGN (SEQ ID No. 7), NCGNCG (SEQ ID No. 10), CGCGNN (SEQ ID No. 6), NCGCGN (SEQ ID No. 9), CGNNCG (SEQ ID No. 8), NNCGCG (SEQ ID No. 11), NNGCGC (SEQ ID No. 66), NNCGGC (SEQ ID No. 67), NGCGCN (SEQ ID No. 68), NGCNGC (SEQ ID No. 69), GCCGNN (SEQ ID No. 70), GCGCNN (SEQ ID No. 71), CGNNGC (SEQ ID No. 72), NCGGCN (SEQ ID No. 73), CGGCNN (SEQ ID No. 74), NNGCCG (SEQ ID No. 75), NGCCGN (SEQ ID No. 76), NGCNCG (SEQ ID No. 77), GCNCGN (SEQ ID No. 78), NCGNGC (SEQ ID No. 79), CGNGCN (SEQ ID No. 80), GCNGCN (SEQ ID No. 81), GCNNGC (SEQ ID No. 82), GCNNCG (SEQ ID No. 83);

V: CGNCGN (SEQ ID No. 7), NCGNCG (SEQ ID No. 10);

VI: CGNCGN (SEQ ID No. 7);

VII: CGACGN (SEQ ID No. 84);

VIII: CGACGC (SEQ ID No. 85);

IX: CGGCGC (SEQ ID No. 86); i.e., with the 24 k-mers of IV as primers, the 2 k-mers of V as primers, the k-mer of VI as primer, the k-mer of VII as primer, the k-mer of VIII as primer, or the k-mer of IX as primer. According to certain embodiments, the kit comprises the sequence CGGCGC (IX) as primer.

Furthermore disclosed is in a seventh aspect a kit for DNA amplification, comprising:

at least one polymerase; and at least one k-mer, particularly having a length from 3 to 30 nucleic acids, preferably from 4 to 20 nucleic acids, further preferably from 5 to 15 nucleic acids, e.g., from 5 to 12, 6 to 11, or 6 to 10 nucleic acids, particularly 6 to 8 nucleic acids, e.g., being 6, 7, and/or 8 nucleic acids, comprising in its sequence at least the sequence CG at any location of the k-mer sequence.

Both the kits of the sixth and seventh aspect can further comprise a multitude of nucleotides, and both can be used in suitable amplification techniques, e.g., as described above, e.g., MDA. The at least one polymerase in the kits of the sixth and seventh aspect thus can be, e.g., 029 DNA polymerase.

An amplification method, like MDA, with k-mers determined in the method of the first aspect can be included in a standard workflow and subsequently does not require an extra sample preparation step. Further, an amplifying technique, e.g., MDA, with such k-mers enables both a sample enrichment and obtaining a nucleic acid sequence, e.g., DNA, amplification with a nucleic acid, e.g., DNA, sequence amount sufficient for sequencing.

With the method of the first aspect, a selection of a specific subset of k-mers is possible after employing a bioinformatic analysis, i.e., a process wherein differences in k-mer signature and/or frequency can be determined, in the determination step, which can, e.g., be only necessary once per host, particularly for highly conserved genomes.

The above embodiments can be combined arbitrarily, if appropriate. Further possible embodiments and implementations of the invention comprise also combinations of features not explicitly mentioned in the foregoing or in the following with regard to the examples of the invention. Particularly, a person skilled in the art will also add individual aspects as improvements or additions to the respective basic form of the invention.

Further embodiments of the invention are as follows:

Embodiment 1

A method of selectively amplifying at least one nucleic acid sequence of at least one microorganism and/or virus in a sample of a subject, comprising:

obtaining or providing a sample of the subject containing at least one nucleic acid sequence of the at least one microorganism and/or virus and at least one nucleic acid sequence of the subject;

determining at least one k-mer that shows a difference in frequency and/or context in the genome of the at least one microorganism and/or virus compared to the genome of the subject; and amplifying the nucleic acid sequences in the sample using the at least one k-mer determined as primer.

Embodiment 2

The method of embodiment 1, wherein the k-mer has a length from 3 to 30 nucleic acids.

Embodiment 3

The method of embodiment 1 or 2, wherein the subject is a vertebrate or a microbial consortium.

Embodiment 4

The method of any one of the preceding embodiments, wherein the at least one microorganism is chosen from archaea, bacteria, protists, and/or fungi.

Embodiment 5

The method of any one of the preceding embodiments, wherein a multitude of k-mers is determined and used as primers in the amplification of the nucleic acid sequences in the sample.

Embodiment 6

The method of embodiment 5, wherein between 5 and 100000 k-mers are determined.

Embodiment 7

The method of embodiment 6, wherein between 50 and 30000 k-mers are determined.

Embodiment 8

The method of any one of the preceding embodiments, wherein the determining of the at least one k-mer that shows a difference in frequency and/or context in the genome of the at least one microorganism and/or virus compared to the genome of the subject is carried out using a data base comprising the genome of the subject and the at least one microorganism and/or virus.

Embodiment 9

The method of any one of the preceding embodiments, wherein amplifying the nucleic acid sequences in the sample using the at least one k-mer determined as primer is carried out using isothermal amplification.

Embodiment 10

The method of embodiment 9, wherein the isothermal amplification is a multiple displacement amplification.

Embodiment 11

A method of selectively amplifying at least one nucleic acid sequence of at least one microorganism and/or virus in a sample of a subject, comprising:
 obtaining or providing a sample of the subject containing at least one nucleic acid sequence of the at least one microorganism and/or virus and at least one nucleic acid sequence of the subject; and
 amplifying the nucleic acid sequences in the sample using at least one k-mer that shows a difference in frequency and/or context in the genome of the at least one microorganism and/or virus compared to the genome of the subject as primer.

Embodiment 12

The method of embodiment 11, wherein a multitude of k-mers that shows a difference in frequency and/or context in the genome of the at least one microorganism and/or virus compared to the genome of the subject are used as primers.

Embodiment 13

A data base, comprising a multitude of k-mers that shows a difference in frequency and/or context in the genome of at least one microorganism and/or virus compared to the genome of a subject.

Embodiment 14

The data base of embodiment 13, wherein the subject is a vertebrate and/or a microbial consortium.

Embodiment 15

The method of embodiment 11 or 12, wherein the data base of embodiment 13 or 14 is used to select the at least one k-mer that shows a difference in frequency and/or context in the genome of the at least one microorganism and/or virus compared to the genome of the subject as primer in the amplification of the nucleic acid sequences in the sample.

Embodiment 16

A method of selectively amplifying at least one nucleic acid sequence of at least one microorganism and/or virus in a sample of a subject, comprising:
 obtaining or providing a sample of the subject containing at least one nucleic acid sequence of the at least one microorganism and/or virus and at least one nucleic acid sequence of the subject; and
 amplifying the nucleic acid sequences in the sample using at least one k-mer having a nucleotide sequence selected from the following groups I, II, and/or III as primer:
 group I: CGNNNN (SEQ ID No. 1), NCGNNN (SEQ ID No. 2), NNCGNN (SEQ ID No. 3), NNNCGN (SEQ ID No. 4), NNNNCG (SEQ ID No. 5), CGCGNN (SEQ ID No. 6), CGNCGN (SEQ ID No. 7), CGNNCG (SEQ ID No. 8), NCGCGN (SEQ ID No. 9), NCGNCG (SEQ ID No. 10), NNCGCG (SEQ ID No. 11), CGCGCG (SEQ ID No. 12);
 group II: CGNNNNN (SEQ ID No. 13), NCGNNNN (SEQ ID No. 14), NNCGNNN (SEQ ID No. 15), NNNCGNN (SEQ ID No. 16), NNNNCGN (SEQ ID No. 17), NNNNNCG (SEQ ID No. 18), CGCGNNN (SEQ ID No. 19), CGNCGNN (SEQ ID No. 20), CGNNCGN (SEQ ID No. 21), CGNNNCG (SEQ ID No. 22), NCGCGNN (SEQ ID No. 23), NCGNCGN (SEQ ID No. 24), NCGNNCG (SEQ ID No. 25), NNCGCGN (SEQ ID No. 26), NNCGNCG (SEQ ID No. 27), NNNCGCG (SEQ ID No. 28), CGCGCGN (SEQ ID No. 29), CGCGNCG (SEQ ID No. 30), CGNCGCG (SEQ ID No. 31), NCGCGCG (SEQ ID No. 32);
 group III: CGNNNNNN (SEQ ID No. 33), NCGNNNNN (SEQ ID No. 34), NNCGNNNN (SEQ ID No. 35), NNNCGNNN (SEQ ID No. 36), NNNNCGNN (SEQ ID No. 37), NNNNNCGN (SEQ ID No. 38), NNNNNNCG (SEQ ID No. 39), CGCGNNNN (SEQ ID No. 40), CGNCGNNN (SEQ ID No. 41), CGNNCGNN (SEQ ID No. 42), CGNNNCGN (SEQ ID No. 43), CGNNNNCG (SEQ ID No. 44), NCGCGNNN (SEQ ID No. 45), NCGNCGNN (SEQ ID No. 46), NCGNNCGN (SEQ ID No. 47), NCGNNNCG (SEQ ID No. 48), NNCGCGNN (SEQ ID No. 49), NNCGNCGN (SEQ ID No. 50), NNCGNNCG (SEQ ID No. 51), NNNCGCGN (SEQ ID No. 52), NNNCGNCG (SEQ ID No. 53), NNNNCGCG (SEQ ID No. 54), CGCGCGNN (SEQ ID No. 55), CGCGNCGN (SEQ ID No. 56), CGCGNNCG (SEQ ID No. 57), CGNCGCGN (SEQ ID No. 58), CGNCGNCG (SEQ ID No. 59), CGNNCGCG (SEQ ID No. 60), NCGCGCGN (SEQ ID No. 61), NCGCGNCG (SEQ ID No. 62), NCGNCGCG (SEQ ID No. 63), NNCGCGCG (SEQ ID No. 64), CGCGCGCG (SEQ ID No. 65);
 wherein N is any nucleotide, preferably A, T, G, C or U.

Embodiment 17

The method of embodiment 16, wherein the amplification is carried out using at least one k-mer having a nucleotide sequence selected from group I.

Embodiment 18

The method of embodiment 16 or 17, wherein the amplification is carried out using a k-mer or k-mer combination chosen from the following:

```
IV:
CGNCGN,      (SEQ ID No. 7)
NCGNCG,      (SEQ ID No. 10)
CGCGNN,      (SEQ ID No. 6)
NCGCGN,      (SEQ ID No. 9)
CGNNCG,      (SEQ ID No. 8)
NNCGCG,      (SEQ ID No. 11)
NNGCGC,      (SEQ ID No. 66)
NNCGGC,      (SEQ ID No. 67)
NGCGCN,      (SEQ ID No. 68)
NGCNGC,      (SEQ ID No. 69)
GCCGNN,      (SEQ ID No. 70)
GCGCNN,      (SEQ ID No. 71)
CGNNGC,      (SEQ ID No. 72)
NCGGCN,      (SEQ ID No. 73)
CGGCNN,      (SEQ ID No. 74)
NNGCCG,      (SEQ ID No. 75)
NGCCGN,      (SEQ ID No. 76)
NGCNCG,      (SEQ ID No. 77)
GCNCGN,      (SEQ ID No. 78)
NCGNGC,      (SEQ ID No. 79)
CGNGCN,      (SEQ ID No. 80)
GCNGCN,      (SEQ ID No. 81)
GCNNGC,      (SEQ ID No. 82)
GCNNCG;      (SEQ ID No. 83)
V:
CGNCGN,      (SEQ ID No. 7)
NCGNCG;      (SEQ ID No. 10)
VI:
CGNCGN;      (SEQ ID No. 7)
VII:
CGACGN;      (SEQ ID No. 84)
VIII:
CGACGC;      (SEQ ID No. 85)
IX:
CGGCGC.      (SEQ ID No. 86)
```

Embodiment 19

The method of any one of embodiments 16 to 18, wherein a random k-mer is further used for amplification.

Embodiment 20

The method of embodiment 19, wherein the further k-mer has the same length as the at least one k-mer of group I, II, and/or III.

Embodiment 21

The method of embodiment 19 or 20, wherein the at least one k-mer of group I, II, and/or III is added in an amount of 1 µmol $L^{-1}$ to 1000 µmol $L^{-1}$, and the further k-mer is added in an amount of 1 µmol $L^{-1}$ to 100 nmol $L^{-1}$.

Embodiment 22

A method of selectively amplifying at least one nucleic acid sequence of at least one microorganism and/or virus in a sample of a subject, comprising:
  obtaining or providing a sample of the subject containing at least one nucleic acid sequence of the at least one microorganism and/or virus and at least one nucleic acid sequence of the subject; and
  amplifying the nucleic acid sequences in the sample using at least one k-mer as primer, wherein the k-mer comprises in its sequence at least the sequence CG at any location of the k-mer sequence.

Embodiment 23

The method of embodiment 22, wherein a random k-mer is further used for amplification.

Embodiment 24

The method of embodiment 23, wherein the further k-mer has the same length as the at least one k-mer comprising in its sequence at least the sequence CG at any location of the k-mer sequence.

Embodiment 25

The method of embodiment 23 or 24, wherein the at least one k-mer comprising in its sequence at least the sequence CG at any location of the k-mer sequence is added in an amount of 1 µmol $L^{-1}$ to 1000 µmol $L^{-1}$, and the further k-mer is added in an amount of 1 µmol $L^{-1}$ to 100 nmol $L^{-1}$.

Embodiment 26

A kit for DNA amplification, comprising:
  at least one polymerase; and
  at least one k-mer having a nucleotide sequence selected from the following groups I, II, and/or III:
    group I: CGNNNN (SEQ ID No. 1), NCGNNN (SEQ ID No. 2), NNCGNN (SEQ ID No. 3), NNNCGN (SEQ ID No. 4), NNNNCG (SEQ ID No. 5), CGCGNN (SEQ ID No. 6), CGNCGN (SEQ ID No. 7), CGNNCG (SEQ ID No. 8), NCGCGN (SEQ ID No. 9), NCGNCG (SEQ ID No. 10), NNCGCG (SEQ ID No. 11), CGCGCG (SEQ ID No. 12);
    group II: CGNNNNN (SEQ ID No. 13), NCGNNNN (SEQ ID No. 14), NNCGNNN (SEQ ID No. 15), NNNCGNN (SEQ ID No. 16), NNNNCGN (SEQ ID No. 17), NNNNNCG (SEQ ID No. 18), CGCGNNN (SEQ ID No. 19), CGNCGNN (SEQ ID No. 20), CGNNCGN (SEQ ID No. 21), CGNNNCG (SEQ ID No. 22), NCGCGNN (SEQ ID No. 23), NCGNCGN (SEQ ID No. 24), NCGNNCG (SEQ ID No. 25), NNCGCGN (SEQ ID No. 26), NNCGNCG (SEQ ID No. 27), NNNCGCG (SEQ ID No. 28), CGCGCGN (SEQ ID No. 29), CGCGNCG (SEQ ID No. 30), CGNCGCG (SEQ ID No. 31), NCGCGCG (SEQ ID No. 32);
    group III: CGNNNNNN (SEQ ID No. 33), NCGNNNNN (SEQ ID No. 34), NNCGNNNN (SEQ ID No. 35), NNNCGNNN (SEQ ID No. 36), NNNNCGNN (SEQ ID No. 37), NNNNNCGN (SEQ ID No. 38), NNNNNNCG (SEQ ID No. 39), CGCGNNNN (SEQ ID No. 40), CGNCGNNN (SEQ ID No. 41), CGNNCGNN (SEQ ID No. 42), CGNNNCGN (SEQ ID No. 43), CGNNNNCG (SEQ ID No. 44), NCGCGNNN (SEQ ID No. 45), NCGNCGNN (SEQ ID No. 46), NCGNNCGN (SEQ ID No. 47), NCGNNNCG (SEQ ID No. 48), NNCGCGNN (SEQ ID No. 49), NNCGNCGN (SEQ ID No. 50), NNCGNNCG (SEQ ID No. 51), NNNCGCGN (SEQ ID No. 52), NNNCGNCG (SEQ ID No. 53), NNNNCGCG (SEQ ID No. 54), CGCGCGNN (SEQ ID No. 55), CGCGNCGN (SEQ ID No. 56), CGCGNNCG (SEQ ID No. 57), CGNCGCGN (SEQ ID No. 58), CGNCGNCG (SEQ ID No. 59), CGNNCGCG (SEQ ID No. 60), NCGCGCGN (SEQ ID No. 61), NCGCGNCG (SEQ ID No. 62), NCGNCGCG (SEQ ID No. 63), NNCGCGCG (SEQ ID No. 64), CGCGCGCG (SEQ ID No. 65);

wherein N is any nucleotide, preferably A, T, G, C or U.

Embodiment 27

A kit for DNA amplification, comprising:
at least one polymerase; and
at least one k-mer comprising in its sequence at least the sequence CG at any location of the k-mer sequence.

Embodiment 28

The kit of embodiment 26 or 27, further comprising a multitude of nucleotides.

Embodiment 29

The kit of any one of embodiments 26 to 28, wherein the at least one polymerase is 029 DNA polymerase.

Embodiment 30

The data base of embodiment 13 or 14, wherein at least one k-mer in the multitude of k-mers is a k-mer having a nucleotide sequence selected from the following groups I, II and/or III:

group I: CGNNNN (SEQ ID No. 1), NCGNNN (SEQ ID No. 2), NNCGNN (SEQ ID No. 3), NNNCGN (SEQ ID No. 4), NNNNCG (SEQ ID No. 5), CGCGNN (SEQ ID No. 6), CGNCGN (SEQ ID No. 7), CGNNCG (SEQ ID No. 8), NCGCGN (SEQ ID No. 9), NCGNCG (SEQ ID No. 10), NNCGCG (SEQ ID No. 11), CGCGCG (SEQ ID No. 12);

group II: CGNNNNN (SEQ ID No. 13), NCGNNNN (SEQ ID No. 14), NNCGNNN (SEQ ID No. 15), NNNCGNN (SEQ ID No. 16), NNNNCGN (SEQ ID No. 17), NNNNNCG (SEQ ID No. 18), CGCGNNN (SEQ ID No. 19), CGNCGNN (SEQ ID No. 20), CGNNCGN (SEQ ID No. 21), CGNNNCG (SEQ ID No. 22), NCGCGNN (SEQ ID No. 23), NCGNCGN (SEQ ID No. 24), NCGNNCG (SEQ ID No. 25), NNCGCGN (SEQ ID No. 26), NNCGNCG (SEQ ID No. 27), NNNCGCG (SEQ ID No. 28), CGCGCGN (SEQ ID No. 29), CGCGNCG (SEQ ID No. 30), CGNCGCG (SEQ ID No. 31), NCGCGCG (SEQ ID No. 32);

group III: CGNNNNNN (SEQ ID No. 33), NCGNNNNN (SEQ ID No. 34), NNCGNNNN (SEQ ID No. 35), NNNCGNNN (SEQ ID No. 36), NNNNCGNN (SEQ ID No. 37), NNNNNCGN (SEQ ID No. 38), NNNNNNCG (SEQ ID No. 39), CGCGNNNN (SEQ ID No. 40), CGNCGNNN (SEQ ID No. 41), CGNNCGNN (SEQ ID No. 42), CGNNNCGN (SEQ ID No. 43), CGNNNNCG (SEQ ID No. 44), NCGCGNNN (SEQ ID No. 45), NCGNCGNN (SEQ ID No. 46), NCGNNCGN (SEQ ID No. 47), NCGNNNCG (SEQ ID No. 48), NNCGCGNN (SEQ ID No. 49), NNCGNCGN (SEQ ID No. 50), NNCGNNCG (SEQ ID No. 51), NNNCGCGN (SEQ ID No. 52), NNNCGNCG (SEQ ID No. 53), NNNNCGCG (SEQ ID No. 54), CGCGCGNN (SEQ ID No. 55), CGCGNCGN (SEQ ID No. 56), CGCGNNCG (SEQ ID No. 57), CGNCGCGN (SEQ ID No. 58), CGNCGNCG (SEQ ID No. 59), CGNNCGCG (SEQ ID No. 60), NCGCGCGN (SEQ ID No. 61), NCGCGNCG (SEQ ID No. 62), NCGNCGCG (SEQ ID No. 63), NNCGCGCG (SEQ ID No. 64), CGCGCGCG (SEQ ID No. 65);

wherein N is any nucleotide, preferably A, T, G, C or U.

Embodiment 31

The data base of embodiment 13 or 14, wherein at least one k-mer in the multitude of k-mers is a k-mer comprising in its sequence at least the sequence CG at any location of the k-mer sequence.

EXAMPLES

The present invention will now be described in detail with reference to several examples thereof. However, these examples are illustrative and do not limit the scope of the invention.

A blood sample of a human suffering from sepsis was provided, and an enrichment of the DNA sequences of specific microorganisms and viruses was carried out. The microorganisms and virus as well as the data base for obtaining the respective genome thereof are given in the following Table 1.

TABLE 1

| Organisms and genome data used | | |
|---|---|---|
| Organism | Full Name | NCBI Acc. No. |
| *Escherichia coli* | *E. coli* str. K12 substr. MC4100 | HG738867.1 |
| *Staphylococcus aureus* | *S. aureus* subsp. *aureus* MRSA252 | BX571856.1 |
| *Pandoravirus salinus* | *Pandoravirus salinus* | NC 022098.1 |

The data base entries are hereby as follows:
NCBI Acc. No. HG738867.1:
MYMC4100
Organism name: *Escherichia coli* str. K-12 substr. MC4100 (*E. coli*) Infraspecific name: Strain: K-12 substr. MC4100 BioSample: SAMEA3138816 Submitter: EVO-ECOGENKIEL Date: 2013 Nov. 6 Assembly level: Complete Genome Genome representation: full GenBank assembly accession: GCA_000499485.1 (latest) RefSeq assembly accession: GCF_000499485.1 (latest) RefSeq assembly and GenBank assembly identical: yes NCBI Acc. No. BX571856.1:
ASM1150v1
Organism name: *Staphylococcus aureus* subsp. *aureus* MRSA252 (firmicutes) Infraspecific name: Strain: MRSA252 BioSample: SAMEA1705935 Submitter: Sanger Institute Date: 2004 Jun. 25 Assembly level: Complete Genome Genome representation: full GenBank assembly accession: GCA_000011505.1 (latest) RefSeq assembly accession: GCF_000011505.1 (latest) RefSeq assembly and GenBank assembly identical: yes NCBI Acc. No. NC 022098.1:
ViralProj215788

Organism name: Pandoravirus salinus (viruses) Submitter: NCBI RefSeq Genome Project Date: 2013 Jun. 28 Assembly level: Complete Genome Genome representation: full GenBank assembly accession: n/a RefSeq assembly accession: GCF_000911955.1 (latest) RefSeq assembly and GenBank assembly identical: n/a For the human genome, the following was used: *Homo sapiens* hs37d5, i.e. the reference assembly sequence hs37d5 of the 1000 Genomes Project, available at ftp://ftp.1000genomes.ebi.ac.uk/vol1/ftp/technical/reference/phase2 reference assembly sequence/hs37d5ss.fa.gz The genomes of the microorganisms were compared with the human genome, and several k-mers that were comparatively enriched in respect to the genome size in the microorganisms and virus compared to the human genome were found, as determined by the comparison of the genomes. In brief, the respective genomes were downloaded from NCBI Genbank or via the ftp access of the 1000 genomes project. Next, all occurring k-mers with a range of k=4-11 were determined, counted and divided by the total sum of k-mers occurring within the respective genome. Subsequently, k-mer frequencies of the non-human genomes were divided by k-mer frequencies of the human genome to determine the k-mer enrichment. To account for extreme values especially occurring in higher k-mers, i.e., an 11-mer occurring only once in a bacterium but not in human were rejected due to an anticipated poor performance during an amplification. Hence, a filter was applied to select for k-mer occurring at least 10 times per genome.

An example for the best 100 octamers for the three microorganism and virus in relation to the human DNA is found in the following Table 2.

TABLE 2

Top 100 8-mers and their enrichment (fold) compared to human DNA in three different organisms (compared to human DNA), sorted by mean (*E. coli, S. Aureus*).

| k-mer | Bacteria | | Viruses |
|---|---|---|---|
| | E. coli | S. aureus | Pandoravirus salinus |
| CGACGATA (SEQ ID No. 87) | 170 | 98 | 168 |
| GCGCGTAA (SEQ ID No. 88) | 255 | 46 | 117 |
| ATTACGCG (SEQ ID No. 89) | 190 | 61 | 43 |
| CGTCGATA (SEQ ID No. 90) | 186 | 59 | 170 |
| CGATAACG (SEQ ID No. 91) | 199 | 49 | 50 |
| CGCGATAA (SEQ ID No. 92) | 194 | 47 | 52 |
| CGATACCG (SEQ ID No. 93) | 261 | 34 | 120 |
| CGCCGATA (SEQ ID No. 94) | 212 | 37 | 126 |
| TATCGCGA (SEQ ID No. 95) | 152 | 48 | 61 |
| CGCGTAAA (SEQ ID No. 96) | 172 | 41 | 98 |
| ATCGTCGC (SEQ ID No. 97) | 137 | 45 | 393 |
| CGGCGATA (SEQ ID No. 98) | 239 | 26 | 120 |
| CGATACGC (SEQ ID No. 99) | 197 | 30 | 159 |
| ATCGCGAT (SEQ ID No. 100) | 170 | 34 | 116 |
| CGGTACGC (SEQ ID No. 101) | 336 | 16 | 176 |
| ATTGCGCG (SEQ ID No. 102) | 157 | 33 | 261 |
| AATCGACG (SEQ ID No. 103) | 102 | 49 | 115 |
| CGATAGCG (SEQ ID No. 104) | 169 | 28 | 120 |
| CGTTACGC (SEQ ID No. 105) | 197 | 24 | 28 |
| ATAACGCG (SEQ ID No. 106) | 143 | 32 | 19 |
| CGCGATAC (SEQ ID No. 107) | 174 | 26 | 148 |
| CGCGAATA (SEQ ID No. 108) | 147 | 31 | 30 |
| TCGCGTAA (SEQ ID No. 109) | 131 | 34 | 33 |
| AACGCGAT (SEQ ID No. 110) | 105 | 42 | 31 |
| ATTTCGCG (SEQ ID No. 111) | 119 | 36 | 53 |
| CGTATCGA (SEQ ID No. 112) | 88 | 49 | 83 |
| ATCGACGA (SEQ ID No. 113) | 109 | 39 | 308 |
| CGTACCGA (SEQ ID No. 114) | 160 | 26 | 88 |
| TCGCGAAA (SEQ ID No. 115) | 117 | 35 | 99 |
| ATACGCGC (SEQ ID No. 116) | 121 | 34 | 143 |
| CGATATCG (SEQ ID No. 117) | 114 | 36 | 63 |
| CGTAAACG (SEQ ID No. 118) | 98 | 41 | 18 |
| CGACGATC (SEQ ID No. 119) | 134 | 30 | 475 |
| CGATTACG (SEQ ID No. 120) | 97 | 40 | 49 |
| AATCGTCG (SEQ ID No. 121) | 82 | 47 | 149 |
| CGCCGTTA (SEQ ID No. 122) | 162 | 23 | 37 |
| ATCGACGC (SEQ ID No. 123) | 136 | 28 | 365 |
| CGGCGTAA (SEQ ID No. 124) | 206 | 18 | 51 |
| CGTATCGC (SEQ ID No. 125) | 122 | 30 | 120 |
| ATCGCGAA (SEQ ID No. 126) | 124 | 29 | 43 |
| TACGACGA (SEQ ID No. 127) | 66 | 55 | 106 |
| ATATCGCG (SEQ ID No. 128) | 120 | 30 | 38 |
| ACGCGATA (SEQ ID No. 129) | 96 | 37 | 61 |
| GCGTCGTA (SEQ ID No. 130) | 85 | 42 | 153 |
| CGATTGCG (SEQ ID No. 131) | 87 | 40 | 143 |
| CGGTAACG (SEQ ID No. 132) | 164 | 21 | 11 |
| ATTCGTCG (SEQ ID No. 133) | 77 | 45 | 91 |

TABLE 2-continued

Top 100 8-mers and their enrichment (fold) compared to human DNA in three different organisms (compared to human DNA), sorted by mean (*E. coli, S. Aureus*).

| | Bacteria | | Viruses |
|---|---|---|---|
| k-mer | *E. coli* | *S. aureus* | *Pandoravirus salinus* |
| CGCGTCGA (SEQ ID No. 134) | 158 | 22 | 1148 |
| GCGCGATA (SEQ ID No. 135) | 172 | 20 | 124 |
| CGCGATTA (SEQ ID No. 136) | 110 | 30 | 30 |
| ACGCGTAA (SEQ ID No. 137) | 91 | 36 | 20 |
| CGTTACGA (SEQ ID No. 138) | 70 | 47 | 18 |
| TACGCGCA (SEQ ID No. 139) | 114 | 29 | 91 |
| CGCGTAAC (SEQ ID No. 140) | 141 | 23 | 28 |
| CGTACCGC (SEQ ID No. 141) | 163 | 20 | 112 |
| ATCGCGCG (SEQ ID No. 142) | 177 | 18 | 528 |
| CGTCGTAA (SEQ ID No. 143) | 63 | 50 | 45 |
| AATACGCG (SEQ ID No. 144) | 113 | 27 | 44 |
| ATCGGCGA (SEQ ID No. 145) | 134 | 23 | 194 |
| CGCGAAAA (SEQ ID No. 146) | 130 | 23 | 192 |
| TACGCGAA (SEQ ID No. 147) | 86 | 35 | 23 |
| ACGTATCG (SEQ ID No. 148) | 52 | 58 | 30 |
| GTACGCGA (SEQ ID No. 149) | 111 | 27 | 85 |
| ATTCGCGA (SEQ ID No. 150) | 107 | 28 | 39 |
| ACGACGAT (SEQ ID No. 151) | 56 | 53 | 231 |
| CGCGAACG (SEQ ID No. 152) | 159 | 19 | 63 |
| CGCGACGA (SEQ ID No. 153) | 166 | 18 | 771 |
| CGCGACAA (SEQ ID No. 154) | 107 | 27 | 307 |
| CGTAACGA (SEQ ID No. 155) | 72 | 40 | 11 |
| ATTCGCGC (SEQ ID No. 156) | 156 | 18 | 150 |
| ATCGTCGA (SEQ ID No. 157) | 79 | 36 | 228 |
| ATCGACGG (SEQ ID No. 158) | 124 | 23 | 257 |
| CCGCGATA (SEQ ID No. 159) | 136 | 21 | 54 |
| ACGAATCG (SEQ ID No. 160) | 50 | 57 | 74 |
| ACGACGCG (SEQ ID No. 161) | 132 | 21 | 540 |
| CGAATACG (SEQ ID No. 162) | 81 | 35 | 54 |
| AGCGCGTA (SEQ ID No. 163) | 103 | 27 | 71 |
| ATCGTTCG (SEQ ID No. 164) | 59 | 47 | 17 |
| GCGCGTTA (SEQ ID No. 165) | 192 | 14 | 21 |
| ATGCGACG (SEQ ID No. 166) | 107 | 25 | 192 |
| GTCGCGTA (SEQ ID No. 167) | 104 | 26 | 130 |
| ACGCGCAA (SEQ ID No. 168) | 109 | 25 | 197 |
| ACGATACG (SEQ ID No. 169) | 64 | 41 | 51 |
| TCGCGCAA (SEQ ID No. 170) | 122 | 22 | 212 |
| AATGCGCG (SEQ ID No. 171) | 121 | 22 | 129 |
| CGCGGTAA (SEQ ID No. 172) | 130 | 20 | 40 |
| CGGTACGA (SEQ ID No. 173) | 88 | 29 | 108 |
| TACCGCGA (SEQ ID No. 174) | 124 | 21 | 76 |
| AACGCGTA (SEQ ID No. 175) | 71 | 36 | 16 |
| ATACGCCG (SEQ ID No. 176) | 120 | 21 | 98 |
| CGACGGTA (SEQ ID No. 177) | 128 | 20 | 99 |
| CCGATACG (SEQ ID No. 178) | 85 | 29 | 102 |
| GCGCGAAA (SEQ ID No. 179) | 167 | 15 | 211 |
| CGTCGTTA (SEQ ID No. 180) | 74 | 33 | 17 |
| TGCGCGAA (SEQ ID No. 181) | 166 | 15 | 91 |
| CGTCAACG (SEQ ID No. 182) | 84 | 29 | 147 |
| TCGACGAA (SEQ ID No. 183) | 88 | 26 | 88 |
| CGCGCATA (SEQ ID No. 184) | 94 | 25 | 169 |
| CGTCGTAC (SEQ ID No. 185) | 59 | 39 | 179 |
| CGTTGCGA (SEQ ID No. 186) | 71 | 32 | 119 |

Similar results can be obtained for other k-mers.

Figure 2:
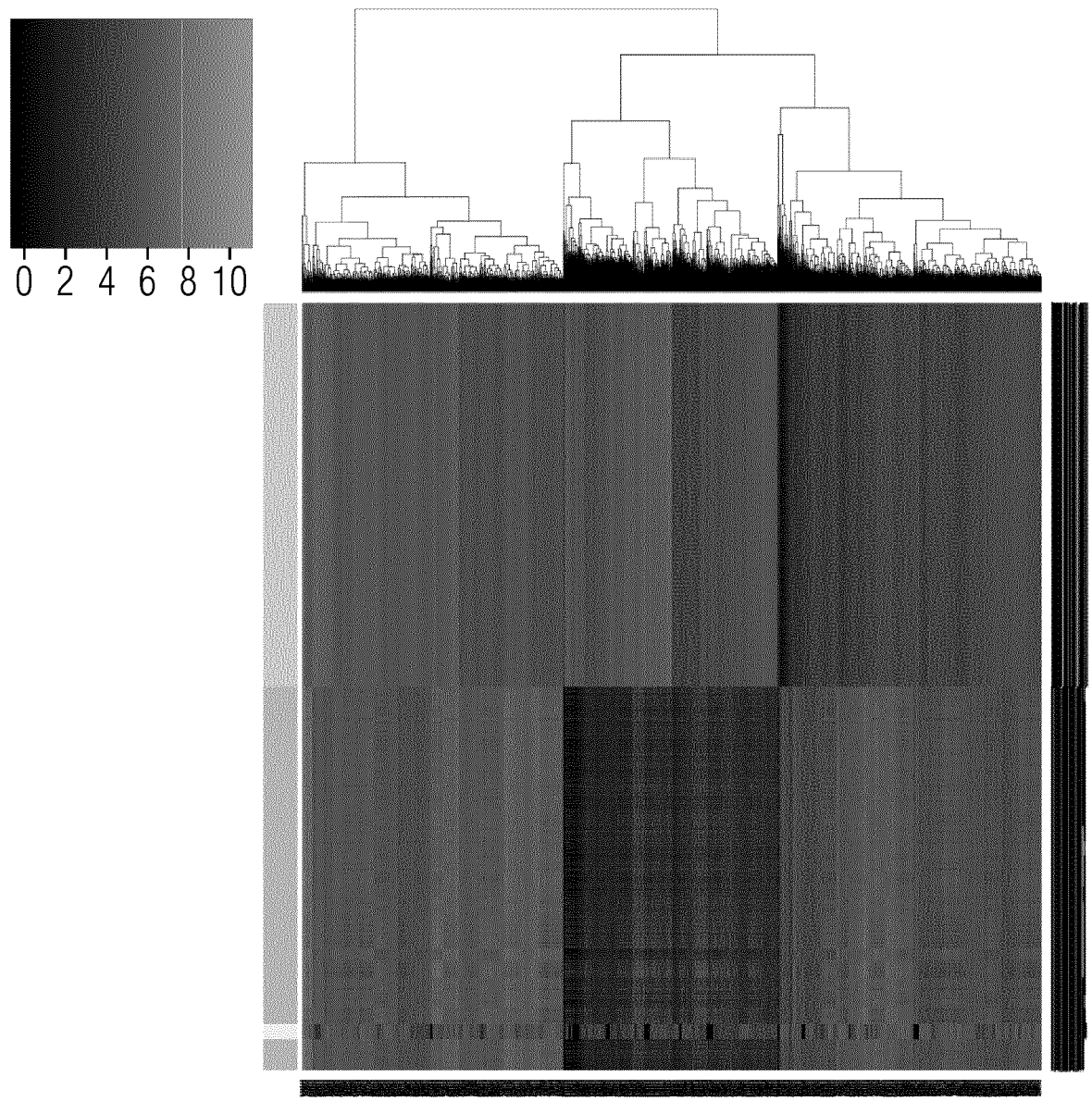
FIG. 2 depicts a heatmap of hexamer frequencies in an example of the invention.

For example, FIGS. 1 and 2 depict strong differences in k-mer frequencies between the human genome and the genome of the facultative pathogen *Escherichia coli* for specific hexamers.

FIG. 1 shows global differences in hexamer frequencies visualized by principle component analysis (PCA), with the axes given for specific principle components (PC). The example shows *E. coli* hexamers in the left bottom of the figure and human DNA on the right. Mitochondrial DNA forms a cluster at x=PC1(53.2%) being about 20 and y=PC2 (15.8%) being about −5 to −10.

FIG. 2 shows a heatmap of hexamer frequencies between *E. coli* (top; light gray part of the bar on the left) and Human DNA (bottom). Mitochondrial DNA is marked in a small stripe (white stripe on the left) at the bottom. The heatmap colors is based on a logarithmic scale. Black means low frequency and light gray means high frequency.

The best 100 hexamers and heptamers and their average enrichment for the two microorganisms and the virus in relation to the human DNA are found in the following Tables 3 and 4.

TABLE 3

Top 100 6-mers and their average enrichment compared to human DNA for three different organisms, i.e. *E. coli*, *S. Aureus* and *Pandoravirus salinus*

| k-mer | | Enrichment |
|---|---|---|
| CGTCGA | (SEQ ID No. 187) | 133.6 |
| CGACGA | (SEQ ID No. 188) | 126.7 |
| CGACGC | (SEQ ID No. 189) | 94.1 |
| CGATCG | (SEQ ID No. 190) | 91.7 |
| CGTCGC | (SEQ ID No. 191) | 82.5 |
| ACGACG | (SEQ ID No. 192) | 77.4 |
| CGCGAC | (SEQ ID No. 193) | 75.2 |
| CGACCG | (SEQ ID No. 194) | 71.6 |
| CGCCGA | (SEQ ID No. 195) | 66 |
| ACGTCG | (SEQ ID No. 196) | 57.3 |
| TCGCGA | (SEQ ID No. 197) | 50.8 |
| ACGCGC | (SEQ ID No. 198) | 47.9 |
| CGCGTA | (SEQ ID No. 199) | 47.5 |
| GTCGAC | (SEQ ID No. 200) | 47.5 |
| ACGCGA | (SEQ ID No. 201) | 42.6 |
| CGCGAA | (SEQ ID No. 202) | 41.8 |
| AACGCG | (SEQ ID No. 203) | 35.3 |
| CGTACG | (SEQ ID No. 204) | 33.1 |
| GACGAC | (SEQ ID No. 205) | 32.3 |
| ACGCGT | (SEQ ID No. 206) | 30.4 |
| CGAACG | (SEQ ID No. 207) | 25.8 |
| ATCGAC | (SEQ ID No. 208) | 23.6 |
| ATCGCG | (SEQ ID No. 209) | 21.5 |
| GCGCAA | (SEQ ID No. 210) | 19.1 |
| CGCCAA | (SEQ ID No. 211) | 17.8 |
| CGACAA | (SEQ ID No. 212) | 17.6 |
| ATGCGC | (SEQ ID No. 213) | 16.6 |
| GTCGCA | (SEQ ID No. 214) | 16.2 |
| CGATGC | (SEQ ID No. 215) | 15.8 |
| GCGTAC | (SEQ ID No. 216) | 15.3 |
| ACGACC | (SEQ ID No. 217) | 15.1 |
| GCGGTA | (SEQ ID No. 218) | 15 |
| CAACGC | (SEQ ID No. 219) | 14.9 |
| TGCGCA | (SEQ ID No. 220) | 14.6 |
| ATCGTC | (SEQ ID No. 221) | 14.3 |
| CGCAAC | (SEQ ID No. 222) | 14.3 |
| CATCGC | (SEQ ID No. 223) | 14.3 |
| CGATAC | (SEQ ID No. 224) | 14.1 |
| CGCATC | (SEQ ID No. 225) | 14.1 |
| TCGACA | (SEQ ID No. 226) | 14.1 |
| GCGATA | (SEQ ID No. 227) | 14 |
| AGCGAC | (SEQ ID No. 228) | 12.9 |
| CGATAA | (SEQ ID No. 229) | 12.7 |
| CGTTGC | (SEQ ID No. 230) | 12.6 |
| GCGTCA | (SEQ ID No. 231) | 12.6 |
| GCGAAC | (SEQ ID No. 232) | 12.5 |
| AACGCC | (SEQ ID No. 233) | 12.4 |
| ATGTCG | (SEQ ID No. 234) | 12.2 |
| CGGTAC | (SEQ ID No. 235) | 12.1 |
| CAATCG | (SEQ ID No. 236) | 12 |
| TATCGA | (SEQ ID No. 237) | 12 |
| CGCAAA | (SEQ ID No. 238) | 12 |
| ACCGAT | (SEQ ID No. 239) | 11.7 |
| AAGCGC | (SEQ ID No. 240) | 11.6 |
| GCGCTA | (SEQ ID No. 241) | 11.4 |
| GTCGTA | (SEQ ID No. 242) | 11.2 |
| CCGATA | (SEQ ID No. 243) | 11.1 |
| GCGTAA | (SEQ ID No. 244) | 11.1 |
| CATCGA | (SEQ ID No. 245) | 11 |
| GGCGTA | (SEQ ID No. 246) | 10.9 |
| ATTCGC | (SEQ ID No. 247) | 10.8 |
| ATCGAT | (SEQ ID No. 248) | 10.7 |
| CGTCAA | (SEQ ID No. 249) | 10.7 |
| AACGAC | (SEQ ID No. 250) | 10.6 |
| ATATCG | (SEQ ID No. 251) | 10.6 |
| ACGACA | (SEQ ID No. 252) | 10.5 |
| CGATGA | (SEQ ID No. 253) | 10.1 |
| ATACCG | (SEQ ID No. 254) | 10.1 |
| CGCTAC | (SEQ ID No. 255) | 9.8 |
| AATGCG | (SEQ ID No. 256) | 9.7 |
| TCGCAA | (SEQ ID No. 257) | 9.6 |
| GTCGAA | (SEQ ID No. 258) | 9.5 |
| CAACGA | (SEQ ID No. 259) | 9.5 |

TABLE 3-continued

Top 100 6-mers and their average enrichment compared to human DNA for three different organisms, i.e. *E. coli*, *S. Aureus* and *Pandoravirus salinus*

| k-mer | | Enrichment |
|---|---|---|
| ATTGCG | (SEQ ID No. 260) | 9.3 |
| CGTTGA | (SEQ ID No. 261) | 9.3 |
| CGATCA | (SEQ ID No. 262) | 9.3 |
| TCGTCA | (SEQ ID No. 263) | 9.2 |
| GCGAAA | (SEQ ID No. 264) | 9.2 |
| ATACGC | (SEQ ID No. 265) | 9 |
| TACCGA | (SEQ ID No. 266) | 9 |
| ATGCGA | (SEQ ID No. 267) | 8.9 |
| CGTACC | (SEQ ID No. 268) | 8.8 |
| AAAGCG | (SEQ ID No. 269) | 8.7 |
| ATGACG | (SEQ ID No. 270) | 8.7 |
| GTACGA | (SEQ ID No. 271) | 8.5 |
| CGAAAA | (SEQ ID No. 272) | 8.5 |
| ACGATA | (SEQ ID No. 273) | 8.5 |
| CGGATA | (SEQ ID No. 274) | 8.5 |
| CGGTTA | (SEQ ID No. 275) | 8.4 |
| AGTCGA | (SEQ ID No. 276) | 8.3 |
| CGACTA | (SEQ ID No. 277) | 8.2 |
| CGCATA | (SEQ ID No. 278) | 8.1 |
| ACGCAA | (SEQ ID No. 279) | 8.1 |
| ATAGCG | (SEQ ID No. 280) | 8.1 |
| GACGAA | (SEQ ID No. 281) | 8 |
| AACGGT | (SEQ ID No. 282) | 8 |
| ACAACG | (SEQ ID No. 283) | 7.9 |
| CGATAG | (SEQ ID No. 284) | 7.7 |
| ACATCG | (SEQ ID No. 285) | 7.7 |
| ACGATG | (SEQ ID No. 286) | 7.7 |

TABLE 4

Top 100 7-mers and their average enrichment compared to human DNA for three different organisms, i.e. *E. coli*, *S. Aureus* and *Pandoravirus salinus*

| k-mer | | Enrichment |
|---|---|---|
| CGTCGAC | (SEQ ID No. 287) | 258.8 |
| CGACGAC | (SEQ ID No. 288) | 236.6 |
| CGCGACG | (SEQ ID No. 289) | 184.7 |
| CGACGCG | (SEQ ID No. 290) | 172 |
| GCGTCGA | (SEQ ID No. 291) | 165.7 |
| TCGACGA | (SEQ ID No. 292) | 152.2 |
| CGCGCGA | (SEQ ID No. 293) | 142 |
| CGTCGTC | (SEQ ID No. 294) | 139.8 |
| GCGACGA | (SEQ ID No. 295) | 135.7 |
| CCGTCGA | (SEQ ID No. 296) | 135.5 |
| ATCGTCG | (SEQ ID No. 297) | 134.7 |
| ATCGACG | (SEQ ID No. 298) | 133.3 |
| CGGTCGA | (SEQ ID No. 299) | 126.4 |
| CGTCGAG | (SEQ ID No. 300) | 119.2 |
| CGCGCAA | (SEQ ID No. 301) | 119 |
| ATCGGCG | (SEQ ID No. 302) | 115.9 |
| ACGACGA | (SEQ ID No. 303) | 115.9 |
| CGATCGA | (SEQ ID No. 304) | 115.8 |
| CCGACGA | (SEQ ID No. 305) | 112.7 |
| CGATCGC | (SEQ ID No. 306) | 103.6 |
| ATCGCCG | (SEQ ID No. 307) | 96.6 |
| CGACCGA | (SEQ ID No. 308) | 91.1 |
| ACGTCGA | (SEQ ID No. 309) | 90.4 |
| CGACGTC | (SEQ ID No. 310) | 88.6 |
| ACGACGC | (SEQ ID No. 311) | 85.5 |
| CGGTACG | (SEQ ID No. 312) | 84.8 |
| ACCGACG | (SEQ ID No. 313) | 82.8 |
| CGCGATA | (SEQ ID No. 314) | 82.7 |
| CCGATCG | (SEQ ID No. 315) | 82.7 |
| ACCGTCG | (SEQ ID No. 316) | 82.4 |
| TCGCGCA | (SEQ ID No. 317) | 80.4 |
| GCGCGTA | (SEQ ID No. 318) | 78.4 |
| CGACGAG | (SEQ ID No. 319) | 78.4 |
| ACGCGAC | (SEQ ID No. 320) | 78.3 |
| CGACCGC | (SEQ ID No. 321) | 77.8 |
| CGCGACA | (SEQ ID No. 322) | 76.8 |
| TCGCCGA | (SEQ ID No. 323) | 76.8 |
| GTCGCGA | (SEQ ID No. 324) | 76.1 |
| CGCGAAA | (SEQ ID No. 325) | 75.4 |
| CGGCGTA | (SEQ ID No. 326) | 74.6 |

TABLE 4-continued

Top 100 7-mers and their average enrichment compared to human DNA for three different organisms, i.e. *E. coli*, *S. Aureus* and *Pandoravirus salinus*

| k-mer | | Enrichment |
|---|---|---|
| GACGCGC | (SEQ ID No. 327) | 74.1 |
| GCGCCGA | (SEQ ID No. 328) | 73.3 |
| CGCAACG | (SEQ ID No. 329) | 73 |
| CGCACGA | (SEQ ID No. 330) | 72.6 |
| ACGACCG | (SEQ ID No. 331) | 71.7 |
| CGCGTAA | (SEQ ID No. 332) | 71.2 |
| CGATACG | (SEQ ID No. 333) | 70.9 |
| ACGGTCG | (SEQ ID No. 334) | 70.5 |
| ATGCGCG | (SEQ ID No. 335) | 70.4 |
| CGTCGCA | (SEQ ID No. 336) | 69.5 |
| ACGACGG | (SEQ ID No. 337) | 68.1 |
| ACGTCGC | (SEQ ID No. 338) | 67.5 |
| ACGCCGA | (SEQ ID No. 339) | 67.4 |
| ACGATCG | (SEQ ID No. 340) | 67 |
| ACGGCGA | (SEQ ID No. 341) | 66.1 |
| CGCCGTA | (SEQ ID No. 342) | 65 |
| CGACGAA | (SEQ ID No. 343) | 64.9 |
| ATCGCGA | (SEQ ID No. 344) | 63.3 |
| CGACGCA | (SEQ ID No. 345) | 62.5 |
| GCGCGAA | (SEQ ID No. 346) | 62.2 |
| CGAACCG | (SEQ ID No. 347) | 61.6 |
| CGTCGTA | (SEQ ID No. 348) | 58.8 |
| CGACACG | (SEQ ID No. 349) | 58.7 |
| AGCGTCG | (SEQ ID No. 350) | 58 |
| CGATGCG | (SEQ ID No. 351) | 56.4 |
| CGCTACG | (SEQ ID No. 352) | 55.8 |
| CGCCGAA | (SEQ ID No. 353) | 55 |
| TACGCGA | (SEQ ID No. 354) | 53.2 |
| AACGCGC | (SEQ ID No. 355) | 52.8 |
| ATTCGCG | (SEQ ID No. 356) | 52.3 |
| CGCGTAC | (SEQ ID No. 357) | 51.2 |
| AACGGCG | (SEQ ID No. 358) | 50.8 |
| ACGCGCT | (SEQ ID No. 359) | 50.7 |
| CACGACG | (SEQ ID No. 360) | 50.6 |
| TCGCGAA | (SEQ ID No. 361) | 50.3 |
| CGTCGAA | (SEQ ID No. 362) | 50 |
| CGCTCGA | (SEQ ID No. 363) | 49.8 |
| ACGCGCA | (SEQ ID No. 364) | 49.7 |
| CGTACGC | (SEQ ID No. 365) | 49.4 |
| CATCGCG | (SEQ ID No. 366) | 49.1 |
| CGTGCGA | (SEQ ID No. 367) | 48.9 |
| CGAATCG | (SEQ ID No. 368) | 48.7 |
| CGACTCG | (SEQ ID No. 369) | 48.1 |
| AATCGCG | (SEQ ID No. 370) | 48 |
| CAACGCG | (SEQ ID No. 371) | 47.2 |
| ACGAGCG | (SEQ ID No. 372) | 47.2 |
| ATACGCG | (SEQ ID No. 373) | 47 |
| AACGACG | (SEQ ID No. 374) | 46.9 |
| AAGCGCG | (SEQ ID No. 375) | 46.6 |
| ACGCCGT | (SEQ ID No. 376) | 46.4 |
| CACGTCG | (SEQ ID No. 377) | 46 |
| ATCGCGG | (SEQ ID No. 378) | 45.7 |
| AACGTCG | (SEQ ID No. 379) | 45.4 |
| CGTAACG | (SEQ ID No. 380) | 44.8 |
| CGCGGTA | (SEQ ID No. 381) | 44.6 |
| AGCGCGA | (SEQ ID No. 382) | 44.6 |
| GACGCGA | (SEQ ID No. 383) | 44.1 |
| ACGACGT | (SEQ ID No. 384) | 43.5 |
| CGACGTA | (SEQ ID No. 385) | 43.2 |
| ACGCGTC | (SEQ ID No. 386) | 43.2 |

In addition, the best 100 hexamers found for a comparison of all prokaryotic genomes from NCBIGenbank gene and all human genomes from the 1000 genomes project are given in the following Table 5, together with their average enrichment for all bacteria, including archaea, of the NCBIGenbank.

TABLE 5

Top 100 6-mers found for a comparison of all prokaryotic genomes from NCBIGenbank gene and all human genomes from the 1000 genomes project and their average enrichment

| kmer | | Average Enrichment |
|---|---|---|
| CGTCGA | (SEQ ID No. 387) | 49.9 |
| CGACGA | (SEQ ID No. 388) | 48.7 |
| CGATCG | (SEQ ID No. 389) | 45.4 |

TABLE 5-continued

Top 100 6-mers found for a comparison of all prokaryotic genomes from NCBIGenbank gene and all human genomes from the 1000 genomes project and their average enrichment

| kmer | | Average Enrichment |
|---|---|---|
| CGGCGA | (SEQ ID No. 390) | 36.6 |
| CGCCGA | (SEQ ID No. 391) | 36.6 |
| CGCGAA | (SEQ ID No. 392) | 32.2 |
| CGACCG | (SEQ ID No. 393) | 30.2 |
| CGAACG | (SEQ ID No. 394) | 28.9 |
| TCGCGA | (SEQ ID No. 395) | 28.4 |
| ACGACG | (SEQ ID No. 396) | 26.8 |
| CCGTCG | (SEQ ID No. 397) | 26.0 |
| CGTCGC | (SEQ ID No. 398) | 25.2 |
| CGACGC | (SEQ ID No. 399) | 24.5 |
| ACGCCG | (SEQ ID No. 400) | 23.6 |
| ACGGCG | (SEQ ID No. 401) | 23.4 |
| CGCGAC | (SEQ ID No. 402) | 23.3 |
| CCGACG | (SEQ ID No. 403) | 22.9 |
| CGCGTA | (SEQ ID No. 404) | 22.4 |
| ACGTCG | (SEQ ID No. 405) | 21.5 |
| AACGCG | (SEQ ID No. 406) | 21.3 |
| CCGCGA | (SEQ ID No. 407) | 20.8 |
| ACGCGA | (SEQ ID No. 408) | 20.5 |
| ATCGGC | (SEQ ID No. 409) | 18.6 |
| CGAGCG | (SEQ ID No. 410) | 15.9 |
| CCGGCG | (SEQ ID No. 411) | 15.7 |
| CGTACG | (SEQ ID No. 412) | 15.4 |
| ATCGAC | (SEQ ID No. 413) | 15.3 |
| AGCGCG | (SEQ ID No. 414) | 14.9 |
| CCGCCG | (SEQ ID No. 415) | 14.7 |
| CGCGGA | (SEQ ID No. 416) | 14.4 |
| ATCGCC | (SEQ ID No. 417) | 13.7 |
| CGGCGC | (SEQ ID No. 418) | 13.6 |
| CGCCGC | (SEQ ID No. 419) | 13.5 |
| CGCGCA | (SEQ ID No. 420) | 13.3 |
| GCGAAC | (SEQ ID No. 421) | 13.3 |
| CGCGTC | (SEQ ID No. 422) | 13.2 |
| CGGCAA | (SEQ ID No. 423) | 13.1 |
| CCGATC | (SEQ ID No. 424) | 12.5 |
| CGGACG | (SEQ ID No. 425) | 12.5 |
| GCCGAC | (SEQ ID No. 426) | 12.4 |
| CGCGAG | (SEQ ID No. 427) | 12.3 |
| ACGCGG | (SEQ ID No. 428) | 12.1 |
| GCGGTA | (SEQ ID No. 429) | 12.1 |
| ACGCGC | (SEQ ID No. 430) | 11.9 |
| ACCGGC | (SEQ ID No. 431) | 11.9 |
| ATCGCG | (SEQ ID No. 432) | 11.8 |
| CATCGG | (SEQ ID No. 433) | 11.7 |
| CGATGC | (SEQ ID No. 434) | 11.6 |
| ATGCCG | (SEQ ID No. 435) | 11.4 |
| TCGGCA | (SEQ ID No. 436) | 11.1 |
| GCCGAA | (SEQ ID No. 437) | 11.1 |
| CGCGGC | (SEQ ID No. 438) | 11.1 |
| CGATGA | (SEQ ID No. 439) | 11.1 |
| ATCGTC | (SEQ ID No. 440) | 10.9 |
| ACCGAC | (SEQ ID No. 441) | 10.9 |
| CCGAAC | (SEQ ID No. 442) | 10.8 |
| ACCGCC | (SEQ ID No. 443) | 10.8 |
| GTCGAA | (SEQ ID No. 444) | 10.6 |
| GCGACC | (SEQ ID No. 445) | 10.6 |
| ACCGAT | (SEQ ID No. 446) | 10.6 |
| AACGGC | (SEQ ID No. 447) | 10.6 |
| CATCGA | (SEQ ID No. 448) | 10.6 |
| CATCGC | (SEQ ID No. 449) | 10.5 |
| GCCGTA | (SEQ ID No. 450) | 10.5 |
| GACGAC | (SEQ ID No. 451) | 10.5 |
| CGATAC | (SEQ ID No. 452) | 10.5 |
| CGCCAA | (SEQ ID No. 453) | 10.5 |
| GTCGAC | (SEQ ID No. 454) | 10.4 |
| CCGATA | (SEQ ID No. 455) | 10.4 |
| GACCGC | (SEQ ID No. 456) | 10.4 |
| GGTCGA | (SEQ ID No. 457) | 10.3 |
| CGATCA | (SEQ ID No. 458) | 10.2 |
| CGCATC | (SEQ ID No. 459) | 10.2 |
| CGACCA | (SEQ ID No. 460) | 10.2 |

TABLE 5-continued

Top 100 6-mers found for a comparison of all prokaryotic genomes from NCBIGenbank gene and all human genomes from the 1000 genomes project and their average enrichment

| kmer | | Average Enrichment |
|---|---|---|
| GACGGC | (SEQ ID No. 461) | 10.2 |
| ACCGGT | (SEQ ID No. 462) | 10.2 |
| ATCCGG | (SEQ ID No. 463) | 10.1 |
| ACGCGT | (SEQ ID No. 464) | 9.9 |
| AACGCC | (SEQ ID No. 465) | 9.9 |
| CCGGTA | (SEQ ID No. 466) | 9.9 |
| CGGTAC | (SEQ ID No. 467) | 9.8 |
| AACCGC | (SEQ ID No. 468) | 9.8 |
| CGCACG | (SEQ ID No. 469) | 9.8 |
| GCGGCA | (SEQ ID No. 470) | 9.5 |
| CAACGC | (SEQ ID No. 471) | 9.5 |
| GCGCGA | (SEQ ID No. 472) | 9.5 |
| GCGTAC | (SEQ ID No. 473) | 9.5 |
| CGAACC | (SEQ ID No. 474) | 9.4 |
| GGCGAA | (SEQ ID No. 475) | 9.3 |
| GCTCGA | (SEQ ID No. 476) | 9.2 |
| ACGACC | (SEQ ID No. 477) | 9.1 |
| CGGTCA | (SEQ ID No. 478) | 9.1 |
| GCGATA | (SEQ ID No. 479) | 9.1 |
| CGCAAC | (SEQ ID No. 480) | 9.1 |
| CGAAGC | (SEQ ID No. 481) | 9.0 |
| GCCGGA | (SEQ ID No. 482) | 8.9 |
| GCGGAA | (SEQ ID No. 483) | 8.8 |
| CGACAA | (SEQ ID No. 484) | 8.8 |
| CTTCGC | (SEQ ID No. 485) | 8.7 |
| CAACCG | (SEQ ID No. 486) | 8.7 |

A comparison between Table 3 and Table 5 shows that essentially the hexamers found for the three specific microorganisms and virus can be also found in a much broader database comprising a multitude of prokaryotes, showing that the k-mers are well conserved and homogeneous throughout microorganisms and viruses.

Figure 3:
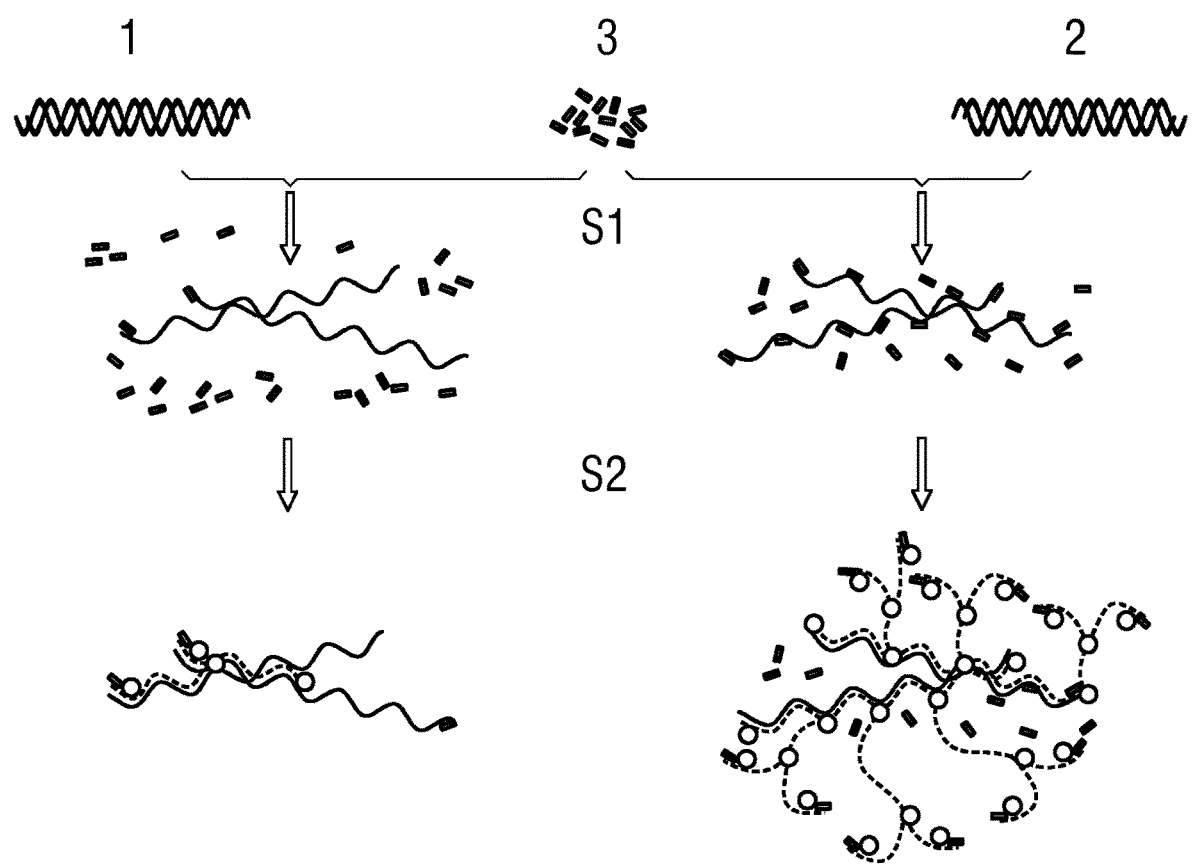
FIG. 3 represents a schematic diagram showing a multiple displacement amplification using the method of the present invention.

The obtained specific k-mers can be used to preferentially amplify bacterial, archaeal, and/or virus DNA from samples with a high human DNA content, e.g., blood, as specifically shown in FIG. 3.

FIG. 3 shows the basic concept of a multiple displacement amplification with the rare hexamers for the microorganisms and virus obtained in the present example—compared to human DNA, which results in a higher amplification for non-human DNA. Human DNA 1 is shown on the left, and the pathogen DNA 2 on the right. The k-mers 3 that are less frequent in the human DNA and obtained in the present method are shown in the middle. They are used in a first step S1 wherein the sample containing both human and pathogen DNA are denatured and hybridized. As shown in the Figure, the k-mers selectively bind more to the pathogen DNA 2. In step S2 MDA, here with 029 DNA polymerase takes place, leading to preferred isothermal amplification with the pathogen DNA on the right, i.e., to an enrichment thereof compared to the human DNA.

Theoretical enrichment factors obtained in the determination step of the comparison of the genomes for specific k-mers of different length for one, two, or three of the microorganisms in the example are shown in Tables 6 to 9, wherein also the mean numbers of binding sites as well as the number of potential k-mers per k-mer length with difference in frequency and/or context to the human genome are shown. To indicate a potential optimum for subsequent amplification based method, k-mers occurring less than 10 times per non-human genome showing an enrichment of less 4 were filtered. In setting with more than 1 non-human organism these criteria applied to all organisms.

TABLE 6 k-mer size dependent enrichment with features determining the performance of a designed multiple displacement amplification in a three organisms, i.e., E. coli, S. aureus, and Pandoravirus salinus, setting compared to a human background.

| k-mer size | Mean binding sites of a single k-mer (per 100 kbp genome) | Mean enrichment of top 20 k-mers (in fold) | Number of qualifying k-mers |
|---|---|---|---|
| 4 | 711 | 8 | 8 |
| 5 | 231 | 17 | 31 |
| 6 | 58 | 63 | 132 |
| 7 | 15 | 131 | 616 |
| 8 | 4 | 215 | 2619 |
| 9 | 1 | 187 | 4882 |
| 10 | 1 | 71 | 518 |
| 11 | 1 | 21 | 5 |

TABLE 7 k-mer size dependent enrichment with features determining the performance of a designed multiple displacement amplification in a two organisms, i.e., E. coli and S. aureus, setting compared to a human background.

| k-mer size | Mean binding sites of a single k-mer (per 100 kbp genome) | Mean enrichment of top 20 k-mers (in fold) | Number of qualifying k-mers |
|---|---|---|---|
| 4 | 613 | 6 | 23 |
| 5 | 174 | 12 | 89 |
| 6 | 44 | 30 | 386 |
| 7 | 11 | 63 | 1579 |
| 8 | 3 | 121 | 5403 |
| 9 | 1 | 195 | 7931 |
| 10 | 1 | 186 | 2674 |
| 11 | 1 | 48 | 74 |

TABLE 8 k-mer size dependent enrichment with features determining the performance of a designed multiple displacement amplification in a two organisms, i.e., E. coli and Pandoravirus salinus, setting compared to a human background.

| k-mer size | Mean binding sites of a single k-mer (per 100 kbp genome) | Mean enrichment of top 20 k-mers (in fold) | Number of qualifying k-mers |
|---|---|---|---|
| 4 | 1103 | 13 | 23 |
| 5 | 329 | 32 | 89 |
| 6 | 83 | 104 | 386 |
| 7 | 22 | 215 | 1592 |
| 8 | 6 | 497 | 6695 |
| 9 | 2 | 1154 | 23852 |
| 10 | 1 | 1464 | 25708 |
| 11 | 1 | 844 | 3653 |

TABLE 9 k-mer size dependent enrichment with features determining the performance of a designed multiple displacement amplification in a one organism, i.e. E. coli, setting compared to a human background.

| k-mer size | Mean binding sites of a single k-mer (per 100 kbp genome) | Mean enrichment of top 20 k-mers (in fold) | Number of qualifying k-mers |
|---|---|---|---|
| 4 | 873 | 9 | 23 |
| 5 | 253 | 19 | 99 |
| 6 | 63 | 51 | 474 |
| 7 | 17 | 107 | 2089 |
| 8 | 4 | 207 | 9214 |
| 9 | 1 | 401 | 38893 |
| 10 | 1 | 1022 | 89522 |
| 11 | 1 | 2593 | 38168 |

To test the theoretical predictions, sets of hexamers were acquired and tested in a MDA enrichment test. The acquired hexamers are listed in Table 10.

TABLE 10

Tested hexamers

| No. | Hexamer |
|---|---|
| 1 | CGNCGN |
| 2 | NCGNCG |
| 3 | CGCGNN |
| 4 | NCGCGN |
| 5 | CGNNCG |
| 6 | NNCGCG |
| 7 | NNGCGC |
| 8 | NNCGGC |
| 9 | NGCGCN |
| 10 | NGCNGC |
| 11 | GCCGNN |
| 12 | GCGCNN |
| 13 | CGNNGC |
| 14 | NCGGCN |
| 15 | CGGCNN |
| 16 | NNGCCG |
| 17 | NGCCGN |
| 18 | NGCNCG |
| 19 | GCNCGN |
| 20 | NCGNGC |
| 21 | CGNGCN |
| 22 | GCNGCN |
| 23 | GCNNGC |
| 24 | GCNNCG |

In Table 8, the IUPAC Ambiguity Codes were applied. Subsequently, N represents A, C, G, T, i.e., each of them, so that accordingly mixtures of different hexamers given in the table with at least one N are obtained.

Exemplary tests with specific selected primer sets are shown in the following. A first k-mer set 1 that was tested contained hexamers 1-24 of Table 8, a second k-mer set 2 hexamers 1-2 of Table 8, and a third k-mer set 3 the hexamers of No. 1. Furthermore, a fourth k-mer set 3A contained the hexamers CGACGN, a fifth k-mer set 5A the hexamer CGACGC, and a sixth k-mer set 5G the k-mer CGGCGC.

For the test, 6000 copies of Human gDNA (genomic DNA) and S. aureus, S. auricularis or E. coli, respectively—so that the final copy number ratio before the amplification is 1:1—were mixed and inserted into the subsequent MDA reaction. The reaction was carried out with 1 mM dNTPs, 50 µM of the respective k-mers and 10 units Phi29 Polymerase for 4 hours at 30° C. After reaction, the mix was incubated at 65° C. for 10 min to inactivate the reaction. Subsequently, the efficacy of the enrichment was determined by qPCR with the 16S rRNA gene of the respective bacterium and the ESR1 gene for human DNA. Additionally the efficacy of the enrichment was determined with the mecA gene of the S. aureus bacterium. As control, the experiment was also once carried out without hexamers. In a comparative example, random hexamers were taken.

Selected results are shown in the following Tables 11, 12 and 13.

TABLE 11

Experiment with E. coli

| k-mer Set | Amplification Human (ESR1 gene) | Amplification E. coli (16S rRNA gene) |
|---|---|---|
| No hexamers | 1.0 | 1.0 |
| Random Hexamers | 76.1 | 6.0 |
| k-mer Set 1 | 2.4 | 3.3 |
| k-mer Set 3 | 18.0 | 111.2 |
| k-mer Set 3A | 29.9 | 548.8 |
| k-mer Set 5A | 7.7 | 8,154.2 |
| k-mer Set 5G | 8.7 | 11,373.1 |

TABLE 12

Experiment with *S. aureus*

| k-mer Set | Amplification Human (ESR1 gene) | Amplification *S. aureus* (16S rRNA gene) | Amplification *S. aureus* (mecA gene) |
|---|---|---|---|
| No hexamers | 1.0 | 1.0 | 1.0 |
| Random Hexamers | 839.5 | 4759.7 | 7625.8 |
| k-mer Set 1 | 3.1 | 14.3 | 43.0 |
| k-mer Set 3 | 99.3 | 315,365.8 | 85,482.0 |
| k-mer Set 3A | 156.5 | 265,190.0 | 151,259.6 |
| k-mer Set 5A | 41.7 | 57,982.6 | 7,400.1 |
| K-mer Set 5G | 68.0 | 229,266.6 | 17,641.3 |

TABLE 13

Experiment with *S. auricularis*

| k-mer Set | Amplification Human (ESR1 gene) | Amplification *S. auricularis* (16S rRNA gene) |
|---|---|---|
| No hexamers | 1.0 | 1.0 |
| Random Hexamers | 91.6 | 312.3 |
| k-mer Set 1 | 2.8 | 7.6 |
| k-mer Set 3 | 26.4 | 18,263.4 |
| k-mer Set 3A | 20.3 | 21,321.2 |
| k-mer Set 5A | 6.9 | 8,861.5 |
| k-mer Set 5G | 10.9 | 15,789.4 |

As can be seen from Tables 11, 12, and 13, a further improvement of the enrichment of the bacterial DNA could be obtained with specific hexamers or hexamer sets as primers.

To test the two k-mer sets 3 and 3A in a realistic clinical setting, a sepsis setting was simulated by spiking bacterial cells into donated EDTA blood from healthy donors. Therefore, 100 cells of both, an *E. coli* and *S. aureus* (MRSA), were spiked into 8 mL of EDTA blood of healthy human donors. The final concentration of each bacterium was 12.5 CFU/mL. Next, DNA was extracted by the Molysis Kit and subsequently subjected into a MDA reaction with k-mer set 3 or 3A. After the reaction (present invention), DNA was prepared by the Oxford Nanopore Sequencing Library Preparation Kit (Ligation Sequencing Kit 1D). Resulting fastq reads were mapped against genomes of *Homo sapiens*, *E. coli*, and *S. aureus* with the BWA-MEM software (version 0.7.11, see Li H. (2013) Aligning sequence reads, clone sequences and assembly contigs with BWA-MEM. arXiv: 1303.3997v1). The resulting sam file was analyzed by the bash scripting language and the software R.

For each pathogen, the starting concentration of cells was 12.5 CFU mL$^{+1}$. On DNA-level this roughly corresponds to 1 DNA base of the respective pathogen in $10^9$ DNA bases of the human DNA. Analysis of the experimental data showed a pathogen DNA concentration between 1.0-3.1 percent, indicating an overall pathogen DNA enrichment of approximately $10^7$ (see relative Basepairs in table 14 regarding the usage of k-mer set 3A and in Table 15 regarding the usage of k-mer set 3). Size selection would further enrich pathogen DNA basepair concentration by a factor of 4-5 giving rise to final DNA concentration of more than 10 percent pathogen concentration.

TABLE 14

Sequencing results with k-mer set 3A. 100 *E. coli* cells + 100 *Staphylococcus* cells in 8 mL of EDTA blood (12.5 cfu/mL for each pathogen) Oxford Nanopore chemistry R9.5; 1D2 protocol

| Parameter | *E. coli* | *S. aureus* | *H. sapiens* |
|---|---|---|---|
| Reads | | | |
| absolute | 11,003 | 8,437 | 1,820,222 |
| relative | 0.6% | 0.5% | 98.9% |
| Basepairs | | | |
| absolute | 37.6 Mbp | 37.3 Mbp | 2.0 Gbp |
| relative | 1.8% | 1.8% | 96.4% |
| Mean cov. (in x-fold) | 8.3 | 13.8 | 0.6 |

TABLE 15

Sequencing results with k-mer set 3. 100 *E. coli* cells + 100 *Staphylococcus* cells in 8 mL of EDTA blood (12.5 cfu/mL for each pathogen) Oxford Nanopore chemistry R9.5; 1D protocol

| Parameter | *E. coli* | *S. aureus* | *H. sapiens* |
|---|---|---|---|
| Reads | | | |
| absolute | 5,836 | 10,881 | 993,995 |
| relative | 0.6% | 1.0% | 98.4% |
| Basepairs | | | |
| absolute | 17.1 Mbp | 50.5 Mbp | 1.6 Gbp |
| relative | 1.0% | 3.1% | 95.9% |
| Mean cov. (in x-fold) | 3.7 | 18.7 | 0.5 |

With the present methods, the distribution of k-mer length and k-mer sequences can be specifically tuned for the intended application based on differences in k-mer frequencies and/or k-mer context in a target nucleic acid from at least one microorganism and/or virus, (e.g., one or more pathogens compared to the unwanted background nucleic acid from a subject, e.g., from human patients).

With the present methods, k-mers are selected on genome-level rather than on a weighted and/or tissue dependent transcriptome-level, leading to improved results.

Nucleic acid sequence, e.g., DNA, fragment produces by the present approach can match current long-read sequencing, e.g., DNA sequencing, technologies.

The present invention enables an improved efficiency in sequence assisted diagnostics, and can particularly lead to higher sensitivity in pathogen detection.

The invention claimed is:

1. A method of selectively amplifying at least one pathogen DNA sequence of at least one microorganism, which is chosen from archaea, bacteria, protists, virus, or fungi, in a sample of a human subject, comprising:
   determining at least one k-mer that shows a difference in frequency or context in the genome of the at least one microorganism compared to the genome of the subject; and
   amplifying the pathogen DNA sequences in the sample using the at least one k-mer determined as primer,
   wherein the at least one k-mer consists of six nucleotides and is enriched in the genome of the at least one microorganism relative to the human genome.

2. The method of claim 1, wherein a multitude of k-mers is determined and used as primers in the amplification of the pathogen DNA sequences in the sample.

3. The method of claim 2, wherein between 5 and 100000 k-mers are determined.

4. The method of claim 3, wherein between 50 and 30000 k-mers are determined.

5. The method of claim 1, wherein the determining of the at least one k-mer that shows a difference in frequency or context in the genome of the at least one microorganism compared to the genome of the subject is carried out using a data base comprising the genome of the subject and the at least one microorganism.

6. The method of claim 1, wherein the amplifying of the pathogen DNA sequences in the sample using the at least one k-mer determined as primer is carried out using isothermal amplification.

7. The method of claim 6, wherein the isothermal amplification is a multiple displacement amplification.

8. A method of selectively amplifying at least one pathogen DNA sequence of at least one microorganism, which is chosen from archaea, bacteria, protists, virus, or fungi, in a sample of a subject, which is a human patient, comprising:
   amplifying the pathogen DNA sequences in the sample using at least one k-mer that shows a difference in frequency or context in the genome of the at least one microorganism compared to the genome of the subject as primer,
   wherein the at least one k-mer consists of six nucleotides and is enriched in the genome of the at least one microorganism relative to the human genome.

9. The method of claim 8, wherein a multitude of k-mers that shows a difference in frequency or context in the genome of the at least one microorganism compared to the genome of the subject are used as primers.

10. The method of claim 8, wherein a data base, which comprises a multitude of k-mers that shows a difference in frequency or context in the genome of at least one microorganism compared to the genome of a subject, is used to select the at least one k-mer that shows a difference in frequency or context in the genome of the at least one microorganism compared to the genome of the subject as primer in the amplification of the pathogen DNA sequences in the sample.

11. A method of selectively amplifying at least one pathogen DNA sequence of at least one microorganism, which is chosen from archaea, bacteria, protists, virus, or fungi, in a sample of a subject, which is a human patient, comprising:
   amplifying the pathogen DNA sequences in the sample using at least one k-mer,
   wherein the at least one k-mer consists of six nucleotides and that the at least one k-mer has a nucleotide sequence selected such that the at least one k-mer contains at least one CG motif, in either reading direction, and contains further nucleotides N;
   wherein N is any nucleotide and wherein the k-mer is enriched in the genome of the at least one microorganism relative to the human genome.

12. The method of claim 11, wherein the amplification is carried out using a k-mer or k-mer combination chosen such that the at least one k-mer has a nucleotide sequence selected as primer such that the at least one k-mer contains at least two CG motifs, in either reading direction, and contains further nucleotides N.

13. The method of claim 11, wherein a random k-mer is further used for amplification.

14. The method of claim 13, wherein the random k-mer consists of a k=6.

15. The method of claim 13, wherein the at least one k-mer is added in an amount of 1 μmol $L^{-1}$ to 1000 μmol $L^{-1}$, and the random k-mer is added in an amount of 1 pmol $L^{-1}$ to 100 nmol $L^{-1}$.

16. A method of selectively amplifying at least one pathogen DNA of at least one microorganism, which is chosen from archaea, bacteria, protists, virus, or fungi, in a sample of a subject, which is a human patient, comprising:
   amplifying the pathogen DNA sequences in the sample using at least one k-mer as primer, wherein the k-mer comprises in its sequence at least the sequence CG at any location of the k-mer sequence,
   wherein the at least one k-mer consists of six nucleotides and is enriched in the genome of the at least one microorganism relative to the human genome.

17. The method of claim 16, wherein a random k-mer is further used for amplification.

18. The method of claim 17, wherein the random k-mer has the same length as the at least one k-mer comprising in its sequence at least the sequence CG at any location of the k-mer sequence.

19. The method of claim 17, wherein the at least one k-mer comprising in its sequence at least the sequence CG at any location of the k-mer sequence is added in an amount of 1 μmol $L^{-1}$ to 1000 μmol $L^{-1}$, and the random k-mer is added in an amount of 1 pmol $L^{-1}$ to 100 nmol $L^{-1}$.

20. The method of claim 11, wherein the N is an A, T, G, C or U nucleotide.

21. The method of claim 1, wherein the k-mer frequency is the number of k-mers having a length of six nucleotides divided by the total sum of k-mers having a length of between 4 and 11 nucleotides occurring within the genome.

22. The method of claim 1, wherein the k-mer is enriched in the genome of the at least one microorganism relative to the human genome when the frequency of the k-mer in the genome of the at least one microorganism is greater than the frequency of the k-mer in the human genome.

23. The method of claim 1, wherein the k-mer is enriched in genomes of microorganisms and viruses.

24. The method of claim 1, wherein the k-mer is enriched greater than seven-fold in the genome of the at least one microorganism.

25. The method of claim 8, wherein the k-mer frequency is the number of k-mers having a length of six nucleotides divided by the total sum of k-mers having a length of between 4 and 11 nucleotides occurring within the genome.

26. The method of claim 8, wherein the k-mer is enriched in the genome of the at least one microorganism relative to the human genome when the frequency of the k-mer in the genome of the at least one microorganism is greater than the frequency of the k-mer in the human genome.

27. The method of claim 8, wherein the k-mer is enriched in genomes of microorganisms and viruses.

28. The method of claim 8, wherein the k-mer is enriched greater than seven-fold in the genome of the at least one microorganism.

29. The method of claim 11, wherein the k-mer is enriched in the genome of the at least one microorganism relative to the human genome when frequency of the k-mer in the genome of the at least one microorganism is greater than frequency of the k-mer in the human genome.

30. The method of claim 11, wherein the k-mer is enriched in genomes of microorganisms and viruses.

31. The method of claim 11, wherein the k-mer is enriched greater than seven-fold in the genome of the at least one microorganism.

* * * * *